US012717362B2

(12) United States Patent
Garcia Molina et al.

(10) Patent No.: US 12,717,362 B2
(45) Date of Patent: Aug. 25, 2026

(54) BED HAVING FEATURES FOR DETERMINING AND MODIFYING TEMPERATURE OF A SLEEP ENVIRONMENT

(71) Applicant: Sleep Number Corporation, Minneapolis, MN (US)

(72) Inventors: Gary N. Garcia Molina, Madison, WI (US); Yuki Hino, Dublin, CA (US); Dillon Pedersen, Saint Paul, MN (US); Shawn Barr, Berkeley, CA (US); Kody Lee Karschnik, Plymouth, MN (US); Farzad Siyahiani, San Jose, CA (US); Cory Lee Grabinger, Maple Grove, MN (US)

(73) Assignee: Sleep Number Corporation

( * ) Notice: Subject to any disclaimer, the term of this patent is extended or adjusted under 35 U.S.C. 154(b) by 872 days.

(21) Appl. No.: 17/559,515

(22) Filed: Dec. 22, 2021

(65) Prior Publication Data

US 2022/0261020 A1 Aug. 18, 2022

Related U.S. Application Data

(60) Provisional application No. 63/147,499, filed on Feb. 9, 2021.

(51) Int. Cl.
*G05D 23/19* (2006.01)
*A47C 21/04* (2006.01)
(Continued)

(52) U.S. Cl.
CPC ......... *G05D 23/1931* (2013.01); *A47C 21/04* (2013.01); *A47C 31/008* (2013.01);
(Continued)

(58) Field of Classification Search
CPC .. G05D 23/1931; A47C 21/04; A47C 31/008; A47C 21/044; A47C 21/048;
(Continued)

(56) References Cited

U.S. PATENT DOCUMENTS 6,473,920 B2 11/2002 Augustine et al.
6,711,767 B2 3/2004 Klamm
(Continued)

FOREIGN PATENT DOCUMENTS

CN 103561698 A 2/2014
CN 107072406 A 8/2017
(Continued)

OTHER PUBLICATIONS

U.S. Appl. No. 15/685,912, filed Aug. 24, 2017, Petrovski et al.
(Continued)

*Primary Examiner* — John E Breene
*Assistant Examiner* — Janice M Soto
(74) *Attorney, Agent, or Firm* — Norton Rose Fulbright US LLP

(57) ABSTRACT

A distal-proximal temperature-gradient of a sleeper is determined. A bed has a mattress. Temperature sensors are in an array. Each sensor is configured to: sense surface temperature of the sleeper of the bed, transmit, to a controller, temperature readings. The system also includes a controller may include a processor and memory, the controller configured to: receive, from each of the sensors, temperature readings at a particular time, access, for each temperature reading, a corresponding weight-value, determine the distal-proximal temperature-gradient for the sleeper at the particular time using the temperature readings and the corresponding weight-values.

18 Claims, 25 Drawing Sheets

(51) Int. Cl.
*A47C 31/00* (2006.01)
*A61B 5/00* (2006.01)
*A61B 5/01* (2006.01)
*A61B 5/0205* (2006.01)
*A61B 5/024* (2006.01)
*G01K 1/02* (2021.01)
*G05B 19/4155* (2006.01)

(52) U.S. Cl.
CPC ............ *A61B 5/01* (2013.01); *A61B 5/02055* (2013.01); *A61B 5/02405* (2013.01); *A61B 5/4809* (2013.01); *A61B 5/4812* (2013.01); *A61B 5/4815* (2013.01); *G01K 1/026* (2013.01); *G05B 19/4155* (2013.01); *A61B 2560/0252* (2013.01); *A61B 2562/0247* (2013.01); *A61B 2562/0271* (2013.01); *A61B 2562/043* (2013.01); *G05B 2219/50333* (2013.01)

(58) Field of Classification Search
CPC ..... A47C 31/123; A61B 5/01; A61B 5/02055; A61B 5/02405; A61B 5/4809; A61B 5/4812; A61B 5/4815; A61B 2560/0252; A61B 2562/0247; A61B 2562/0271; A61B 2562/043; G01K 1/026; G05B 19/4155; G05B 2219/50333
See application file for complete search history.

(56) References Cited

U.S. PATENT DOCUMENTS

| | | | | |
|---|---|---|---|---|
| 7,036,575 | B1 | 5/2006 | Rodney et al. | |
| 7,877,827 | B2 | 2/2011 | Comiskey et al. | |
| 7,996,936 | B2 | 8/2011 | Comiskey et al. | |
| 8,065,763 | B2 | 11/2011 | Brykalski et al. | |
| 8,181,290 | B2 | 5/2012 | Brykalski et al. | |
| 8,191,187 | B2 | 6/2012 | Brykalski et al. | |
| 8,332,975 | B2 | 12/2012 | Brykalski et al. | |
| 8,402,579 | B2 | 3/2013 | Comiskey et al. | |
| 8,418,286 | B2 | 4/2013 | Brykalski et al. | |
| 8,621,687 | B2 | 1/2014 | Brykalski et al. | |
| 8,732,874 | B2 | 5/2014 | Brykalski et al. | |
| 8,782,830 | B2 | 7/2014 | Brykalski et al. | |
| 8,893,329 | B2 | 11/2014 | Petrovski et al. | |
| 9,125,497 | B2 | 9/2015 | Brykalski et al. | |
| 9,131,781 | B2 | 9/2015 | Zaiss et al. | |
| 9,603,459 | B2 | 3/2017 | Brykalski et al. | |
| 9,622,588 | B2 | 4/2017 | Brykalski et al. | |
| 9,814,641 | B2 | 11/2017 | Brykalski et al. | |
| 9,974,394 | B2 | 5/2018 | Brykalski et al. | |
| 10,194,752 | B2 | 2/2019 | Zaiss et al. | |
| 10,226,134 | B2 | 3/2019 | Brykalski et al. | |
| 10,314,407 | B1 | 6/2019 | Main et al. | |
| 10,405,667 | B2 | 9/2019 | Comiskey et al. | |
| 10,675,198 | B2 | 6/2020 | Brykalski et al. | |
| 10,716,407 | B1 | 7/2020 | Bowman | |
| 10,772,438 | B2 | 9/2020 | Griffith et al. | |
| 11,020,298 | B2 | 6/2021 | Brykalski et al. | |
| 11,045,371 | B2 | 6/2021 | Brykalski et al. | |
| 11,083,308 | B2 | 8/2021 | Zaiss et al. | |
| 2010/0170043 | A1 | 7/2010 | Young et al. | |
| 2014/0026320 | A1 | 1/2014 | Comiskey et al. | |
| 2015/0238020 | A1 | 8/2015 | Petrovski et al. | |
| 2015/0265159 | A1* | 9/2015 | Lane | A61B 5/01 600/549 |
| 2016/0066701 | A1 | 3/2016 | Diller et al. | |
| 2017/0071359 | A1 | 3/2017 | Steele et al. | |
| 2017/0273470 | A1 | 9/2017 | Brykalski et al. | |
| 2017/0280883 | A1 | 10/2017 | Diller | |
| 2018/0027988 | A1* | 2/2018 | Poodeh | A47G 9/1027 |
| 2018/0116415 | A1 | 5/2018 | Karschnik et al. | |
| 2019/0038040 | A1* | 2/2019 | Mason | A47C 27/085 |
| 2020/0037776 | A1 | 2/2020 | Brykalski et al. | |
| 2020/0337470 | A1 | 10/2020 | Sayadi et al. | |
| 2021/0037987 | A1 | 2/2021 | Griffith et al. | |
| 2021/0038453 | A1 | 2/2021 | Brykalski et al. | |
| 2021/0204706 | A1 | 7/2021 | Karschnik et al. | |
| 2021/0204709 | A1 | 7/2021 | Grabinger et al. | |
| 2021/0204710 | A1 | 7/2021 | Grabinger et al. | |
| 2021/0204711 | A1 | 7/2021 | Karschnik et al. | |
| 2021/0204712 | A1 | 7/2021 | Karschnik et al. | |
| 2021/0204713 | A1 | 7/2021 | Karschnik et al. | |
| 2021/0204714 | A1 | 7/2021 | Karschnik et al. | |
| 2021/0204715 | A1 | 7/2021 | Karschnik et al. | |
| 2021/0204716 | A1 | 7/2021 | Karschnik et al. | |
| 2021/0204719 | A1 | 7/2021 | Grabinger et al. | |
| 2021/0204720 | A1 | 7/2021 | Karschnik et al. | |
| 2021/0322237 | A1 | 10/2021 | Brykalski et al. | |
| 2021/0322238 | A1 | 10/2021 | Brykalski et al. | |
| 2021/0401185 | A1 | 12/2021 | Zaiss et al. | |
| 2022/0087534 | A1* | 3/2022 | Mansky | A61B 5/01 |

FOREIGN PATENT DOCUMENTS

| | | | | |
|---|---|---|---|---|
| CN | 110006135 A | | 7/2019 | |
| CN | 110072432 A | | 7/2019 | |
| CN | 112236056 A | | 1/2021 | |
| JP | H5-228044 A | | 9/1993 | |
| JP | 2008119454 A | | 5/2008 | |
| JP | 6182153 | | 8/2017 | |
| WO | WO 2018/023135 | | 2/2018 | |
| WO | WO-2018023135 A1 | * | 2/2018 | A47C 21/04 |

OTHER PUBLICATIONS

U.S. Appl. No. 15/973,279, filed May 7, 2018, Brykalski et al.
U.S. Appl. No. 17/683,594, filed Mar. 1, 2022, Karschnik et al.
U.S. Appl. No. 17/692,959, filed Mar. 11, 2022, Karschnik et al.
Csernai et al, "Dynamics of sleep oscillations is coupled to brain temperature on multiple scales," The Journal of Physiology, Aug. 2019, 597(15):4069-4086.
Krauchi et al., "Body Temperature, Sleep, and Hibernation," Principles and Practice of Sleep Medicine, Fifth ed., 2011, Chapter 28, 2011, 323-334.
Longato et al., "Expected accuracy of proximal and distal temperature estimated by wireless sensors, in relation to their number and position on the skin," PLoS One, Jun. 2017, 12(6):e0180315, 13 pages.
Okamoto-mizuno et al., "Heart rate variability and body temperature during the sleep onset period," Sleep and Biological Rhythms, Jan. 2008, 6(1):42-49.
Song et al., "Effects of phased sleeping thermal environment regulation on human thermal comfort and sleep quality," Building and Environment, Aug. 2020, 181(107108):1-14.
Szymusiak, "Chapter 20—Body Temperature and Sleep," Handbook of Clinical Neurology, 2018, 156:341-351.
Tanabe et al., "Evaluating thermal environments by using a thermal manikin with controlled skin surface temperature," ASHRAE J., 1994, 100:39-48, 11 pages.
Van Someren, "Mechanisms and functions of coupling between sleep and temperature rhythms," Progress in Brain Research, 2006, 153:309-324.
International Search Report and Written Opinion in International Appln. No. PCT/US2021/064907, mailed Apr. 11, 2022, 12 pages.
International Preliminary Report on Patentability in International Appln. No. PCT/US2021/064907, mailed on Aug. 24, 2023, 7 pages.
Office Action in Japanese Appln. No. 2023-547774, mailed on Jul. 31, 2025, 12 pages (with English translation).

* cited by examiner

402

414

410a

BED HAVING FEATURES FOR DETERMINING AND MODIFYING TEMPERATURE OF A SLEEP ENVIRONMENT

CROSS-REFERENCE TO RELATED APPLICATIONS

This application claims the benefit of U.S. Provisional Application Ser. No. 63/147,499, filed Feb. 9, 2021. The disclosure of the prior application is considered part of (and is incorporated by reference in) the disclosure of this application.

The present document relates to beds with computer hardware

BACKGROUND

In general, a bed is a piece of furniture used as a location to sleep or relax. Many modern beds include a soft mattress on a bed frame. The mattress may include springs, foam material, and/or an air chamber to support the weight of one or more occupants.

SUMMARY

In general, this document describes technology for controlling and improving in-bed microclimates to improve a bed occupant's quality of sleep. Core body temperature (CBT), skin temperature, mattress temperatures, and/or environmental temperatures can be used to determine one or more thermal microclimates for a bed system. When a sleep environment is conceptualized as having different component microclimates, beds can be designed to control each microclimate separately. Modulating different microclimates independently of each other can improve the occupant's quality of sleep since the microclimates can target different portions of the occupant's body experiencing different temperature values. A temperature sensor array can be positioned on a mattress of the bed system. The sensor array can be configured to sense skin and mattress temperatures, which can be used by the bed system to determine, control, and improve the microclimates of the bed system. In some implementations, the sensor array can also include sensors that read pressure values. Using the pressure values, the bed system can determine a position or posture of the occupant's body. The position of the occupant's body can be used to aid in measuring temperatures of the occupant's body to further adjust or optimize the microclimates.

For example, the sensor array can collect temperature readings of the occupant's skin as well as pressure readings. Using the pressure readings, a posture of the occupant can be determined. A coefficient or weighted valued associated with that posture can then be used in conjunction with the collected temperature readings to determine a distal-to-proximal temperature-gradient (DPG) for the occupant. Using the determined DPG, the bed system can modulate or optimize the microclimates to provide the occupant with improved sleep quality.

The disclosed technology can be used to measure DPG while falling asleep, proximal temperatures, distal temperatures, CBT during sleep, and a mattress temperature. Each of the microclimates can be adjusted depending on interaction between one or more of the DPG proximal and distal temperatures, CBT, and mattress temperature. Microclimate adjustments can also depend on cardiac measures, such as heartrate (HR) and heartrate variability (HRV) and/or respiratory metrics such as respiratory rate. The disclosed embodiments can provide for real-time tracking of such information to dynamically adjust microclimates of the bed system, improve the occupant's quality of sleep, and identify potential cardiovascular health conditions while the occupant is asleep.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a sensor system for determining a distal-proximal temperature-gradient of a sleeper. The system has a bed having a mattress. The sensor system also includes an array of temperature sensors, each sensor configured to: sense surface temperature of the sleeper of the bed, transmit, to a controller, temperature readings. The system also includes a controller that may include a processor and memory, the controller configured to: receive, from each of the sensors, temperature readings at a particular time, access, for each temperature reading, a corresponding weight-value, and determine the distal-proximal temperature-gradient for the sleeper at the particular time using the temperature readings and the corresponding weight-values. Other embodiments of this aspect include corresponding computer systems, apparatus, and computer programs recorded on one or more computer storage devices, each configured to perform the actions of the methods.

Implementations may include one or more of the following features. The sensor system where the array of temperature sensors is a linear array. The linear array has a linear axis; the bed has a sleeper section adapted to support the sleeper, the sleeper section has a major axis through a center of a longest dimension of the sleeper section; and where the linear array is situated so that the linear axis is perpendicular to the major axis. At least one of the sensors is more responsive to proximal temperature of the sleeper than to distal temperature of the sleeper; and at least another of the sensors is more responsive to distal temperature of the sleeper than to proximal temperature of the sleeper. Each of the sensors is at least partially responsive to proximal temperature of the sleeper and to distal temperature of the sleeper. The array of temperature sensors may include of five temperature sensors. A lookup table records the weight-values in a look-up table indexed by sleep posture and sensor identifier; and to access, for each temperature reading, a corresponding weight-value, the controller is further configured to: look up, in the look-up table, the corresponding weight-values using the sleep posture of the sleeper and sensor identifiers of the temperature sensors. Pressure readings from a pressure sensor are used by the controller to determine the sleep posture of the sleeper. To determine the distal-proximal temperature-gradient for the sleeper at the particular time using the temperature readings and the corresponding weight-values, the controller is further configured to: find weighted-temperatures by weighing each of the temperature readings by the corresponding weight-value; and find an aggregate of the weighted temperatures. Each weight-value is a number between zero and one, inclusive; and to weigh each of the temperature readings by the corresponding weight-value, the controller is further configured to multiply each of the temperature readings by the corresponding weight-value. The aggregate is a linear combination of temperatures. To determine the distal-proximal temperature-gradient for the sleeper at the particular time using the temperature readings and the corresponding weight-values, the controller is further configured to use cardiac measures of the sleeper. The controller is further configured to engage one or more thermal controllers to adjust the sleep environment to a target thermal environment determined using the distal-proximal temperature-gradient. The controller is further configured to use the distal-proximal temperature-gradient to engage one or more thermal controllers to adjust the sleep environment until a target distal-proximal temperature-gradient is detected. The controller is further configured to use the distal-proximal temperature-gradient to annotate sleep-session information for the sleeper stored in a data store. The controller is further configured to use the distal-proximal temperature-gradient to generate sleep-quality information for the sleeper's sleep session at the particular time. The controller is further configured to generate the sleep-quality information using at least one of the group may include: sleep onset latency, sleep fragmentation, length of deep sleep, length of rem sleep, and subjective assessment of sleep by the sleeper after the sleep session. The controller is further configured to use the distal-proximal temperature-gradient to generate a wellness metric for the sleeper. Implementations of the described techniques may include hardware, a method or process, or computer software on a computer-accessible medium.

One or more advantages can be apparent from the disclosed embodiments. For example, the disclosed embodiments can provide for improved temperature control of one or more microclimates of the bed system. By use of technology described here, microclimates can be controlled to a greater degree than other technology that does not use same hardware and software. For example, this technology may provide more accurate measures, and more consistent temperature control, than alternatives using discharge temperature sensors at an outlet of a heating/cooling engine. By using an array of sensors in to capture different temperature readings at several points around and under the bed occupant, measurement of the actual phenomena of interest (the environment of the sleeper) can be directly measured. In some other systems, variations in bedding, room temperature, occupant position on the bed, and heat generated by the occupant can change the actual microclimate temperature from a desired target temperature established by such bed systems. This can cause different user experiences and decreased quality of sleep. The array of sensors can also be used to derive different averages and weighted temperatures for average microclimates, mattress, and bed occupant skin temperatures. This data can provide for consistent control over one or more microclimates of the bed to provide the occupant with improved or higher sleep quality.

Moreover, by determining the DPG of the bed occupant, the bed system can provide for individual adjustment or modulation of temperature values in one or more microclimates of the bed system. For example, a proximal temperature can be increased in one or more microclimates while a distal temperature can be decreased in one or more other microclimates of the bed system. Such adjustments can occur simultaneously or at different times to provide the occupant with seamless adjustment of microclimates and continuous comfort while falling asleep and during sleep. Continuous and/or target adjustment of different microclimates can help the occupant fall asleep faster, stay asleep, and/or experience an improved overall quality of sleep.

The disclosed embodiments can also provide for small changes in temperature that can be unrecognizable by the occupant but still beneficial. Minute adjustments to different microclimates can help the occupant remain comfortable while falling asleep and during sleep. For example, alternative bed systems can provide a noticeable increase in temperature of the overall bed system. The occupant may feel discomfort if the entire bed suddenly is too warm, or portions of the occupant's body that have higher temperatures (e.g., the core) begin to overheat and/or sweat. As a result, the occupant may experience decreased sleep quality and/or may have difficulty falling asleep. The disclosed embodiments, on the other hand, provide for minimal changes in temperature in one or more different microclimates that may be unrecognizable by the occupant. Minimal temperature changes can improve the occupant's quality of sleep and/or ability to fall asleep since these minimal changes cause the occupant's body, skin temperatures and even cardiac or respiratory metrics to change. Therefore, the occupant's body or skin temperatures can be directly impacted by slight changes in microclimate temperatures to improve the occupant's sleep experience and maintain the occupant's comfort while in the bed.

The disclosed embodiments can also provide for improved collection and use of occupant biometrics to improve quality of sleep and for other purposes. For example, compared to beds that do not operate with respect to the occupant's presence in the bed, actual sleep status, or quality of sleep, this technology can collect occupant biometrics in real-time as an additional feedback mechanism. For example, the disclosed embodiments can provide for collection of pressure readings and cardiac measures and/or respiratory measures. The pressure readings can be used to determine a posture of the occupant, which can be used to identify the occupant's DPG and modulation of one or more microclimates. The cardiorespiratory measures can also be used to identify the DPG and modulate the microclimates. The cardiac measures can also be used to identify any potential cardiovascular health conditions of the occupant while they are asleep. Since the bed system collects and analyzes different biometrics, the bed system can dynamically adjust thermal stimulus over a sleep session to enhance and improve the occupant's sleep quality.

As yet another example, the disclosed embodiments can help the bed occupant fall asleep faster. Because temperature readings of the occupant's body, the bed system, and the environment can be sensed in real-time before and during the occupant's sleep, temperatures of one or more microclimates can be dynamically adjusted to compliment the occupant's body temperatures. The occupant may not feel or notice a changes in temperature that otherwise can disrupt the occupant's sleep or quality of sleep. Instead, portions of the occupant's body can be impacted by slight changes in temperature in different microclimates intended to promote sleepiness in the occupant.

Moreover, the disclosed embodiments provides for customizing microclimates based on the occupant's specific body temperatures and biometrics. The bed system can have different microclimates based on an occupant or multiple occupants. For example, if two occupants are in the bed, the disclosed embodiments provide for adjusting one or more microclimates in real-time per occupant. Therefore, each occupant can experience improved quality of sleep. As another example, the bed system can have different microclimates for different occupants who use the bed at different times. As a result, any occupant of the bed can experience an improved quality of sleep as the bed system dynamically modifies one or more microclimates based on that occupant's body temperatures and other biometric values.

Other features, aspects and potential advantages will be apparent from the accompanying description and figures.

DESCRIPTION OF DRAWINGS

Like reference symbols in the various drawings indicate like elements.

DETAILED DESCRIPTION

Figure 1:
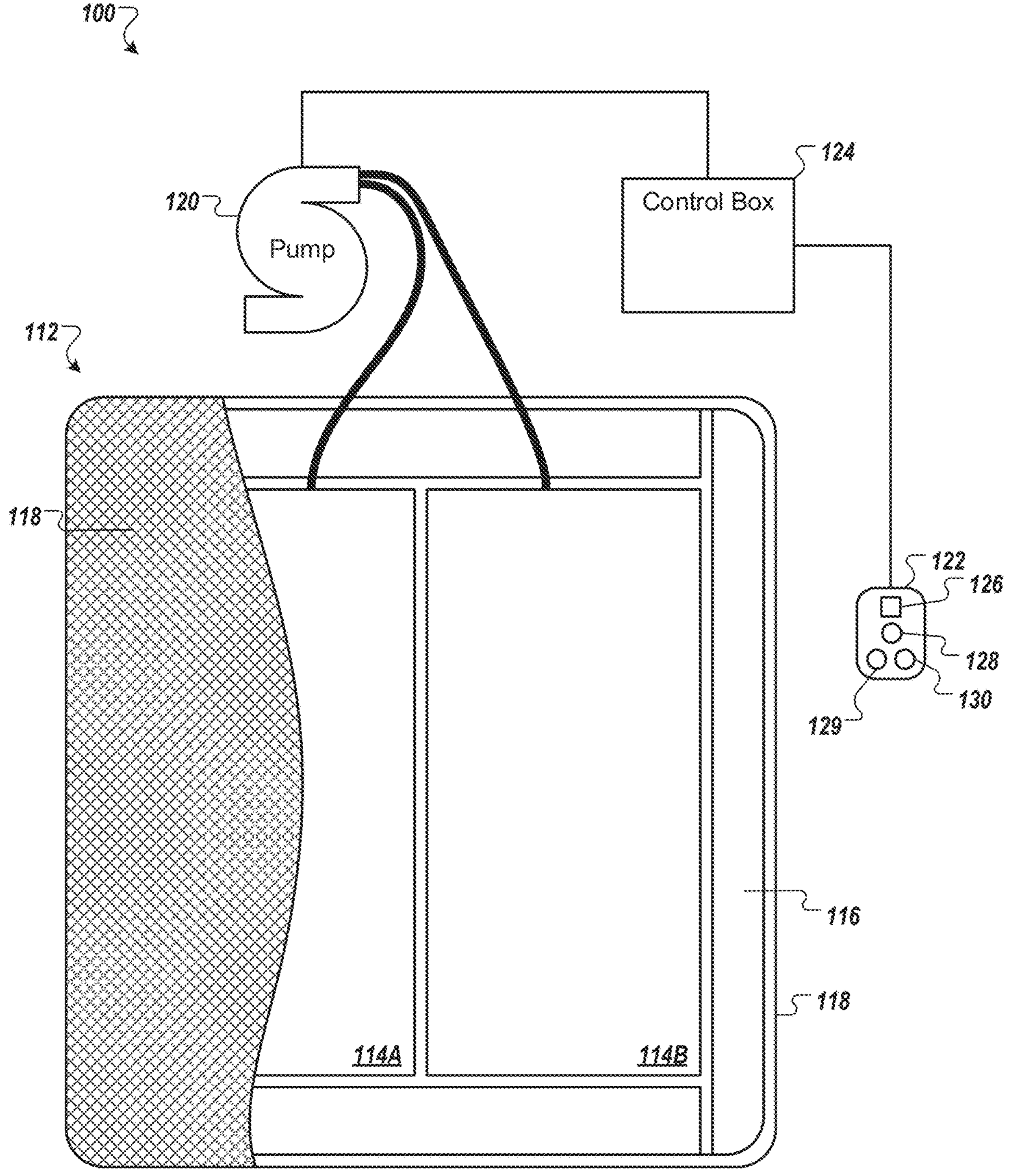
FIG. 1 shows an example air bed system.

In general, this documents describes a system for optimizing sleep quality of occupants of a bed system. The disclosed embodiments can provide for determining microclimates suited for improving the occupant's sleep quality (e.g., longer, deeper sleep; minimally fragmented sleep with fewer interruptions) and/or helping the occupant fall asleep faster. A shell body temperature can have a strong correlation with core body temperature; and core body temperature can be a driving factor in core body temperature fluctuations (e.g., skin temperature increases before sleep onset to facilitate heat dissipation and consequently decrease CBT). The shell temperature can also be divided into proximal and distal temperatures. Proximal body temperature can be determined from temperature readings from (MA), (LIA), abdomen (A), (RMT) and (LMT). Distal temperature can be a temperature of right hand (RH), left hand (LH), right foot (RL) and left foot (LF). The shell body temperature can expand around sleep time. At sleep onset, distal and proximal skin temperatures can also increase. A distal-proximal temperature-gradient (DPG) can reflect a vasodilation at the occupant's extremities, which can be a predictor of the occupant's readiness for sleep. Therefore, the disclosed embodiments provide for a DPG-based temperature feedback and control loop to improve the occupant's quality of sleep. For example, a heat-capacity of a mattress can be a factor for an occupant's sleep microclimate. The higher the mattress heat-capacity is, the lower core-body (CBT) and proximal (PRO) temperature can be during sleep. Low CBT and PRO can lead to higher sleep quality and lower heart rates (HR).

In general, changes in an environment can affect a bed occupant's sleep quality. For example, environmental temperatures can influence body temperatures, which can cause the occupant's sleep quality to fluctuate. Core body temperature (CBT) and skin temperature (proximal and distal) can change during sleep, which can also affect the occupant's sleep quality. For example, CBT can decrease as sleep initiates and can keep decreasing for approximately a first half of the occupant's sleep. During a second half of the occupant's sleep, CBT can progressively increase to its wakefulness level (e.g., ~37 □C). The magnitude of this CBT change can be approximately 1 □C, which can impact the occupant's overall sleep quality. Skin temperature can also exhibit temperature changes related to CBT changes. For example, during a falling asleep process, skin temperature can increase to facilitate core heat dissipation. This can cause a decrease in CBT. External factors, such as mattress temperature and environmental temperature, can influence the bed occupant's overall sleep quality.

Sleep quality can be measured based on a number of factors. These factors can include, but are not limited to sleep onset latency (e.g., less than 10 minutes), low sleep fragmentation (e.g., wake up after sleep onset is less than 20 minutes), long sleep duration (e.g., exceeding a standard deviation from a habitual sleep duration), longer deep sleep, longer REM sleep, and/or subjective feedback

Example Airbed Hardware

FIG. 1 shows an example air bed system 100 that includes a bed 112. The bed 112 includes at least one air chamber 114 surrounded by a resilient border 116 and encapsulated by bed ticking 118. The resilient border 116 can comprise any suitable material, such as foam.

As illustrated in FIG. 1, the bed 112 can be a two chamber design having first and second fluid chambers, such as a first air chamber 114A and a second air chamber 114B. In alternative embodiments, the bed 112 can include chambers for use with fluids other than air that are suitable for the application. In some embodiments, such as single beds or kids' beds, the bed 112 can include a single air chamber 114A or 114B or multiple air chambers 114A and 114B. First and second air chambers 114A and 114B can be in fluid communication with a pump 120. The pump 120 can be in electrical communication with a remote control 122 via control box 124. The control box 124 can include a wired or wireless communications interface for communicating with one or more devices, including the remote control 122. The control box 124 can be configured to operate the pump 120 to cause increases and decreases in the fluid pressure of the first and second air chambers 114A and 114B based upon commands input by a user using the remote control 122. In some implementations, the control box 124 is integrated into a housing of the pump 120.

The remote control 122 can include a display 126, an output selecting mechanism 128, a pressure increase button 129, and a pressure decrease button 130. The output selecting mechanism 128 can allow the user to switch air flow generated by the pump 120 between the first and second air chambers 114A and 114B, thus enabling control of multiple air chambers with a single remote control 122 and a single pump 120. For example, the output selecting mechanism 128 can by a physical control (e.g., switch or button) or an input control displayed on display 126. Alternatively, separate remote control units can be provided for each air chamber and can each include the ability to control multiple air chambers. Pressure increase and decrease buttons 129 and 130 can allow a user to increase or decrease the pressure, respectively, in the air chamber selected with the output selecting mechanism 128. Adjusting the pressure within the selected air chamber can cause a corresponding adjustment to the firmness of the respective air chamber. In some embodiments, the remote control 122 can be omitted or modified as appropriate for an application. For example, in some embodiments the bed 112 can be controlled by a computer, tablet, smart phone, or other device in wired or wireless communication with the bed 112.

Figure 2:
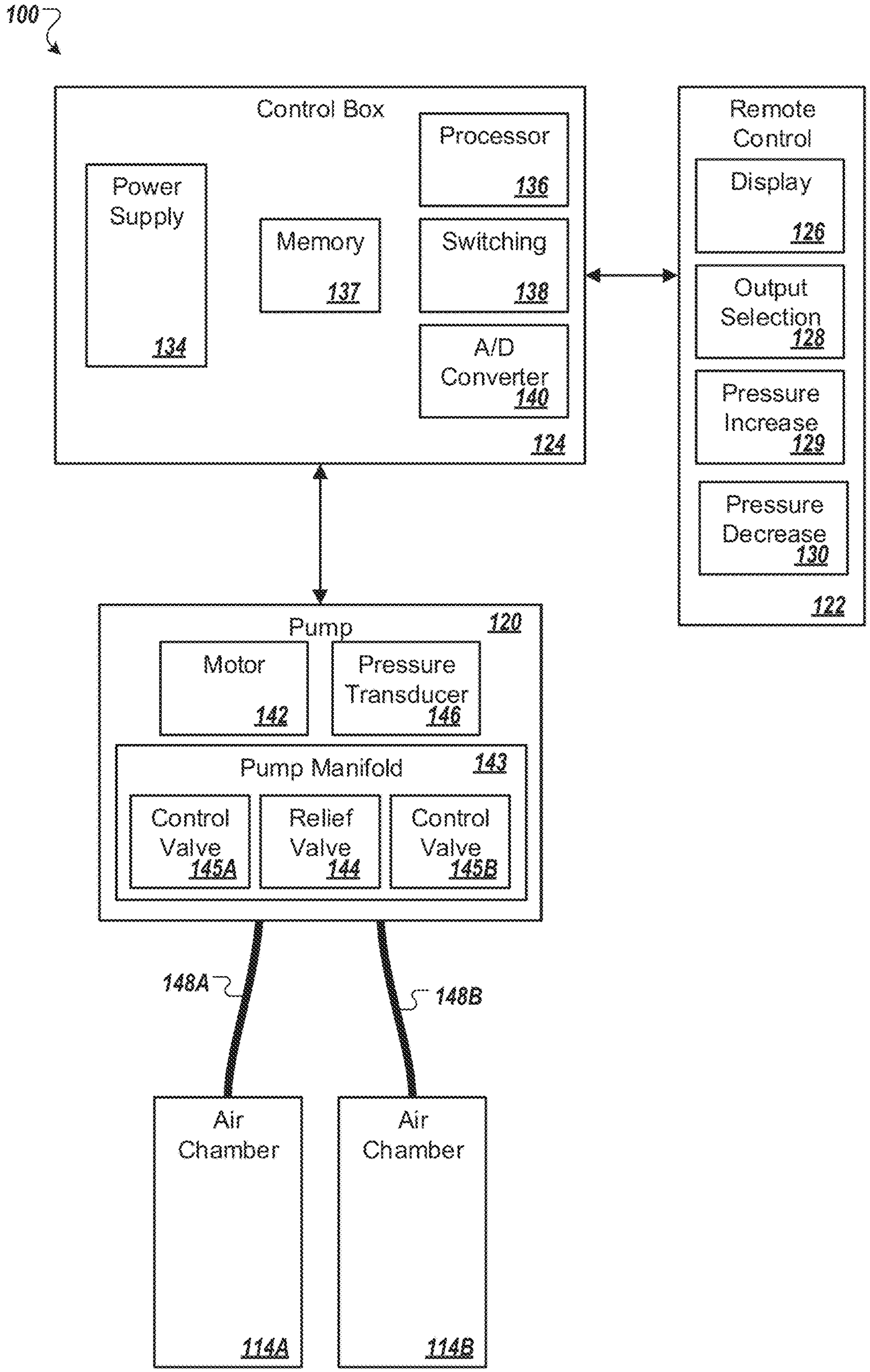
FIG. 2 is a block diagram of an example of various components of an air bed system.

FIG. 2 is a block diagram of an example of various components of an air bed system. For example, these components can be used in the example air bed system 100. As shown in FIG. 2, the control box 124 can include a power supply 134, a processor 136, a memory 137, a switching mechanism 138, and an analog to digital (A/D) converter 140. The switching mechanism 138 can be, for example, a relay or a solid state switch. In some implementations, the switching mechanism 138 can be located in the pump 120 rather than the control box 124.

The pump 120 and the remote control 122 are in two-way communication with the control box 124. The pump 120 includes a motor 142, a pump manifold 143, a relief valve 144, a first control valve 145A, a second control valve 145B, and a pressure transducer 146. The pump 120 is fluidly connected with the first air chamber 114A and the second air chamber 114B via a first tube 148A and a second tube 148B, respectively. The first and second control valves 145A and 145B can be controlled by switching mechanism 138, and are operable to regulate the flow of fluid between the pump 120 and first and second air chambers 114A and 114B, respectively.

In some implementations, the pump 120 and the control box 124 can be provided and packaged as a single unit. In some alternative implementations, the pump 120 and the control box 124 can be provided as physically separate units. In some implementations, the control box 124, the pump 120, or both are integrated within or otherwise contained within a bed frame or bed support structure that supports the bed 112. In some implementations, the control box 124, the pump 120, or both are located outside of a bed frame or bed support structure (as shown in the example in FIG. 1).

The example air bed system 100 depicted in FIG. 2 includes the two air chambers 114A and 114B and the single pump 120. However, other implementations can include an air bed system having two or more air chambers and one or more pumps incorporated into the air bed system to control the air chambers. For example, a separate pump can be associated with each air chamber of the air bed system or a pump can be associated with multiple chambers of the air bed system. Separate pumps can allow each air chamber to be inflated or deflated independently and simultaneously. Furthermore, additional pressure transducers can also be incorporated into the air bed system such that, for example, a separate pressure transducer can be associated with each air chamber.

In use, the processor 136 can, for example, send a decrease pressure command to one of air chambers 114A or 114B, and the switching mechanism 138 can be used to convert the low voltage command signals sent by the processor 136 to higher operating voltages sufficient to operate the relief valve 144 of the pump 120 and open the control valve 145A or 145B. Opening the relief valve 144 can allow air to escape from the air chamber 114A or 114B through the respective air tube 148A or 148B. During deflation, the pressure transducer 146 can send pressure readings to the processor 136 via the A/D converter 140. The A/D converter 140 can receive analog information from pressure transducer 146 and can convert the analog information to digital information useable by the processor 136. The processor 136 can send the digital signal to the remote control 122 to update the display 126 in order to convey the pressure information to the user.

As another example, the processor 136 can send an increase pressure command. The pump motor 142 can be energized in response to the increase pressure command and send air to the designated one of the air chambers 114A or 114B through the air tube 148A or 148B via electronically operating the corresponding valve 145A or 145B. While air is being delivered to the designated air chamber 114A or 114B in order to increase the firmness of the chamber, the pressure transducer 146 can sense pressure within the pump manifold 143. Again, the pressure transducer 146 can send pressure readings to the processor 136 via the A/D converter 140. The processor 136 can use the information received from the A/D converter 140 to determine the difference between the actual pressure in air chamber 114A or 114B and the desired pressure. The processor 136 can send the digital signal to the remote control 122 to update display 126 in order to convey the pressure information to the user.

Generally speaking, during an inflation or deflation process, the pressure sensed within the pump manifold 143 can provide an approximation of the pressure within the respective air chamber that is in fluid communication with the pump manifold 143. An example method of obtaining a pump manifold pressure reading that is substantially equivalent to the actual pressure within an air chamber includes turning off pump 120, allowing the pressure within the air chamber 114A or 114B and the pump manifold 143 to equalize, and then sensing the pressure within the pump manifold 143 with the pressure transducer 146. Thus, providing a sufficient amount of time to allow the pressures within the pump manifold 143 and chamber 114A or 114B to equalize can result in pressure readings that are accurate approximations of the actual pressure within air chamber 114A or 114B. In some implementations, the pressure of the air chambers 114A and/or 114B can be continuously monitored using multiple pressure sensors (not shown).

In some implementations, information collected by the pressure transducer 146 can be analyzed to determine various states of a person lying on the bed 112. For example, the processor 136 can use information collected by the pressure transducer 146 to determine a heart rate or a respiration rate for a person lying in the bed 112. For example, a user can be lying on a side of the bed 112 that includes the chamber 114A. The pressure transducer 146 can monitor fluctuations in pressure of the chamber 114A and this information can be used to determine the user's heart rate and/or respiration rate. As another example, additional processing can be performed using the collected data to determine a sleep state of the person (e.g., awake, light sleep, deep sleep). For example, the processor 136 can determine when a person falls asleep and, while asleep, the various sleep states of the person.

Additional information associated with a user of the air bed system 100 that can be determined using information collected by the pressure transducer 146 includes motion of the user, presence of the user on a surface of the bed 112, weight of the user, heart arrhythmia of the user, and apnea. Taking user presence detection for example, the pressure transducer 146 can be used to detect the user's presence on the bed 112, e.g., via a gross pressure change determination and/or via one or more of a respiration rate signal, heart rate signal, and/or other biometric signals. For example, a simple pressure detection process can identify an increase in pressure as an indication that the user is present on the bed 112. As another example, the processor 136 can determine that the user is present on the bed 112 if the detected pressure increases above a specified threshold (so as to indicate that a person or other object above a certain weight is positioned on the bed 112). As yet another example, the processor 136 can identify an increase in pressure in combination with detected slight, rhythmic fluctuations in pressure as corresponding to the user being present on the bed 112. The presence of rhythmic fluctuations can be identified as being caused by respiration or heart rhythm (or both) of the user. The detection of respiration or a heartbeat can distinguish between the user being present on the bed and another object (e.g., a suit case) being placed upon the bed.

In some implementations, fluctuations in pressure can be measured at the pump 120. For example, one or more pressure sensors can be located within one or more internal cavities of the pump 120 to detect fluctuations in pressure within the pump 120. The fluctuations in pressure detected at the pump 120 can indicate fluctuations in pressure in one or both of the chambers 114A and 114B. One or more sensors located at the pump 120 can be in fluid communication with the one or both of the chambers 114A and 114B, and the sensors can be operative to determine pressure within the chambers 114A and 114B. The control box 124 can be configured to determine at least one vital sign (e.g., heart rate, respiratory rate) based on the pressure within the chamber 114A or the chamber 114B.

In some implementations, the control box 124 can analyze a pressure signal detected by one or more pressure sensors to determine a heart rate, respiration rate, and/or other vital signs of a user lying or sitting on the chamber 114A or the chamber 114B. More specifically, when a user lies on the bed 112 positioned over the chamber 114A, each of the user's heart beats, breaths, and other movements can create a force on the bed 112 that is transmitted to the chamber 114A. As a result of the force input to the chamber 114A from the user's movement, a wave can propagate through the chamber 114A and into the pump 120. A pressure sensor located at the pump 120 can detect the wave, and thus the pressure signal output by the sensor can indicate a heart rate, respiratory rate, or other information regarding the user.

With regard to sleep state, air bed system 100 can determine a user's sleep state by using various biometric signals such as heart rate, respiration, and/or movement of the user. While the user is sleeping, the processor 136 can receive one or more of the user's biometric signals (e.g., heart rate, respiration, and motion) and determine the user's present sleep state based on the received biometric signals. In some implementations, signals indicating fluctuations in pressure in one or both of the chambers 114A and 114B can be amplified and/or filtered to allow for more precise detection of heart rate and respiratory rate.

The control box 124 can perform a pattern recognition algorithm or other calculation based on the amplified and filtered pressure signal to determine the user's heart rate and respiratory rate. For example, the algorithm or calculation can be based on assumptions that a heart rate portion of the signal has a frequency in the range of 0.5-4.0 Hz and that a respiration rate portion of the signal a has a frequency in the range of less than 1 Hz. The control box 124 can also be configured to determine other characteristics of a user based on the received pressure signal, such as blood pressure, tossing and turning movements, rolling movements, limb movements, weight, the presence or lack of presence of a user, and/or the identity of the user. Techniques for monitoring a user's sleep using heart rate information, respiration rate information, and other user information are disclosed in U.S. Patent Application Publication No. 20100170043 to Steven J. Young et al., titled "APPARATUS FOR MONITORING VITAL SIGNS," the entire contents of which is incorporated herein by reference.

For example, the pressure transducer 146 can be used to monitor the air pressure in the chambers 114A and 114B of the bed 112. If the user on the bed 112 is not moving, the air pressure changes in the air chamber 114A or 114B can be relatively minimal, and can be attributable to respiration and/or heartbeat. When the user on the bed 112 is moving, however, the air pressure in the mattress can fluctuate by a much larger amount. Thus, the pressure signals generated by the pressure transducer 146 and received by the processor 136 can be filtered and indicated as corresponding to motion, heartbeat, or respiration.

In some implementations, rather than performing the data analysis in the control box 124 with the processor 136, a digital signal processor (DSP) can be provided to analyze the data collected by the pressure transducer 146. Alternatively, the data collected by the pressure transducer 146 could be sent to a cloud-based computing system for remote analysis.

In some implementations, the example air bed system 100 further includes a temperature controller configured to increase, decrease, or maintain the temperature of a bed, for example for the comfort of the user. For example, a pad can be placed on top of or be part of the bed 112, or can be placed on top of or be part of one or both of the chambers 114A and 114B. Air can be pushed through the pad and vented to cool off a user of the bed. Conversely, the pad can include a heating element that can be used to keep the user warm. In some implementations, the temperature controller can receive temperature readings from the pad. In some implementations, separate pads are used for the different sides of the bed 112 (e.g., corresponding to the locations of the chambers 114A and 114B) to provide for differing temperature control for the different sides of the bed.

In some implementations, the user of the air bed system 100 can use an input device, such as the remote control 122, to input a desired temperature for the surface of the bed 112 (or for a portion of the surface of the bed 112). The desired temperature can be encapsulated in a command data structure that includes the desired temperature as well as identifies the temperature controller as the desired component to be controlled. The command data structure can then be transmitted via Bluetooth or another suitable communication protocol to the processor 136. In various examples, the command data structure is encrypted before being transmitted. The temperature controller can then configure its elements to increase or decrease the temperature of the pad depending on the temperature input into remote control 122 by the user.

In some implementations, data can be transmitted from a component back to the processor 136 or to one or more display devices, such as the display 126. For example, the current temperature as determined by a sensor element of temperature controller, the pressure of the bed, the current position of the foundation or other information can be transmitted to control box 124. The control box 124 can then transmit the received information to remote control 122 where it can be displayed to the user (e.g., on the display 126).

In some implementations, the example air bed system 100 further includes an adjustable foundation and an articulation controller configured to adjust the position of a bed (e.g., the bed 112) by adjusting the adjustable foundation that supports the bed. For example, the articulation controller can adjust the bed 112 from a flat position to a position in which a head portion of a mattress of the bed is inclined upward (e.g., to facilitate a user sitting up in bed and/or watching television). In some implementations, the bed 112 includes multiple separately articulable sections. For example, portions of the bed corresponding to the locations of the chambers 114A and 114B can be articulated independently from each other, to allow one person positioned on the bed 112 surface to rest in a first position (e.g., a flat position) while a second person rests in a second position (e.g., an reclining position with the head raised at an angle from the waist). In some implementations, separate positions can be set for two different beds (e.g., two twin beds placed next to each other). The foundation of the bed 112 can include more than one zone that can be independently adjusted. The articulation controller can also be configured to provide different levels of massage to one or more users on the bed 112.

Example of a Bed in a Bedroom Environment

Figure 3:
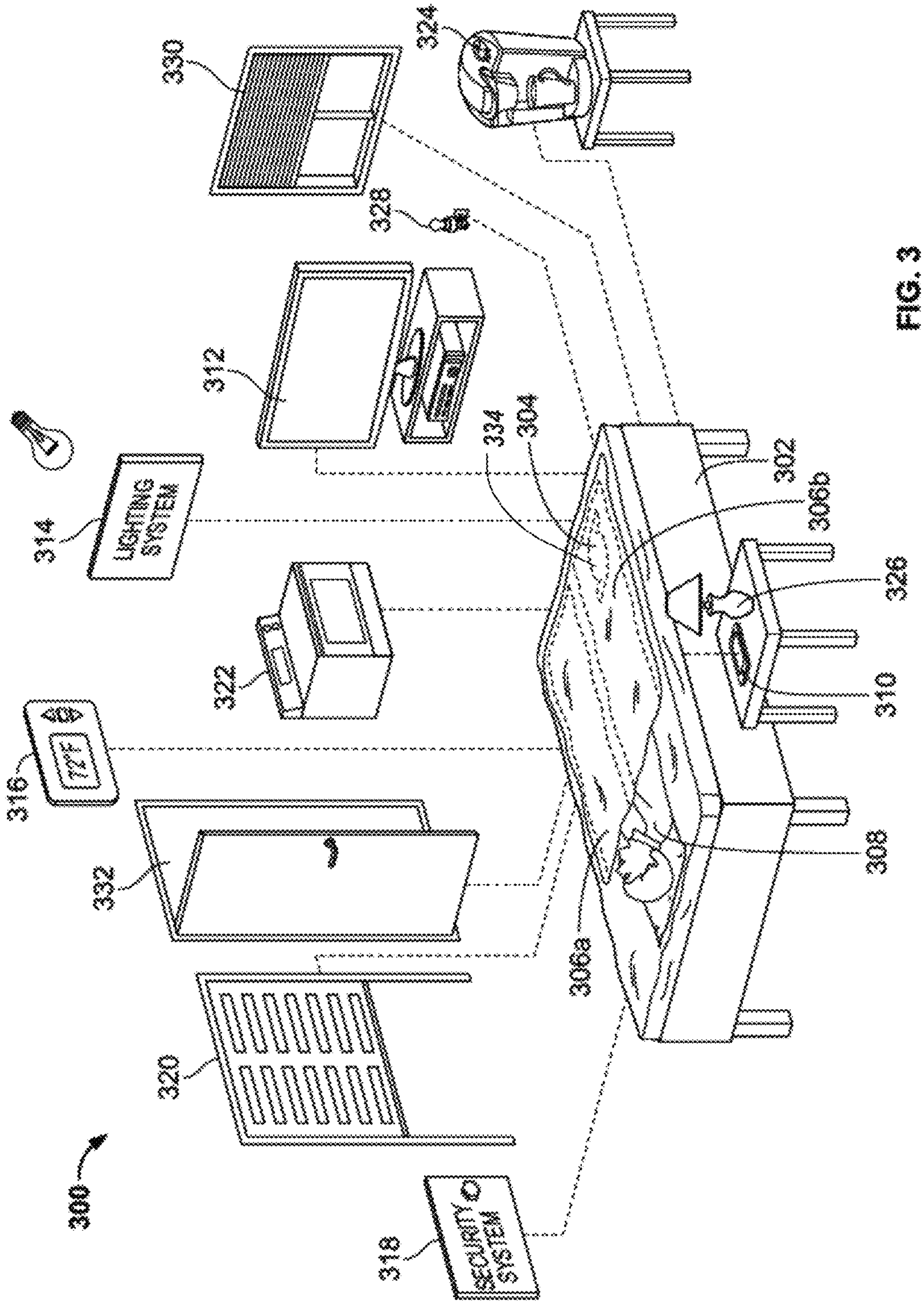
FIG. 3 shows an example environment including a bed in communication with devices located in and around a home.

FIG. 3 shows an example environment 300 including a bed 302 in communication with devices located in and around a home. In the example shown, the bed 302 includes pump 304 for controlling air pressure within two air chambers 306*a* and 306*b* (as described above with respect to the air chambers 114A-114B). The pump 304 additionally includes circuitry for controlling inflation and deflation functionality performed by the pump 304. The circuitry is further programmed to detect fluctuations in air pressure of the air chambers 306*a-b* and used the detected fluctuations in air pressure to identify bed presence of a user 308, sleep state of the user 308, movement of the user 308, and biometric signals of the user 308 such as heart rate and respiration rate. In the example shown, the pump 304 is located within a support structure of the bed 302 and the control circuitry 334 for controlling the pump 304 is integrated with the pump 304. In some implementations, the control circuitry 334 is physically separate from the pump 304 and is in wireless or wired communication with the pump 304. In some implementations, the pump 304 and/or control circuitry 334 are located outside of the bed 302. In some implementations, various control functions can be performed by systems located in different physical locations. For example, circuitry for controlling actions of the pump 304 can be located within a pump casing of the pump 304 while control circuitry 334 for performing other functions associated with the bed 302 can be located in another portion of the bed 302, or external to the bed 302. As another example, control circuitry 334 located within the pump 304 can communicate with control circuitry 334 at a remote location through a LAN or WAN (e.g., the internet). As yet another example, the control circuitry 334 can be included in the control box 124 of FIGS. 1 and 2.

In some implementations, one or more devices other than, or in addition to, the pump 304 and control circuitry 334 can be utilized to identify user bed presence, sleep state, movement, and biometric signals. For example, the bed 302 can include a second pump in addition to the pump 304, with each of the two pumps connected to a respective one of the air chambers 306*a-b*. For example, the pump 304 can be in fluid communication with the air chamber 306*b* to control inflation and deflation of the air chamber 306*b* as well as detect user signals for a user located over the air chamber 306*b* such as bed presence, sleep state, movement, and biometric signals while the second pump is in fluid communication with the air chamber 306*a* to control inflation and deflation of the air chamber 306*a* as well as detect user signals for a user located over the air chamber 306*a*.

As another example, the bed 302 can include one or more pressure sensitive pads or surface portions that are operable to detect movement, including user presence, user motion, respiration, and heart rate. For example, a first pressure sensitive pad can be incorporated into a surface of the bed 302 over a left portion of the bed 302, where a first user would normally be located during sleep, and a second pressure sensitive pad can be incorporated into the surface of the bed 302 over a right portion of the bed 302, where a second user would normally be located during sleep. The movement detected by the one or more pressure sensitive pads or surface portions can be used by control circuitry 334 to identify user sleep state, bed presence, or biometric signals.

In some implementations, information detected by the bed (e.g., motion information) is processed by control circuitry 334 (e.g., control circuitry 334 integrated with the pump 304) and provided to one or more user devices such as a user device 310 for presentation to the user 308 or to other users. In the example depicted in FIG. 3, the user device 310 is a tablet device; however, in some implementations, the user device 310 can be a personal computer, a smart phone, a smart television (e.g., a television 312), or other user device capable of wired or wireless communication with the control circuitry 334. The user device 310 can be in communication with control circuitry 334 of the bed 302 through a network or through direct point-to-point communication. For example, the control circuitry 334 can be connected to a LAN (e.g., through a Wi-Fi router) and communicate with the user device 310 through the LAN. As another example, the control circuitry 334 and the user device 310 can both connect to the Internet and communicate through the Internet. For example, the control circuitry 334 can connect to the Internet through a WiFi router and the user device 310 can connect to the Internet through communication with a cellular communication system. As another example, the control circuitry 334 can communicate directly with the user device 310 through a wireless communication protocol such as Bluetooth. As yet another example, the control circuitry 334 can communicate with the user device 310 through a wireless communication protocol such as ZigBee, Z-Wave, infrared, or another wireless communication protocol suitable for the application. As another example, the control circuitry 334 can communicate with the user device 310 through a wired connection such as, for example, a USB connector, serial/RS232, or another wired connection suitable for the application.

The user device 310 can display a variety of information and statistics related to sleep, or user 308's interaction with the bed 302. For example, a user interface displayed by the user device 310 can present information including amount of sleep for the user 308 over a period of time (e.g., a single evening, a week, a month, etc.) amount of deep sleep, ratio of deep sleep to restless sleep, time lapse between the user 308 getting into bed and the user 308 falling asleep, total amount of time spent in the bed 302 for a given period of time, heart rate for the user 308 over a period of time, respiration rate for the user 308 over a period of time, or other information related to user interaction with the bed 302 by the user 308 or one or more other users of the bed 302. In some implementations, information for multiple users can be presented on the user device 310, for example information for a first user positioned over the air chamber **306*a* can be presented along with information for a second user positioned over the air chamber 306*b*. In some implementations, the information presented on the user device 310 can vary according to the age of the user 308. For example, the information presented on the user device 310 can evolve with the age of the user 308 such that different information is presented on the user device 310 as the user 308** ages as a child or an adult.

The user device 310 can also be used as an interface for the control circuitry 334 of the bed 302 to allow the user 308 to enter information. The information entered by the user 308 can be used by the control circuitry 334 to provide better information to the user or to various control signals for controlling functions of the bed 302 or other devices. For example, the user can enter information such as weight, height, and age and the control circuitry 334 can use this information to provide the user 308 with a comparison of the user's tracked sleep information to sleep information of other people having similar weights, heights, and/or ages as the user 308. As another example, the user 308 can use the user device 310 as an interface for controlling air pressure of the air chambers **306*a* and 306*b*, for controlling various recline or incline positions of the bed 302, for controlling temperature of one or more surface temperature control devices of the bed 302, or for allowing the control circuitry 334** to generate control signals for other devices (as described in greater detail below).

In some implementations, control circuitry 334 of the bed 302 (e.g., control circuitry 334 integrated into the pump 304) can communicate with other first, second, or third party devices or systems in addition to or instead of the user device 310. For example, the control circuitry 334 can communicate with the television 312, a lighting system 314, a thermostat 316, a security system 318, or other house hold devices such as an oven 322, a coffee maker 324, a lamp 326, and a nightlight 328. Other examples of devices and/or systems that the control circuitry 334 can communicate with include a system for controlling window blinds 330, one or more devices for detecting or controlling the states of one or more doors 332 (such as detecting if a door is open, detecting if a door is locked, or automatically locking a door), and a system for controlling a garage door 320 (e.g., control circuitry 334 integrated with a garage door opener for identifying an open or closed state of the garage door 320 and for causing the garage door opener to open or close the garage door 320). Communications between the control circuitry 334 of the bed 302 and other devices can occur through a network (e.g., a LAN or the Internet) or as point-to-point communication (e.g., using Bluetooth, radio communication, or a wired connection). In some implementations, control circuitry 334 of different beds 302 can communicate with different sets of devices. For example, a kid bed may not communicate with and/or control the same devices as an adult bed. In some embodiments, the bed 302 can evolve with the age of the user such that the control circuitry 334 of the bed 302 communicates with different devices as a function of age of the user.

The control circuitry 334 can receive information and inputs from other devices/systems and use the received information and inputs to control actions of the bed 302 or other devices. For example, the control circuitry 334 can receive information from the thermostat 316 indicating a current environmental temperature for a house or room in which the bed 302 is located. The control circuitry 334 can use the received information (along with other information) to determine if a temperature of all or a portion of the surface of the bed 302 should be raised or lowered. The control circuitry 334 can then cause a heating or cooling mechanism of the bed 302 to raise or lower the temperature of the surface of the bed 302. For example, the user 308 can indicate a desired sleeping temperature of 74 degrees while a second user of the bed 302 indicates a desired sleeping temperature of 72 degrees. The thermostat 316 can indicate to the control circuitry 334 that the current temperature of the bedroom is 72 degrees. The control circuitry 334 can identify that the user 308 has indicated a desired sleeping temperature of 74 degrees, and send control signals to a heating pad located on the user 308's side of the bed to raise the temperature of the portion of the surface of the bed 302 where the user 308 is located to raise the temperature of the user 308's sleeping surface to the desired temperature.

The control circuitry 334 can also generate control signals controlling other devices and propagate the control signals to the other devices. In some implementations, the control signals are generated based on information collected by the control circuitry 334, including information related to user interaction with the bed 302 by the user 308 and/or one or more other users. In some implementations, information collected from one or more other devices other than the bed 302 are used when generating the control signals. For example, information relating to environmental occurrences (e.g., environmental temperature, environmental noise level, and environmental light level), time of day, time of year, day of the week, or other information can be used when generating control signals for various devices in communication with the control circuitry 334 of the bed 302. For example, information on the time of day can be combined with information relating to movement and bed presence of the user 308 to generate control signals for the lighting system 314. In some implementations, rather than or in addition to providing control signals for one or more other devices, the control circuitry 334 can provide collected information (e.g., information related to user movement, bed presence, sleep state, or biometric signals for the user 308) to one or more other devices to allow the one or more other devices to utilize the collected information when generating control signals. For example, control circuitry 334 of the bed 302 can provide information relating to user interactions with the bed 302 by the user 308 to a central controller (not shown) that can use the provided information to generate control signals for various devices, including the bed 302.

Still referring to FIG. 3, the control circuitry 334 of the bed 302 can generate control signals for controlling actions of other devices, and transmit the control signals to the other devices in response to information collected by the control circuitry 334, including bed presence of the user 308, sleep state of the user 308, and other factors. For example, control circuitry 334 integrated with the pump 304 can detect a feature of a mattress of the bed 302, such as an increase in pressure in the air chamber **306*b*, and use this detected increase in air pressure to determine that the user 308 is present on the bed 302. In some implementations, the control circuitry 334 can identify a heart rate or respiratory rate for the user 308 to identify that the increase in pressure is due to a person sitting, laying, or otherwise resting on the bed 302 rather than an inanimate object (such as a suitcase) having been placed on the bed 302. In some implementations, the information indicating user bed presence is combined with other information to identify a current or future likely state for the user 308. For example, a detected user bed presence at 11:00 am can indicate that the user is sitting on the bed (e.g., to tie her shoes, or to read a book) and does not intend to go to sleep, while a detected user bed presence at 10:00 pm can indicate that the user 308 is in bed for the evening and is intending to fall asleep soon. As another example, if the control circuitry 334 detects that the user 308 has left the bed 302 at 6:30 am (e.g., indicating that the user 308 has woken up for the day), and then later detects user bed presence of the user 308 at 7:30 am, the control circuitry 334 can use this information that the newly detected user bed presence is likely temporary (e.g., while the user 308 ties her shoes before heading to work) rather than an indication that the user 308 is intending to stay on the bed 302** for an extended period.

In some implementations, the control circuitry 334 is able to use collected information (including information related to user interaction with the bed 302 by the user 308, as well as environmental information, time information, and input received from the user) to identify use patterns for the user 308. For example, the control circuitry 334 can use information indicating bed presence and sleep states for the user 308 collected over a period of time to identify a sleep pattern for the user. For example, the control circuitry 334 can identify that the user 308 generally goes to bed between 9:30 pm and 10:00 pm, generally falls asleep between 10:00 pm and 11:00 pm, and generally wakes up between 6:30 am and 6:45 am based on information indicating user presence and biometrics for the user 308 collected over a week. The control circuitry 334 can use identified patterns for a user to better process and identify user interactions with the bed 302 by the user 308.

For example, given the above example user bed presence, sleep, and wake patterns for the user 308, if the user 308 is detected as being on the bed at 3:00 pm, the control circuitry 334 can determine that the user's presence on the bed is only temporary, and use this determination to generate different control signals than would be generated if the control circuitry 334 determined that the user 308 was in bed for the evening. As another example, if the control circuitry 334 detects that the user 308 has gotten out of bed at 3:00 am, the control circuitry 334 can use identified patterns for the user 308 to determine that the user has only gotten up temporarily (for example, to use the rest room, or get a glass of water) and is not up for the day. By contrast, if the control circuitry 334 identifies that the user 308 has gotten out of the bed 302 at 6:40 am, the control circuitry 334 can determine that the user is up for the day and generate a different set of control signals than those that would be generated if it were determined that the user 308 were only getting out of bed temporarily (as would be the case when the user 308 gets out of the bed 302 at 3:00 am). For other users 308, getting out of the bed 302 at 3:00 am can be the normal wake-up time, which the control circuitry 334 can learn and respond to accordingly.

As described above, the control circuitry 334 for the bed 302 can generate control signals for control functions of various other devices. The control signals can be generated, at least in part, based on detected interactions by the user 308 with the bed 302, as well as other information including time, date, temperature, etc. For example, the control circuitry 334 can communicate with the television 312, receive information from the television 312, and generate control signals for controlling functions of the television 312. For example, the control circuitry 334 can receive an indication from the television 312 that the television 312 is currently on. If the television 312 is located in a different room from the bed 302, the control circuitry 334 can generate a control signal to turn the television 312 off upon making a determination that the user 308 has gone to bed for the evening. For example, if bed presence of the user 308 on the bed 302 is detected during a particular time range (e.g., between 8:00 pm and 7:00 am) and persists for longer than a threshold period of time (e.g., 10 minutes) the control circuitry 334 can use this information to determine that the user 308 is in bed for the evening. If the television 312 is on (as indicated by communications received by the control circuitry 334 of the bed 302 from the television 312) the control circuitry 334 can generate a control signal to turn the television 312 off. The control signals can then be transmitted to the television (e.g., through a directed communication link between the television 312 and the control circuitry 334 or through a network). As another example, rather than turning off the television 312 in response to detection of user bed presence, the control circuitry 334 can generate a control signal that causes the volume of the television 312 to be lowered by a pre-specified amount.

As another example, upon detecting that the user 308 has left the bed 302 during a specified time range (e.g., between 6:00 am and 8:00 am) the control circuitry 334 can generate control signals to cause the television 312 to turn on and tune to a pre-specified channel (e.g., the user 308 has indicated a preference for watching the morning news upon getting out of bed in the morning). The control circuitry 334 can generate the control signal and transmit the signal to the television 312 to cause the television 312 to turn on and tune to the desired station (which could be stored at the control circuitry 334, the television 312, or another location). As another example, upon detecting that the user 308 has gotten up for the day, the control circuitry 334 can generate and transmit control signals to cause the television 312 to turn on and begin playing a previously recorded program from a digital video recorder (DVR) in communication with the television 312.

As another example, if the television 312 is in the same room as the bed 302, the control circuitry 334 does not cause the television 312 to turn off in response to detection of user bed presence. Rather, the control circuitry 334 can generate and transmit control signals to cause the television 312 to turn off in response to determining that the user 308 is asleep. For example, the control circuitry 334 can monitor biometric signals of the user 308 (e.g., motion, heart rate, respiration rate) to determine that the user 308 has fallen asleep. Upon detecting that the user 308 is sleeping, the control circuitry 334 generates and transmits a control signal to turn the television 312 off. As another example, the control circuitry 334 can generate the control signal to turn off the television 312 after a threshold period of time after the user 308 has fallen asleep (e.g., 10 minutes after the user has fallen asleep). As another example, the control circuitry 334 generates control signals to lower the volume of the television 312 after determining that the user 308 is asleep.

As yet another example, the control circuitry 334 generates and transmits a control signal to cause the television to gradually lower in volume over a period of time and then turn off in response to determining that the user 308 is asleep.

In some implementations, the control circuitry 334 can similarly interact with other media devices, such as computers, tablets, smart phones, stereo systems, etc. For example, upon detecting that the user 308 is asleep, the control circuitry 334 can generate and transmit a control signal to the user device 310 to cause the user device 310 to turn off, or turn down the volume on a video or audio file being played by the user device 310.

The control circuitry 334 can additionally communicate with the lighting system 314, receive information from the lighting system 314, and generate control signals for controlling functions of the lighting system 314. For example, upon detecting user bed presence on the bed 302 during a certain time frame (e.g., between 8:00 pm and 7:00 am) that lasts for longer than a threshold period of time (e.g., 10 minutes) the control circuitry 334 of the bed 302 can determine that the user 308 is in bed for the evening. In response to this determination, the control circuitry 334 can generate control signals to cause lights in one or more rooms other than the room in which the bed 302 is located to switch off. The control signals can then be transmitted to the lighting system 314 and executed by the lighting system 314 to cause the lights in the indicated rooms to shut off For example, the control circuitry 334 can generate and transmit control signals to turn off lights in all common rooms, but not in other bedrooms. As another example, the control signals generated by the control circuitry 334 can indicate that lights in all rooms other than the room in which the bed 302 is located are to be turned off, while one or more lights located outside of the house containing the bed 302 are to be turned on, in response to determining that the user 308 is in bed for the evening. Additionally, the control circuitry 334 can generate and transmit control signals to cause the nightlight 328 to turn on in response to determining user 308 bed presence or whether the user 308 is asleep. As another example, the control circuitry 334 can generate first control signals for turning off a first set of lights (e.g., lights in common rooms) in response to detecting user bed presence, and second control signals for turning off a second set of lights (e.g., lights in the room in which the bed 302 is located) in response to detecting that the user 308 is asleep.

In some implementations, in response to determining that the user 308 is in bed for the evening, the control circuitry 334 of the bed 302 can generate control signals to cause the lighting system 314 to implement a sunset lighting scheme in the room in which the bed 302 is located. A sunset lighting scheme can include, for example, dimming the lights (either gradually over time, or all at once) in combination with changing the color of the light in the bedroom environment, such as adding an amber hue to the lighting in the bedroom. The sunset lighting scheme can help to put the user 308 to sleep when the control circuitry 334 has determined that the user 308 is in bed for the evening.

The control circuitry 334 can also be configured to implement a sunrise lighting scheme when the user 308 wakes up in the morning. The control circuitry 334 can determine that the user 308 is awake for the day, for example, by detecting that the user 308 has gotten off of the bed 302 (i.e., is no longer present on the bed 302) during a specified time frame (e.g., between 6:00 am and 8:00 am). As another example, the control circuitry 334 can monitor movement, heart rate, respiratory rate, or other biometric signals of the user 308 to determine that the user 308 is awake even though the user 308 has not gotten out of bed. If the control circuitry 334 detects that the user is awake during a specified time frame, the control circuitry 334 can determine that the user 308 is awake for the day. The specified time frame can be, for example, based on previously recorded user bed presence information collected over a period of time (e.g., two weeks) that indicates that the user 308 usually wakes up for the day between 6:30 am and 7:30 am. In response to the control circuitry 334 determining that the user 308 is awake, the control circuitry 334 can generate control signals to cause the lighting system 314 to implement the sunrise lighting scheme in the bedroom in which the bed 302 is located. The sunrise lighting scheme can include, for example, turning on lights (e.g., the lamp 326, or other lights in the bedroom). The sunrise lighting scheme can further include gradually increasing the level of light in the room where the bed 302 is located (or in one or more other rooms). The sunrise lighting scheme can also include only turning on lights of specified colors. For example, the sunrise lighting scheme can include lighting the bedroom with blue light to gently assist the user 308 in waking up and becoming active.

In some implementations, the control circuitry 334 can generate different control signals for controlling actions of one or more components, such as the lighting system 314, depending on a time of day that user interactions with the bed 302 are detected. For example, the control circuitry 334 can use historical user interaction information for interactions between the user 308 and the bed 302 to determine that the user 308 usually falls asleep between 10:00 pm and 11:00 pm and usually wakes up between 6:30 am and 7:30 am on weekdays. The control circuitry 334 can use this information to generate a first set of control signals for controlling the lighting system 314 if the user 308 is detected as getting out of bed at 3:00 am and to generate a second set of control signals for controlling the lighting system 314 if the user 308 is detected as getting out of bed after 6:30 am. For example, if the user 308 gets out of bed prior to 6:30 am, the control circuitry 334 can turn on lights that guide the user 308's route to a restroom. As another example, if the user 308 gets out of bed prior to 6:30 am, the control circuitry 334 can turn on lights that guide the user 308's route to the kitchen (which can include, for example, turning on the nightlight 328, turning on under bed lighting, or turning on the lamp 326).

As another example, if the user 308 gets out of bed after 6:30 am, the control circuitry 334 can generate control signals to cause the lighting system 314 to initiate a sunrise lighting scheme, or to turn on one or more lights in the bedroom and/or other rooms. In some implementations, if the user 308 is detected as getting out of bed prior to a specified morning rise time for the user 308, the control circuitry 334 causes the lighting system 314 to turn on lights that are dimmer than lights that are turned on by the lighting system 314 if the user 308 is detected as getting out of bed after the specified morning rise time. Causing the lighting system 314 to only turn on dim lights when the user 308 gets out of bed during the night (i.e., prior to normal rise time for the user 308) can prevent other occupants of the house from being woken by the lights while still allowing the user 308 to see in order to reach the restroom, kitchen, or another destination within the house.

The historical user interaction information for interactions between the user 308 and the bed 302 can be used to identify user sleep and awake time frames. For example, user bed presence times and sleep times can be determined for a set period of time (e.g., two weeks, a month, etc.). The control circuitry 334 can then identify a typical time range or time frame in which the user 308 goes to bed, a typical time frame for when the user 308 falls asleep, and a typical time frame for when the user 308 wakes up (and in some cases, different time frames for when the user 308 wakes up and when the user 308 actually gets out of bed). In some implementations, buffer time can be added to these time frames. For example, if the user is identified as typically going to bed between 10:00 pm and 10:30 pm, a buffer of a half hour in each direction can be added to the time frame such that any detection of the user getting onto the bed between 9:30 pm and 11:00 pm is interpreted as the user 308 going to bed for the evening. As another example, detection of bed presence of the user 308 starting from a half hour before the earliest typical time that the user 308 goes to bed extending until the typical wake up time (e.g., 6:30 am) for the user can be interpreted as the user going to bed for the evening. For example, if the user typically goes to bed between 10:00 pm and 10:30 pm, if the user's bed presence is sensed at 12:30 am one night, that can be interpreted as the user getting into bed for the evening even though this is outside of the user's typical time frame for going to bed because it has occurred prior to the user's normal wake up time. In some implementations, different time frames are identified for different times of the year (e.g., earlier bed time during winter vs. summer) or at different times of the week (e.g., user wakes up earlier on weekdays than on weekends).

The control circuitry 334 can distinguish between the user 308 going to bed for an extended period (such as for the night) as opposed to being present on the bed 302 for a shorter period (such as for a nap) by sensing duration of presence of the user 308. In some examples, the control circuitry 334 can distinguish between the user 308 going to bed for an extended period (such as for the night) as opposed to going to bed for a shorter period (such as for a nap) by sensing duration of sleep of the user 308. For example, the control circuitry 334 can set a time threshold whereby if the user 308 is sensed on the bed 302 for longer than the threshold, the user 308 is considered to have gone to bed for the night. In some examples, the threshold can be about 2 hours, whereby if the user 308 is sensed on the bed 302 for greater than 2 hours, the control circuitry 334 registers that as an extended sleep event. In other examples, the threshold can be greater than or less than two hours.

The control circuitry 334 can detect repeated extended sleep events to determine a typical bed time range of the user 308 automatically, without requiring the user 308 to enter a bed time range. This can allow the control circuitry 334 to accurately estimate when the user 308 is likely to go to bed for an extended sleep event, regardless of whether the user 308 typically goes to bed using a traditional sleep schedule or a non-traditional sleep schedule. The control circuitry 334 can then use knowledge of the bed time range of the user 308 to control one or more components (including components of the bed 302 and/or non-bed peripherals) differently based on sensing bed presence during the bed time range or outside of the bed time range.

In some examples, the control circuitry 334 can automatically determine the bed time range of the user 308 without requiring user inputs. In some examples, the control circuitry 334 can determine the bed time range of the user 308 automatically and in combination with user inputs. In some examples, the control circuitry 334 can set the bed time range directly according to user inputs. In some examples, the control circuitry 334 can associate different bed times with different days of the week. In each of these examples, the control circuitry 334 can control one or more components (such as the lighting system 314, the thermostat 316, the security system 318, the oven 322, the coffee maker 324, the lamp 326, and the nightlight 328), as a function of sensed bed presence and the bed time range.

The control circuitry 334 can additionally communicate with the thermostat 316, receive information from the thermostat 316, and generate control signals for controlling functions of the thermostat 316. For example, the user 308 can indicate user preferences for different temperatures at different times, depending on the sleep state or bed presence of the user 308. For example, the user 308 may prefer an environmental temperature of 72 degrees when out of bed, 70 degrees when in bed but awake, and 68 degrees when sleeping. The control circuitry 334 of the bed 302 can detect bed presence of the user 308 in the evening and determine that the user 308 is in bed for the night. In response to this determination, the control circuitry 334 can generate control signals to cause the thermostat to change the temperature to 70 degrees. The control circuitry 334 can then transmit the control signals to the thermostat 316. Upon detecting that the user 308 is in bed during the bed time range or asleep, the control circuitry 334 can generate and transmit control signals to cause the thermostat 316 to change the temperature to 68. The next morning, upon determining that the user is awake for the day (e.g., the user 308 gets out of bed after 6:30 am) the control circuitry 334 can generate and transmit control circuitry 334 to cause the thermostat to change the temperature to 72 degrees.

In some implementations, the control circuitry 334 can similarly generate control signals to cause one or more heating or cooling elements on the surface of the bed 302 to change temperature at various times, either in response to user interaction with the bed 302 or at various pre-programmed times. For example, the control circuitry 334 can activate a heating element to raise the temperature of one side of the surface of the bed 302 to 73 degrees when it is detected that the user 308 has fallen asleep. As another example, upon determining that the user 308 is up for the day, the control circuitry 334 can turn off a heating or cooling element. As yet another example, the user 308 can pre-program various times at which the temperature at the surface of the bed should be raised or lowered. For example, the user can program the bed 302 to raise the surface temperature to 76 degrees at 10:00 pm, and lower the surface temperature to 68 degrees at 11:30 pm.

In some implementations, in response to detecting user bed presence of the user 308 and/or that the user 308 is asleep, the control circuitry 334 can cause the thermostat 316 to change the temperature in different rooms to different values. For example, in response to determining that the user 308 is in bed for the evening, the control circuitry 334 can generate and transmit control signals to cause the thermostat 316 to set the temperature in one or more bedrooms of the house to 72 degrees and set the temperature in other rooms to 67 degrees.

The control circuitry 334 can also receive temperature information from the thermostat 316 and use this temperature information to control functions of the bed 302 or other devices. For example, as discussed above, the control circuitry 334 can adjust temperatures of heating elements included in the bed 302 in response to temperature information received from the thermostat 316.

In some implementations, the control circuitry 334 can generate and transmit control signals for controlling other temperature control systems. For example, in response to determining that the user 308 is awake for the day, the control circuitry 334 can generate and transmit control signals for causing floor heating elements to activate. For example, the control circuitry 334 can cause a floor heating system for a master bedroom to turn on in response to determining that the user 308 is awake for the day.

The control circuitry 334 can additionally communicate with the security system 318, receive information from the security system 318, and generate control signals for controlling functions of the security system 318. For example, in response to detecting that the user 308 in is bed for the evening, the control circuitry 334 can generate control signals to cause the security system to engage or disengage security functions. The control circuitry 334 can then transmit the control signals to the security system 318 to cause the security system 318 to engage. As another example, the control circuitry 334 can generate and transmit control signals to cause the security system 318 to disable in response to determining that the user 308 is awake for the day (e.g., user 308 is no longer present on the bed 302 after 6:00 am). In some implementations, the control circuitry 334 can generate and transmit a first set of control signals to cause the security system 318 to engage a first set of security features in response to detecting user bed presence of the user 308, and can generate and transmit a second set of control signals to cause the security system 318 to engage a second set of security features in response to detecting that the user 308 has fallen asleep.

In some implementations, the control circuitry 334 can receive alerts from the security system 318 (and/or a cloud service associated with the security system 318) and indicate the alert to the user 308. For example, the control circuitry 334 can detect that the user 308 is in bed for the evening and in response, generate and transmit control signals to cause the security system 318 to engage or disengage. The security system can then detect a security breach (e.g., someone has opened the door 332 without entering the security code, or someone has opened a window when the security system 318 is engaged). The security system 318 can communicate the security breach to the control circuitry 334 of the bed 302. In response to receiving the communication from the security system 318, the control circuitry 334 can generate control signals to alert the user 308 to the security breach. For example, the control circuitry 334 can cause the bed 302 to vibrate. As another example, the control circuitry 334 can cause portions of the bed 302 to articulate (e.g., cause the head section to raise or lower) in order to wake the user 308 and alert the user to the security breach. As another example, the control circuitry 334 can generate and transmit control signals to cause the lamp 326 to flash on and off at regular intervals to alert the user 308 to the security breach. As another example, the control circuitry 334 can alert the user 308 of one bed 302 regarding a security breach in a bedroom of another bed, such as an open window in a kid's bedroom. As another example, the control circuitry 334 can send an alert to a garage door controller (e.g., to close and lock the door). As another example, the control circuitry 334 can send an alert for the security to be disengaged.

The control circuitry 334 can additionally generate and transmit control signals for controlling the garage door 320 and receive information indicating a state of the garage door 320 (i.e., open or closed). For example, in response to determining that the user 308 is in bed for the evening, the control circuitry 334 can generate and transmit a request to a garage door opener or another device capable of sensing if the garage door 320 is open. The control circuitry 334 can request information on the current state of the garage door 320. If the control circuitry 334 receives a response (e.g., from the garage door opener) indicating that the garage door 320 is open, the control circuitry 334 can either notify the user 308 that the garage door is open, or generate a control signal to cause the garage door opener to close the garage door 320. For example, the control circuitry 334 can send a message to the user device 310 indicating that the garage door is open. As another example, the control circuitry 334 can cause the bed 302 to vibrate. As yet another example, the control circuitry 334 can generate and transmit a control signal to cause the lighting system 314 to cause one or more lights in the bedroom to flash to alert the user 308 to check the user device 310 for an alert (in this example, an alert regarding the garage door 320 being open). Alternatively, or additionally, the control circuitry 334 can generate and transmit control signals to cause the garage door opener to close the garage door 320 in response to identifying that the user 308 is in bed for the evening and that the garage door 320 is open. In some implementations, control signals can vary depend on the age of the user 308.

The control circuitry 334 can similarly send and receive communications for controlling or receiving state information associated with the door 332 or the oven 322. For example, upon detecting that the user 308 is in bed for the evening, the control circuitry 334 can generate and transmit a request to a device or system for detecting a state of the door 332. Information returned in response to the request can indicate various states for the door 332 such as open, closed but unlocked, or closed and locked. If the door 332 is open or closed but unlocked, the control circuitry 334 can alert the user 308 to the state of the door, such as in a manner described above with reference to the garage door 320. Alternatively, or in addition to alerting the user 308, the control circuitry 334 can generate and transmit control signals to cause the door 332 to lock, or to close and lock. If the door 332 is closed and locked, the control circuitry 334 can determine that no further action is needed.

Similarly, upon detecting that the user 308 is in bed for the evening, the control circuitry 334 can generate and transmit a request to the oven 322 to request a state of the oven 322 (e.g., on or off). If the oven 322 is on, the control circuitry 334 can alert the user 308 and/or generate and transmit control signals to cause the oven 322 to turn off. If the oven is already off, the control circuitry 334 can determine that no further action is necessary. In some implementations, different alerts can be generated for different events. For example, the control circuitry 334 can cause the lamp 326 (or one or more other lights, via the lighting system 314) to flash in a first pattern if the security system 318 has detected a breach, flash in a second pattern if garage door 320 is on, flash in a third pattern if the door 332 is open, flash in a fourth pattern if the oven 322 is on, and flash in a fifth pattern if another bed has detected that a user of that bed has gotten up (e.g., that a child of the user 308 has gotten out of bed in the middle of the night as sensed by a sensor in the bed 302 of the child). Other examples of alerts that can be processed by the control circuitry 334 of the bed 302 and communicated to the user include a smoke detector detecting smoke (and communicating this detection of smoke to the control circuitry 334), a carbon monoxide tester detecting carbon monoxide, a heater malfunctioning, or an alert from any other device capable of communicating with the control circuitry 334 and detecting an occurrence that should be brought to the user 308's attention.

The control circuitry 334 can also communicate with a system or device for controlling a state of the window blinds 330. For example, in response to determining that the user 308 is in bed for the evening, the control circuitry 334 can generate and transmit control signals to cause the window blinds 330 to close. As another example, in response to determining that the user 308 is up for the day (e.g., user has gotten out of bed after 6:30 am) the control circuitry 334 can generate and transmit control signals to cause the window blinds 330 to open. By contrast, if the user 308 gets out of bed prior to a normal rise time for the user 308, the control circuitry 334 can determine that the user 308 is not awake for the day and does not generate control signals for causing the window blinds 330 to open. As yet another example, the control circuitry 334 can generate and transmit control signals that cause a first set of blinds to close in response to detecting user bed presence of the user 308 and a second set of blinds to close in response to detecting that the user 308 is asleep.

The control circuitry 334 can generate and transmit control signals for controlling functions of other household devices in response to detecting user interactions with the bed 302. For example, in response to determining that the user 308 is awake for the day, the control circuitry 334 can generate and transmit control signals to the coffee maker 324 to cause the coffee maker 324 to begin brewing coffee. As another example, the control circuitry 334 can generate and transmit control signals to the oven 322 to cause the oven to begin preheating (for users that like fresh baked bread in the morning). As another example, the control circuitry 334 can use information indicating that the user 308 is awake for the day along with information indicating that the time of year is currently winter and/or that the outside temperature is below a threshold value to generate and transmit control signals to cause a car engine block heater to turn on.

As another example, the control circuitry 334 can generate and transmit control signals to cause one or more devices to enter a sleep mode in response to detecting user bed presence of the user 308, or in response to detecting that the user 308 is asleep. For example, the control circuitry 334 can generate control signals to cause a mobile phone of the user 308 to switch into sleep mode. The control circuitry 334 can then transmit the control signals to the mobile phone. Later, upon determining that the user 308 is up for the day, the control circuitry 334 can generate and transmit control signals to cause the mobile phone to switch out of sleep mode.

In some implementations, the control circuitry 334 can communicate with one or more noise control devices. For example, upon determining that the user 308 is in bed for the evening, or that the user 308 is asleep, the control circuitry 334 can generate and transmit control signals to cause one or more noise cancelation devices to activate. The noise cancelation devices can, for example, be included as part of the bed 302 or located in the bedroom with the bed 302. As another example, upon determining that the user 308 is in bed for the evening or that the user 308 is asleep, the control circuitry 334 can generate and transmit control signals to turn the volume on, off, up, or down, for one or more sound generating devices, such as a stereo system radio, computer, tablet, etc.

Additionally, functions of the bed 302 are controlled by the control circuitry 334 in response to user interactions with the bed 302. For example, the bed 302 can include an adjustable foundation and an articulation controller configured to adjust the position of one or more portions of the bed 302 by adjusting the adjustable foundation that supports the bed. For example, the articulation controller can adjust the bed 302 from a flat position to a position in which a head portion of a mattress of the bed 302 is inclined upward (e.g., to facilitate a user sitting up in bed and/or watching television). In some implementations, the bed 302 includes multiple separately articulable sections. For example, portions of the bed corresponding to the locations of the air chambers **306*a* and 306*b* can be articulated independently from each other, to allow one person positioned on the bed 302 surface to rest in a first position (e.g., a flat position) while a second person rests in a second position (e.g., a reclining position with the head raised at an angle from the waist). In some implementations, separate positions can be set for two different beds (e.g., two twin beds placed next to each other). The foundation of the bed 302 can include more than one zone that can be independently adjusted. The articulation controller can also be configured to provide different levels of massage to one or more users on the bed 302 or to cause the bed to vibrate to communicate alerts to the user 308** as described above.

The control circuitry 334 can adjust positions (e.g., incline and decline positions for the user 308 and/or an additional user of the bed 302) in response to user interactions with the bed 302. For example, the control circuitry 334 can cause the articulation controller to adjust the bed 302 to a first recline position for the user 308 in response to sensing user bed presence for the user 308. The control circuitry 334 can cause the articulation controller to adjust the bed 302 to a second recline position (e.g., a less reclined, or flat position) in response to determining that the user 308 is asleep. As another example, the control circuitry 334 can receive a communication from the television 312 indicating that the user 308 has turned off the television 312, and in response the control circuitry 334 can cause the articulation controller to adjust the position of the bed 302 to a preferred user sleeping position (e.g., due to the user turning off the television 312 while the user 308 is in bed indicating that the user 308 wishes to go to sleep).

In some implementations, the control circuitry 334 can control the articulation controller so as to wake up one user of the bed 302 without waking another user of the bed 302. For example, the user 308 and a second user of the bed 302 can each set distinct wakeup times (e.g., 6:30 am and 7:15 am respectively). When the wakeup time for the user 308 is reached, the control circuitry 334 can cause the articulation controller to vibrate or change the position of only a side of the bed on which the user 308 is located to wake the user 308 without disturbing the second user. When the wakeup time for the second user is reached, the control circuitry 334 can cause the articulation controller to vibrate or change the position of only the side of the bed on which the second user is located. Alternatively, when the second wakeup time occurs, the control circuitry 334 can utilize other methods (such as audio alarms, or turning on the lights) to wake the second user since the user 308 is already awake and therefore will not be disturbed when the control circuitry 334 attempts to wake the second user.

Still referring to FIG. 3, the control circuitry 334 for the bed 302 can utilize information for interactions with the bed 302 by multiple users to generate control signals for controlling functions of various other devices. For example, the control circuitry 334 can wait to generate control signals for, for example, engaging the security system 318, or instructing the lighting system 314 to turn off lights in various rooms until both the user 308 and a second user are detected as being present on the bed 302. As another example, the control circuitry 334 can generate a first set of control signals to cause the lighting system 314 to turn off a first set of lights upon detecting bed presence of the user 308 and generate a second set of control signals for turning off a second set of lights in response to detecting bed presence of a second user. As another example, the control circuitry 334 can wait until it has been determined that both the user 308 and a second user are awake for the day before generating control signals to open the window blinds 330. As yet another example, in response to determining that the user 308 has left the bed and is awake for the day, but that a second user is still sleeping, the control circuitry 334 can generate and transmit a first set of control signals to cause the coffee maker 324 to begin brewing coffee, to cause the security system 318 to deactivate, to turn on the lamp 326, to turn off the nightlight 328, to cause the thermostat 316 to raise the temperature in one or more rooms to 72 degrees, and to open blinds (e.g., the window blinds 330) in rooms other than the bedroom in which the bed 302 is located. Later, in response to detecting that the second user is no longer present on the bed (or that the second user is awake) the control circuitry 334 can generate and transmit a second set of control signals to, for example, cause the lighting system 314 to turn on one or more lights in the bedroom, to cause window blinds in the bedroom to open, and to turn on the television 312 to a pre-specified channel.

Examples of Data Processing Systems Associated with a Bed

Described here are examples of systems and components that can be used for data processing tasks that are, for example, associated with a bed. In some cases, multiple examples of a particular component or group of components are presented. Some of these examples are redundant and/or mutually exclusive alternatives. Connections between components are shown as examples to illustrate possible network configurations for allowing communication between components. Different formats of connections can be used as technically needed or desired. The connections generally indicate a logical connection that can be created with any technologically feasible format. For example, a network on a motherboard can be created with a printed circuit board, wireless data connections, and/or other types of network connections. Some logical connections are not shown for clarity. For example, connections with power supplies and/or computer readable memory may not be shown for clarities sake, as many or all elements of a particular component may need to be connected to the power supplies and/or computer readable memory.

Figure 4A:
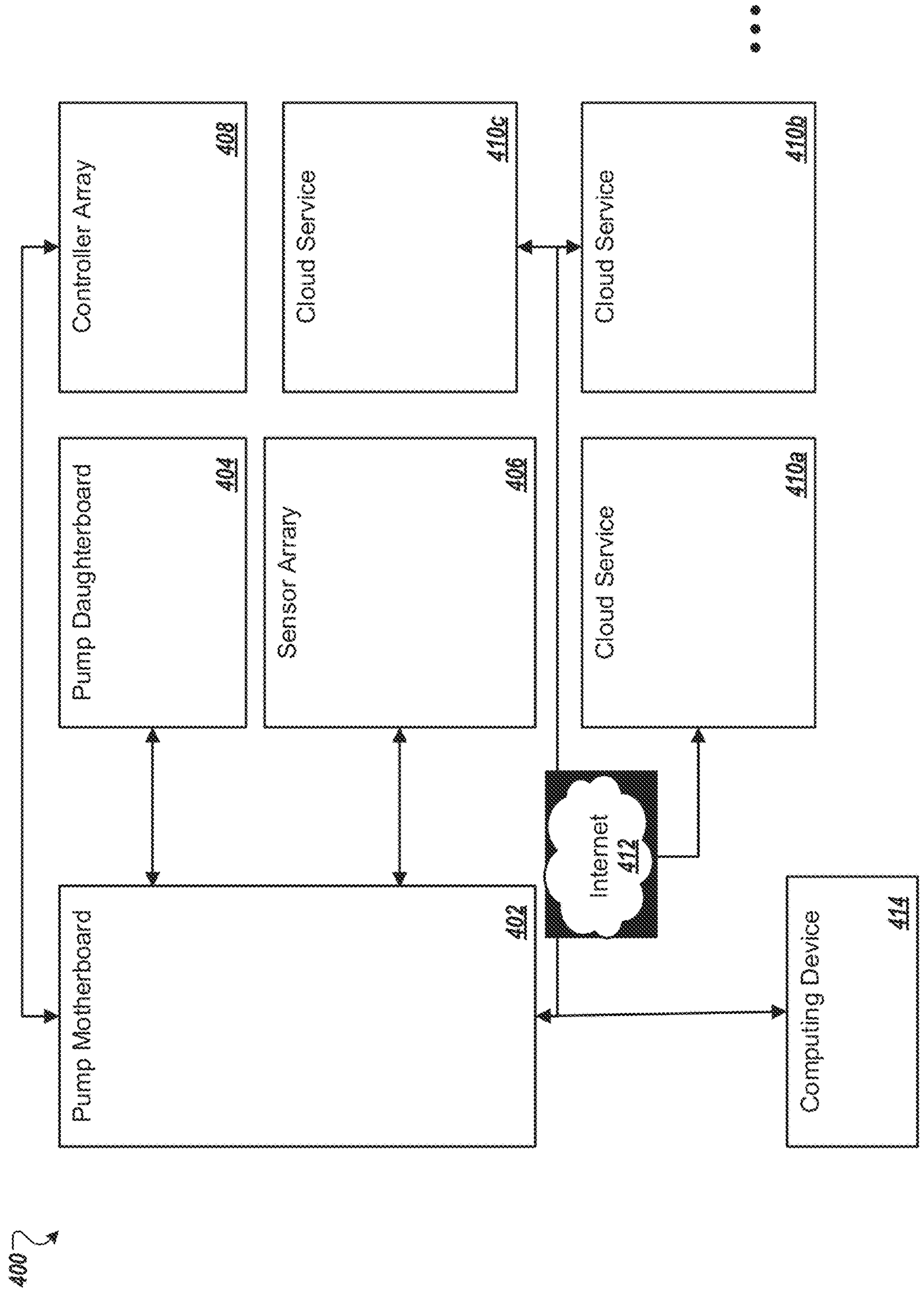
FIGS. 4A and 4B are block diagrams of example data processing systems that can be associated with a bed.

FIG. 4A is a block diagram of an example of a data processing system 400 that can be associated with a bed system, including those described above with respect to FIGS. 1-3. This system 400 includes a pump motherboard 402 and a pump daughterboard 404. The system 400 includes a sensor array 406 that can include one or more sensors configured to sense physical phenomenon of the environment and/or bed, and to report such sensing back to the pump motherboard 402 for, for example, analysis. The system 400 also includes a controller array 408 that can include one or more controllers configured to control logic-controlled devices of the bed and/or environment. The pump motherboard 400 can be in communication with one or more computing devices 414 and one or more cloud services 410 over local networks, the Internet 412, or otherwise as is technically appropriate. Each of these components will be described in more detail, some with multiple example configurations, below.

In this example, a pump motherboard 402 and a pump daughterboard 404 are communicably coupled. They can be conceptually described as a center or hub of the system 400, with the other components conceptually described as spokes of the system 400. In some configurations, this can mean that each of the spoke components communicates primarily or exclusively with the pump motherboard 402. For example, a sensor of the sensor array may not be configured to, or may not be able to, communicate directly with a corresponding controller. Instead, each spoke component can communicate with the motherboard 402. The sensor of the sensor array 406 can report a sensor reading to the motherboard 402, and the motherboard 402 can determine that, in response, a controller of the controller array 408 should adjust some parameters of a logic controlled device or otherwise modify a state of one or more peripheral devices. In one case, if the temperature of the bed is determined to be too hot, the pump motherboard 402 can determine that a temperature controller should cool the bed.

One advantage of a hub-and-spoke network configuration, sometimes also referred to as a star-shaped network, is a reduction in network traffic compared to, for example, a mesh network with dynamic routing. If a particular sensor generates a large, continuous stream of traffic, that traffic may only be transmitted over one spoke of the network to the motherboard 402. The motherboard 402 can, for example, marshal that data and condense it to a smaller data format for retransmission for storage in a cloud service 410. Additionally or alternatively, the motherboard 402 can generate a single, small, command message to be sent down a different spoke of the network in response to the large stream. For example, if the large stream of data is a pressure reading that is transmitted from the sensor array 406 a few times a second, the motherboard 402 can respond with a single command message to the controller array to increase the pressure in an air chamber. In this case, the single command message can be orders of magnitude smaller than the stream of pressure readings.

As another advantage, a hub-and-spoke network configuration can allow for an extensible network that can accommodate components being added, removed, failing, etc. This can allow, for example, more, fewer, or different sensors in the sensor array 406, controllers in the controller array 408, computing devices 414, and/or cloud services 410. For example, if a particular sensor fails or is deprecated by a newer version of the sensor, the system 400 can be configured such that only the motherboard 402 needs to be updated about the replacement sensor. This can allow, for example, product differentiation where the same motherboard 402 can support an entry level product with fewer sensors and controllers, a higher value product with more sensors and controllers, and customer personalization where a customer can add their own selected components to the system 400.

Additionally, a line of air bed products can use the system 400 with different components. In an application in which every air bed in the product line includes both a central logic unit and a pump, the motherboard 402 (and optionally the daughterboard 404) can be designed to fit within a single, universal housing. Then, for each upgrade of the product in the product line, additional sensors, controllers, cloud services, etc., can be added. Design, manufacturing, and testing time can be reduced by designing all products in a product line from this base, compared to a product line in which each product has a bespoke logic control system.

Each of the components discussed above can be realized in a wide variety of technologies and configurations. Below, some examples of each component will be further discussed. In some alternatives, two or more of the components of the system 400 can be realized in a single alternative component; some components can be realized in multiple, separate components; and/or some functionality can be provided by different components.

Figure 4B:
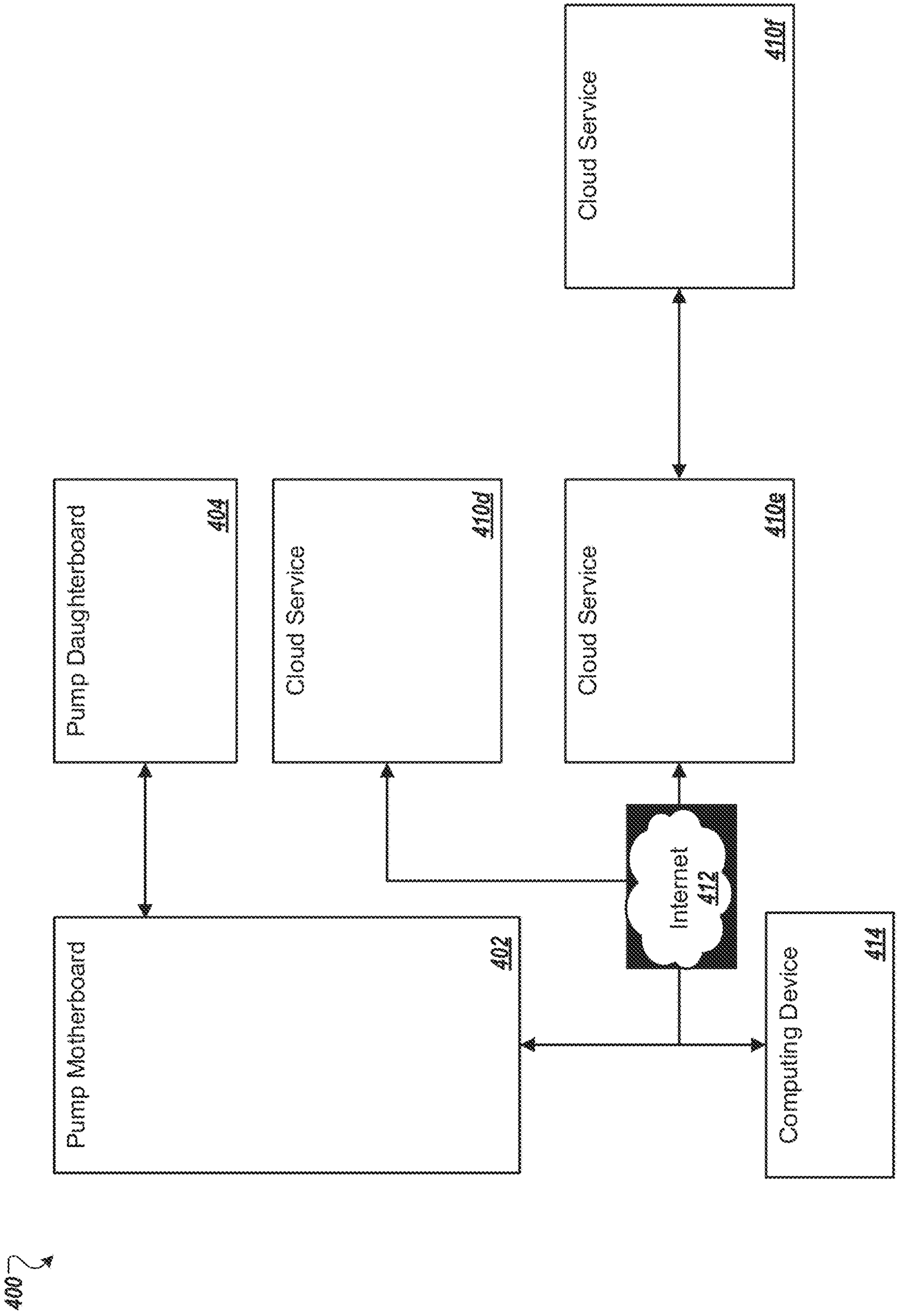

FIG. 4B is a block diagram showing some communication paths of the data processing system 400. As previously described, the motherboard 402 and the pump daughterboard 404 may act as a hub for peripheral devices and cloud services of the system 400. In cases in which the pump daughterboard 404 communicates with cloud services or other components, communications from the pump daughterboard 404 may be routed through the pump motherboard 402. This may allow, for example, the bed to have only a single connection with the internet 412. The computing device 414 may also have a connection to the internet 412, possibly through the same gateway used by the bed and/or possibly through a different gateway (e.g., a cell service provider).

Previously, a number of cloud services 410 were described. As shown in FIG. 4B, some cloud services, such as cloud services 410*d* and 410*e*, may be configured such that the pump motherboard 402 can communicate with the cloud service directly—that is the motherboard 402 may communicate with a cloud service 410 without having to use another cloud service 410 as an intermediary. Additionally or alternatively, some cloud services 410, for example cloud service 410*f*, may only be reachable by the pump motherboard 402 through an intermediary cloud service, for example cloud service 410*e*. While not shown here, some cloud services 410 may be reachable either directly or indirectly by the pump motherboard 402.

Additionally, some or all of the cloud services 410 may be configured to communicate with other cloud services. This communication may include the transfer of data and/or remote function calls according to any technologically appropriate format. For example, one cloud service 410 may request a copy for another cloud service's 410 data, for example, for purposes of backup, coordination, migration, or for performance of calculations or data mining. In another example, many cloud services 410 may contain data that is indexed according to specific users tracked by the user account cloud 410*c* and/or the bed data cloud 410*a*. These cloud services 410 may communicate with the user account cloud 410*c* and/or the bed data cloud 410*a* when accessing data specific to a particular user or bed.

Figure 5:
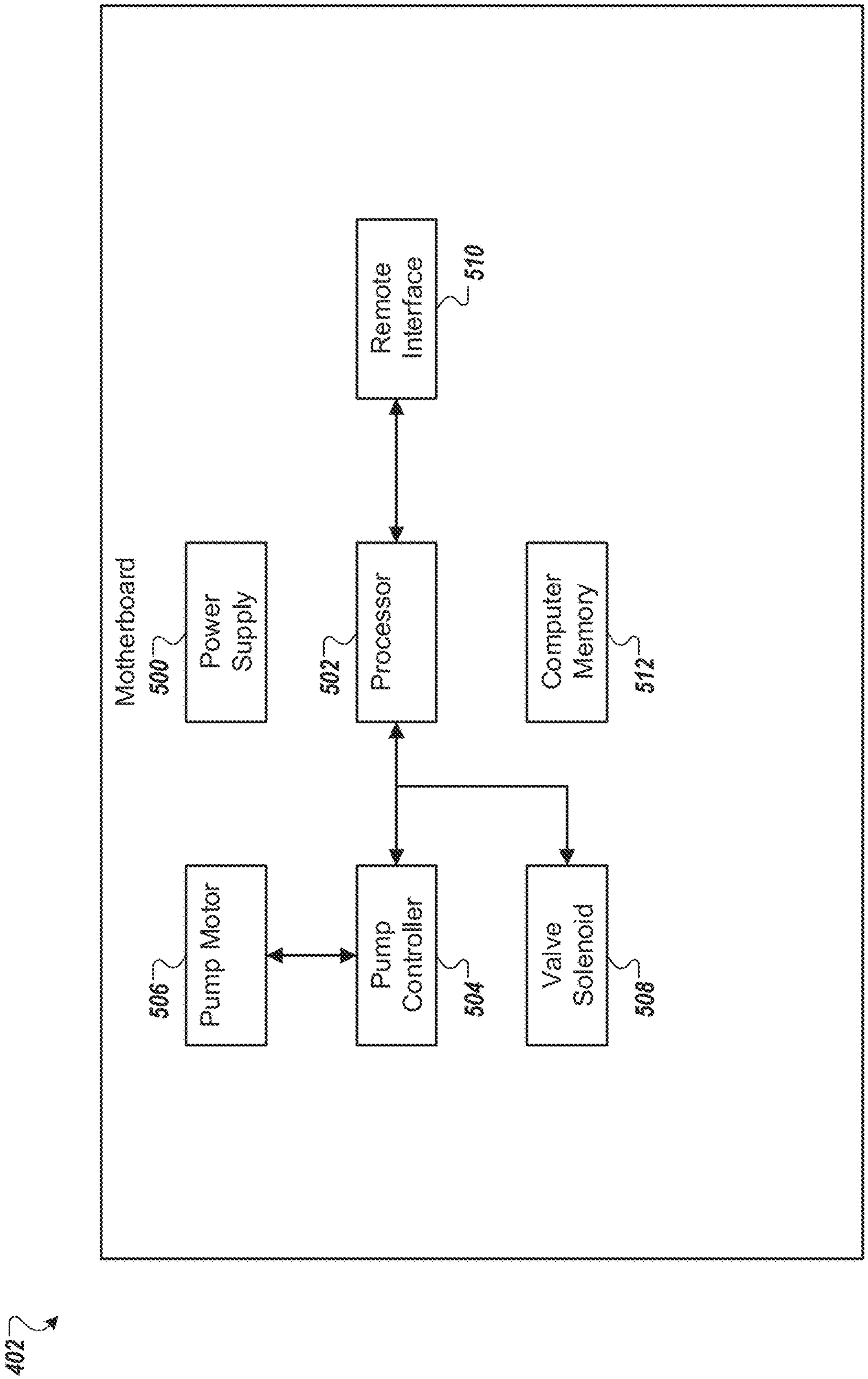
FIGS. 5 and 6 are block diagrams of examples of motherboards that can be used in a data processing system that can be associated with a bed.

FIG. 5 is a block diagram of an example of a motherboard 402 that can be used in a data processing system that can be associated with a bed system, including those described above with respect to FIGS. 1-3. In this example, compared to other examples described below, this motherboard 402 consists of relatively fewer parts and can be limited to provide a relatively limited feature set.

The motherboard includes a power supply 500, a processor 502, and computer memory 512. In general, the power supply includes hardware used to receive electrical power from an outside source and supply it to components of the motherboard 402. The power supply can include, for example, a battery pack and/or wall outlet adapter, an AC to DC converter, a DC to AC converter, a power conditioner, a capacitor bank, and/or one or more interfaces for providing power in the current type, voltage, etc., needed by other components of the motherboard 402.

The processor 502 is generally a device for receiving input, performing logical determinations, and providing output. The processor 502 can be a central processing unit, a microprocessor, general purpose logic circuitry, application-specific integrated circuitry, a combination of these, and/or other hardware for performing the functionality needed.

The memory 512 is generally one or more devices for storing data. The memory 512 can include long term stable data storage (e.g., on a hard disk), short term unstable (e.g., on Random Access Memory) or any other technologically appropriate configuration.

The motherboard 402 includes a pump controller 504 and a pump motor 506. The pump controller 504 can receive commands from the processor 502 and, in response, control the function of the pump motor 506. For example, the pump controller 504 can receive, from the processor 502, a command to increase the pressure of an air chamber by 0.3 pounds per square inch (PSI). The pump controller 504, in response, engages a valve so that the pump motor 506 is configured to pump air into the selected air chamber, and can engage the pump motor 506 for a length of time that corresponds to 0.3 PSI or until a sensor indicates that pressure has been increased by 0.3 PSI. In an alternative configuration, the message can specify that the chamber should be inflated to a target PSI, and the pump controller 504 can engage the pump motor 506 until the target PSI is reached.

A valve solenoid 508 can control which air chamber a pump is connected to. In some cases, the solenoid 508 can be controlled by the processor 502 directly. In some cases, the solenoid 508 can be controlled by the pump controller 504.

A remote interface 510 of the motherboard 402 can allow the motherboard 402 to communicate with other components of a data processing system. For example, the motherboard 402 can be able to communicate with one or more daughterboards, with peripheral sensors, and/or with peripheral controllers through the remote interface 510. The remote interface 510 can provide any technologically appropriate communication interface, including but not limited to multiple communication interfaces such as WiFi, Bluetooth, and copper wired networks.

Figure 6:
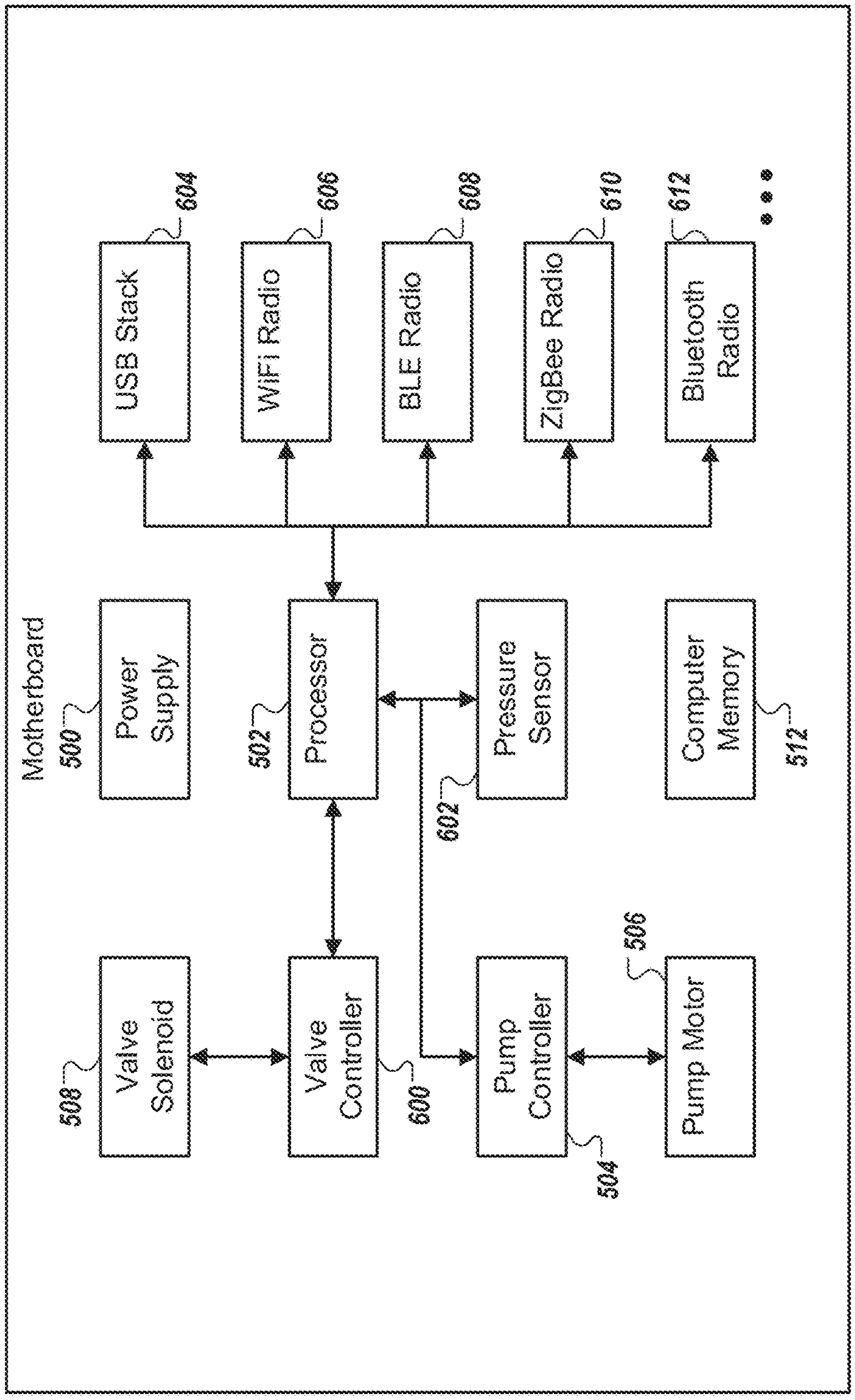

FIG. 6 is a block diagram of an example of a motherboard 402 that can be used in a data processing system that can be associated with a bed system, including those described above with respect to FIGS. 1-3. Compared to the motherboard 402 described with reference to FIG. 5, the motherboard in FIG. 6 can contain more components and provide more functionality in some applications.

In addition to the power supply 500, processor 502, pump controller 504, pump motor 506, and valve solenoid 508, this motherboard 402 is shown with a valve controller 600, a pressure sensor 602, a universal serial bus (USB) stack 604, a WiFi radio 606, a Bluetooth Low Energy (BLE) radio 608, a ZigBee radio 610, a Bluetooth radio 612 and a computer memory 512.

Similar to the way that the pump controller 504 converts commands from the processor 502 into control signals for the pump motor 506, the valve controller 600 can convert commands from the processor 502 into control signals for the valve solenoid 508. In one example, the processor 502 can issue a command to the valve controller 600 to connect the pump to a particular air chamber out of the group of air chambers in an air bed. The valve controller 600 can control the position of the valve solenoid 508 so that the pump is connected to the indicated air chamber.

The pressure sensor 602 can read pressure readings from one or more air chambers of the air bed. The pressure sensor 602 can also preform digital sensor conditioning.

The motherboard 402 can include a suite of network interfaces, including but not limited to those shown here. These network interfaces can allow the motherboard to communicate over a wired or wireless network with any number of devices, including but not limited to peripheral sensors, peripheral controllers, computing devices, and devices and services connected to the Internet 412.

Figure 7:
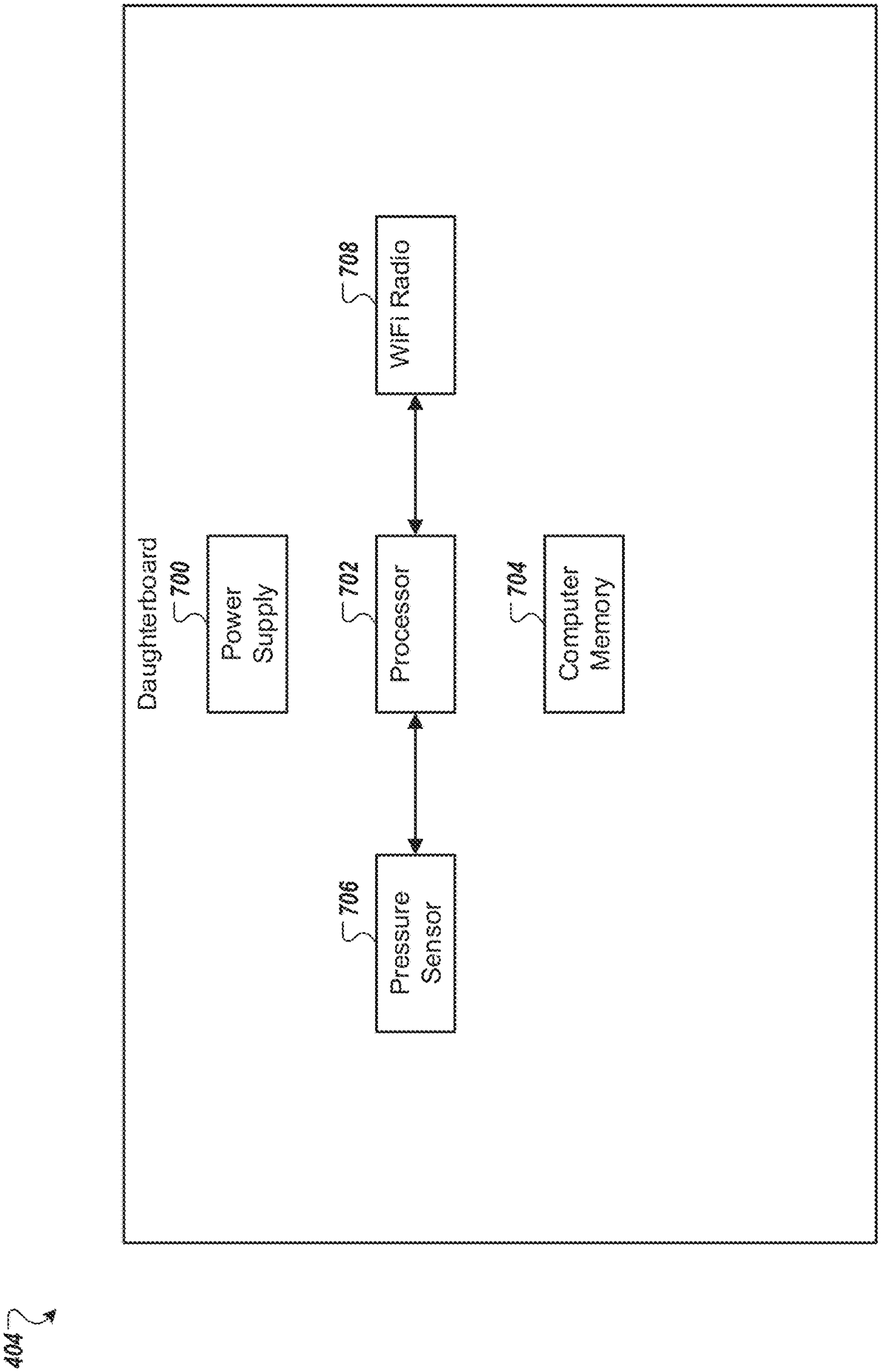
FIG. 7 is a block diagram of an example of a daughterboard that can be used in a data processing system that can be associated with a bed.

FIG. 7 is a block diagram of an example of a daughterboard 404 that can be used in a data processing system that can be associated with a bed system, including those described above with respect to FIGS. 1-3. In some configurations, one or more daughterboards 404 can be connected to the motherboard 402. Some daughterboards 404 can be designed to offload particular and/or compartmentalized tasks from the motherboard 402. This can be advantageous, for example, if the particular tasks are computationally intensive, proprietary, or subject to future revisions. For example, the daughterboard 404 can be used to calculate a particular sleep data metric. This metric can be computationally intensive, and calculating the sleep metric on the daughterboard 404 can free up the resources of the motherboard 402 while the metric is being calculated. Additionally and/or alternatively, the sleep metric can be subject to future revisions. To update the system 400 with the new sleep metric, it is possible that only the daughterboard 404 that calculates that metric need be replaced. In this case, the same motherboard 402 and other components can be used, saving the need to perform unit testing of additional components instead of just the daughterboard 404.

The daughterboard 404 is shown with a power supply 700, a processor 702, computer readable memory 704, a pressure sensor 706, and a WiFi radio 708. The processor can use the pressure sensor 706 to gather information about the pressure of the air chamber or chambers of an air bed. From this data, the processor 702 can perform an algorithm to calculate a sleep metric. In some examples, the sleep metric can be calculated from only the pressure of air chambers. In other examples, the sleep metric can be calculated from one or more other sensors. In an example in which different data is needed, the processor 702 can receive that data from an appropriate sensor or sensors. These sensors can be internal to the daughterboard 404, accessible via the WiFi radio 708, or otherwise in communication with the processor 702. Once the sleep metric is calculated, the processor 702 can report that sleep metric to, for example, the motherboard 402.

Figure 8:
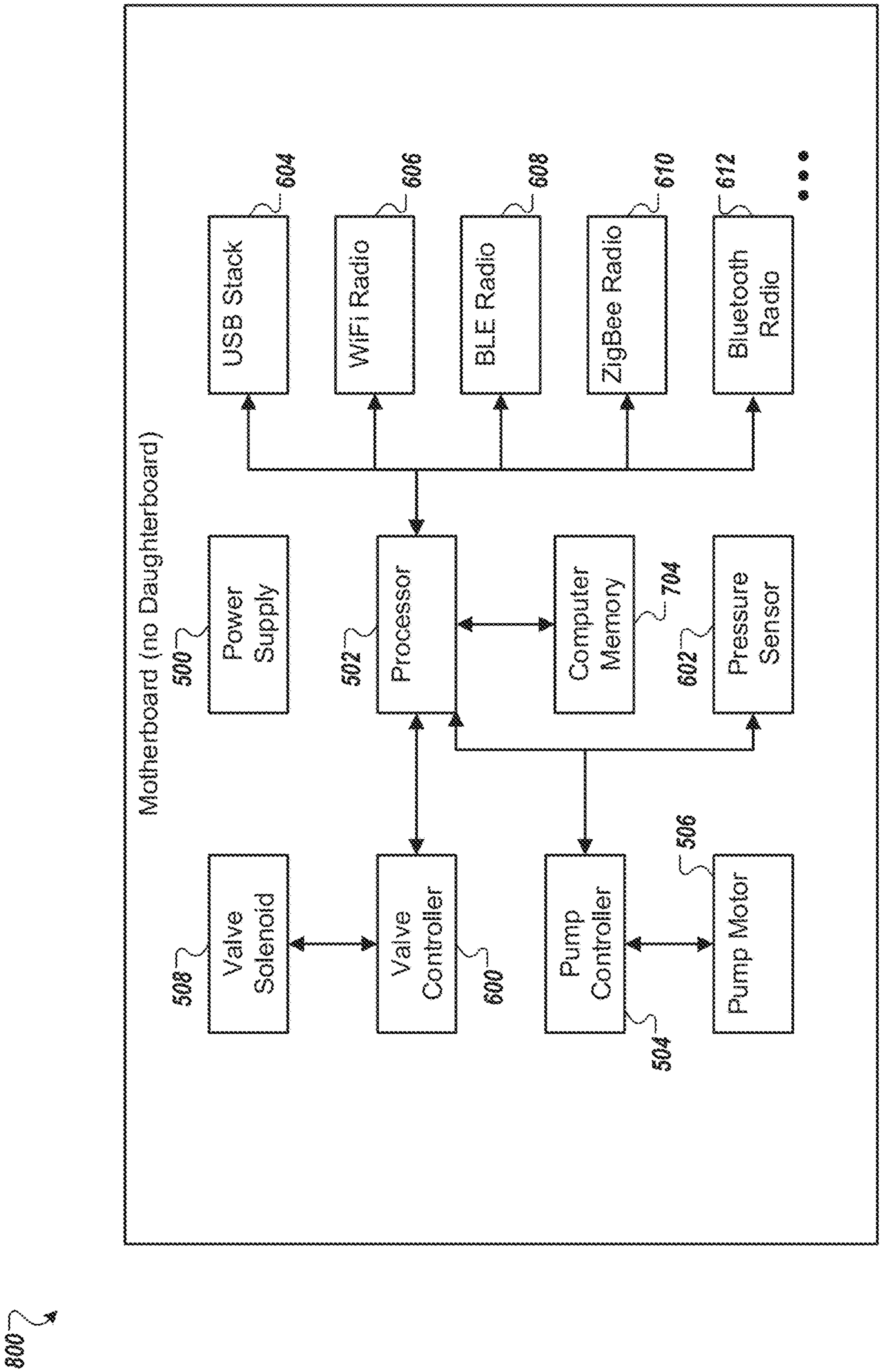
FIG. 8 is a block diagram of an example of a motherboard with no daughterboard that can be used in a data processing system that can be associated with a bed.

FIG. 8 is a block diagram of an example of a motherboard 800 with no daughterboard that can be used in a data processing system that can be associated with a bed system, including those described above with respect to FIGS. 1-3. In this example, the motherboard 800 can perform most, all, or more of the features described with reference to the motherboard 402 in FIG. 6 and the daughterboard 404 in FIG. 7.

Figure 9:
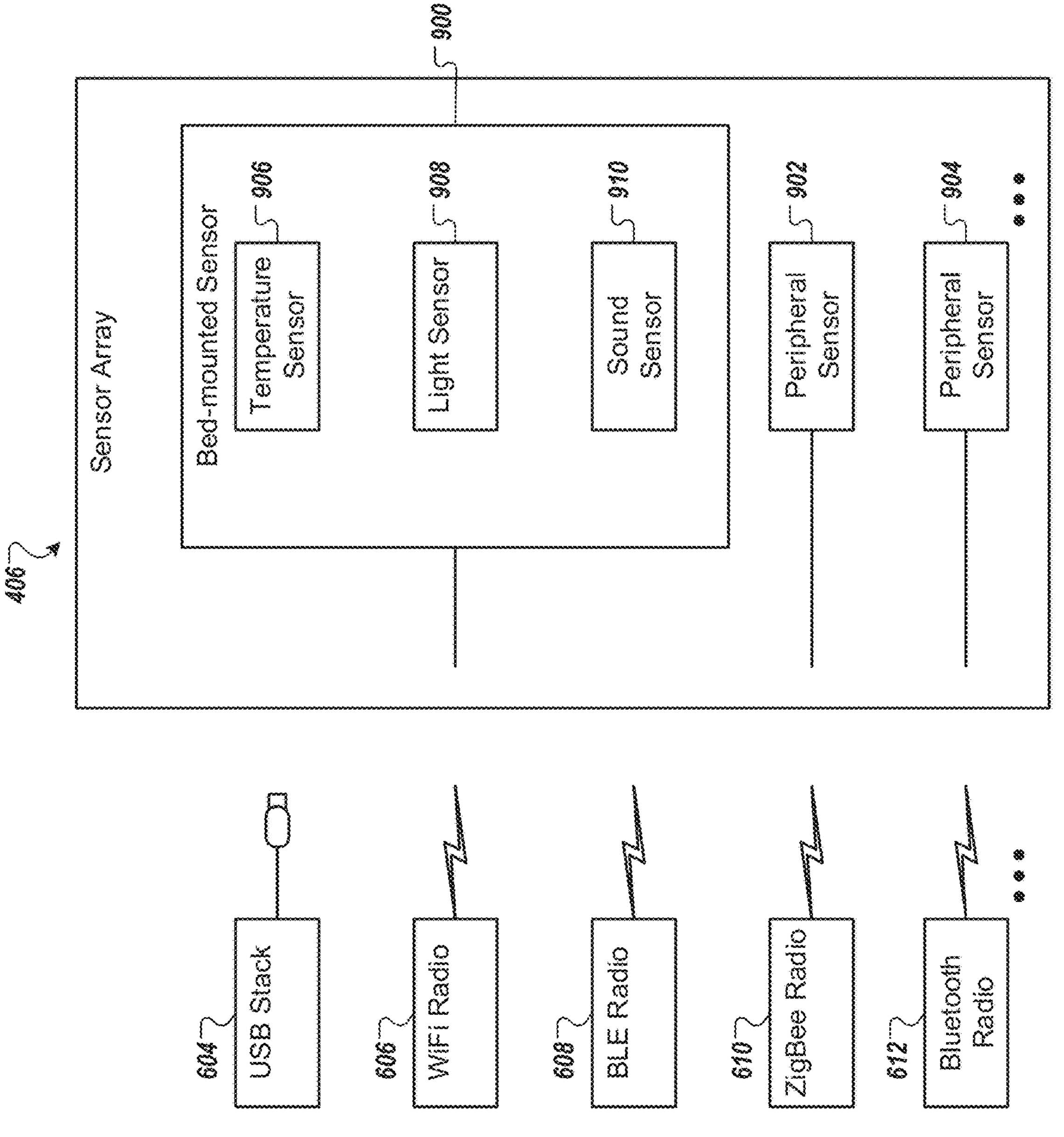
FIG. 9 is a block diagram of an example of a sensory array that can be used in a data processing system that can be associated with a bed.

FIG. 9 is a block diagram of an example of a sensory array 406 that can be used in a data processing system that can be associated with a bed system, including those described above with respect to FIGS. 1-3. In general, the sensor array 406 is a conceptual grouping of some or all the peripheral sensors that communicate with the motherboard 402 but are not native to the motherboard 402.

The peripheral sensors of the sensor array 406 can communicate with the motherboard 402 through one or more of the network interfaces of the motherboard, including but not limited to the USB stack 1112, a WiFi radio 606, a Bluetooth Low Energy (BLE) radio 608, a ZigBee radio 610, and a Bluetooth radio 612, as is appropriate for the configuration of the particular sensor. For example, a sensor that outputs a reading over a USB cable can communicate through the USB stack 1112.

Some of the peripheral sensors 900 of the sensor array 406 can be bed mounted 900. These sensors can be, for example, embedded into the structure of a bed and sold with the bed, or later affixed to the structure of the bed. Other peripheral sensors 902 and 904 can be in communication with the motherboard 402, but optionally not mounted to the bed. In some cases, some or all of the bed mounted sensors 900 and/or peripheral sensors 902 and 904 can share networking hardware, including a conduit that contains wires from each sensor, a multi-wire cable or plug that, when affixed to the motherboard 402, connect all of the associated sensors with the motherboard 402. In some embodiments, one, some, or all of sensors 902, 904, 906, 908, and 910 can sense one or more features of a mattress, such as pressure, temperature, light, sound, and/or one or more other features of the mattress. In some embodiments, one, some, or all of sensors 902, 904, 906, 908, and 910 can sense one or more features external to the mattress. In some embodiments, pressure sensor 902 can sense pressure of the mattress while some or all of sensors 902, 904, 906, 908, and 910 can sense one or more features of the mattress and/or external to the mattress.

Figure 10:
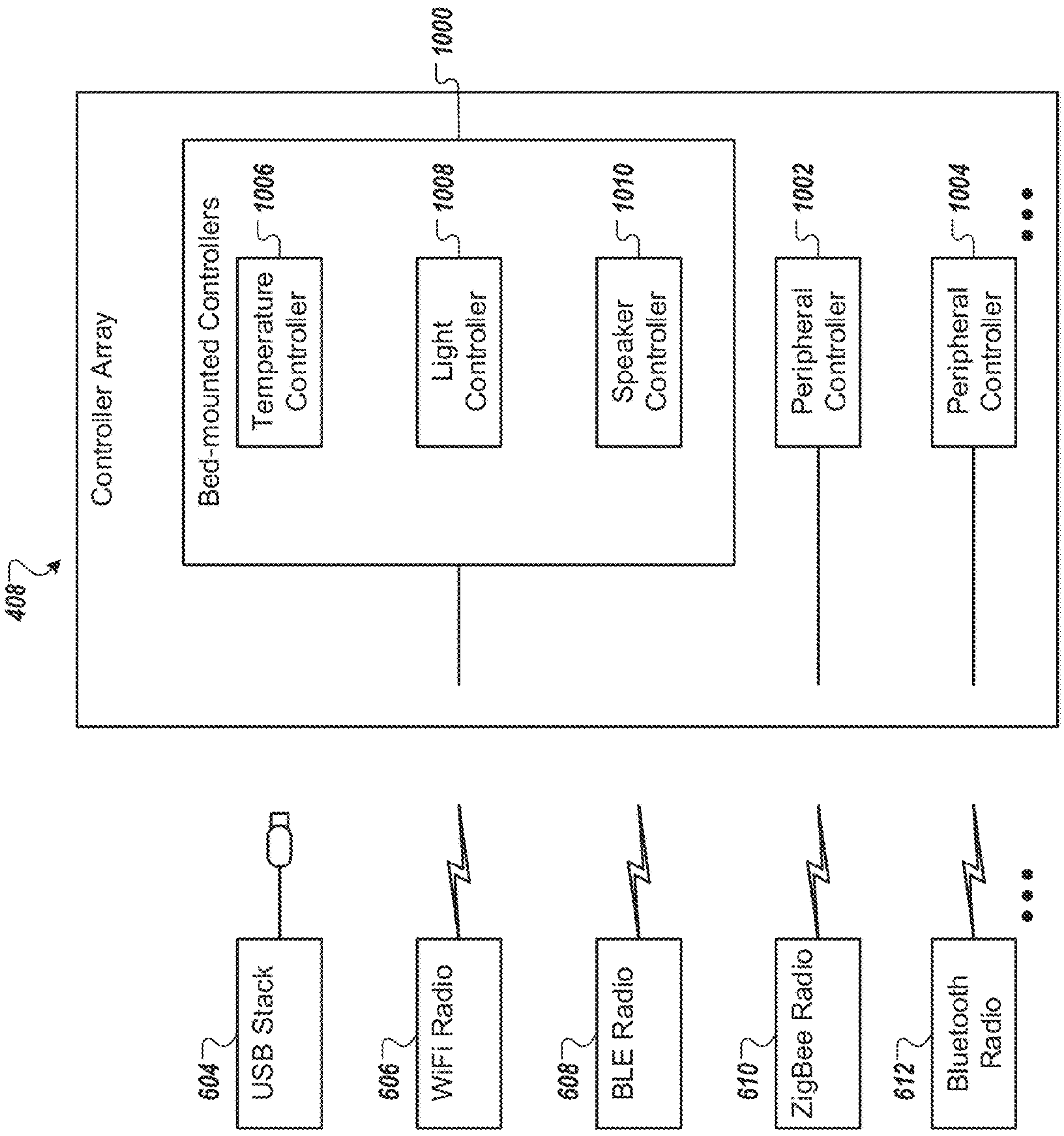
FIG. 10 is a block diagram of an example of a control array that can be used in a data processing system that can be associated with a bed

FIG. 10 is a block diagram of an example of a controller array 408 that can be used in a data processing system that can be associated with a bed system, including those described above with respect to FIGS. 1-3. In general, the controller array 408 is a conceptual grouping of some or all peripheral controllers that communicate with the motherboard 402 but are not native to the motherboard 402.

The peripheral controllers of the controller array 408 can communicate with the motherboard 402 through one or more of the network interfaces of the motherboard, including but not limited to the USB stack 1112, a WiFi radio 1114, a Bluetooth Low Energy (BLE) radio 1116, a ZigBee radio 610, and a Bluetooth radio 612, as is appropriate for the configuration of the particular sensor. For example, a controller that receives a command over a USB cable can communicate through the USB stack 1112.

Some of the controllers of the controller array 408 can be bed mounted 1000, including but not limited to a temperature controller 1006, a light controller 1008, and/or a speaker controller 1010. These controllers can be, for example, embedded into the structure of a bed and sold with the bed, or later affixed to the structure of the bed. Other peripheral controllers 1002 and 1004 can be in communication with the motherboard 402, but optionally not mounted to the bed. In some cases, some or all of the bed mounted controllers 1000 and/or peripheral controllers 1002 and 1004 can share networking hardware, including a conduit that contains wires for each controller, a multi-wire cable or plug that, when affixed to the motherboard 402, connects all of the associated controllers with the motherboard 402.

Figure 11:
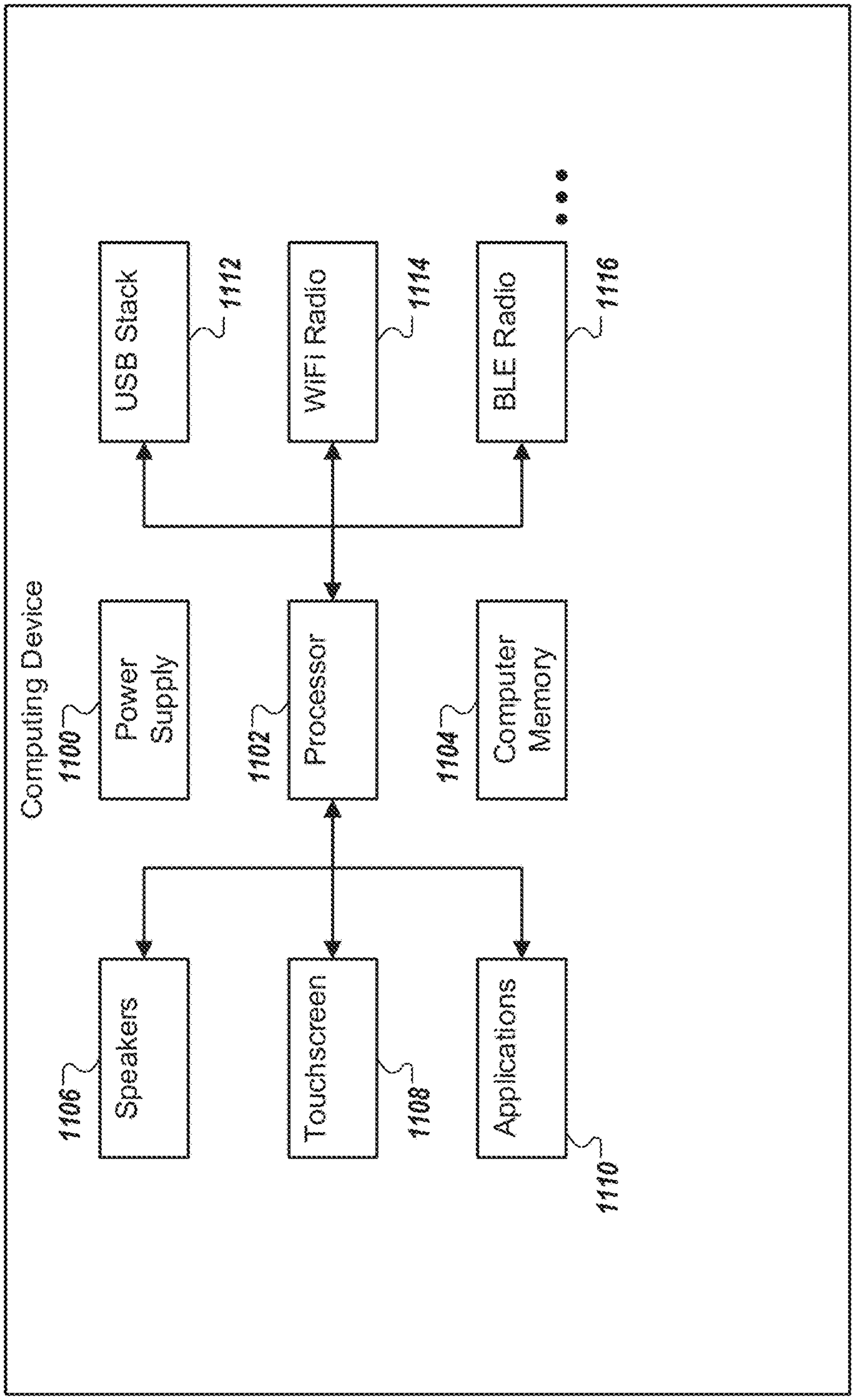
FIG. 11 is a block diagram of an example of a computing device that can be used in a data processing system that can be associated with a bed.

FIG. 11 is a block diagram of an example of a computing device 414 that can be used in a data processing system that can be associated with a bed system, including those described above with respect to FIGS. 1-3. The computing device 414 can include, for example, computing devices used by a user of a bed. Example computing devices 414 include, but are not limited to, mobile computing devices (e.g., mobile phones, tablet computers, laptops) and desktop computers.

The computing device 414 includes a power supply 1100, a processor 1102, and computer readable memory 1104. User input and output can be transmitted by, for example, speakers 1106, a touchscreen 1108, or other not shown components such as a pointing device or keyboard. The computing device 414 can run one or more applications 1110. These applications can include, for example, application to allow the user to interact with the system 400. These applications can allow a user to view information about the bed (e.g., sensor readings, sleep metrics), or configure the behavior of the system 400 (e.g., set a desired firmness to the bed, set desired behavior for peripheral devices). In some cases, the computing device 414 can be used in addition to, or to replace, the remote control 122 described previously.

Figure 12:
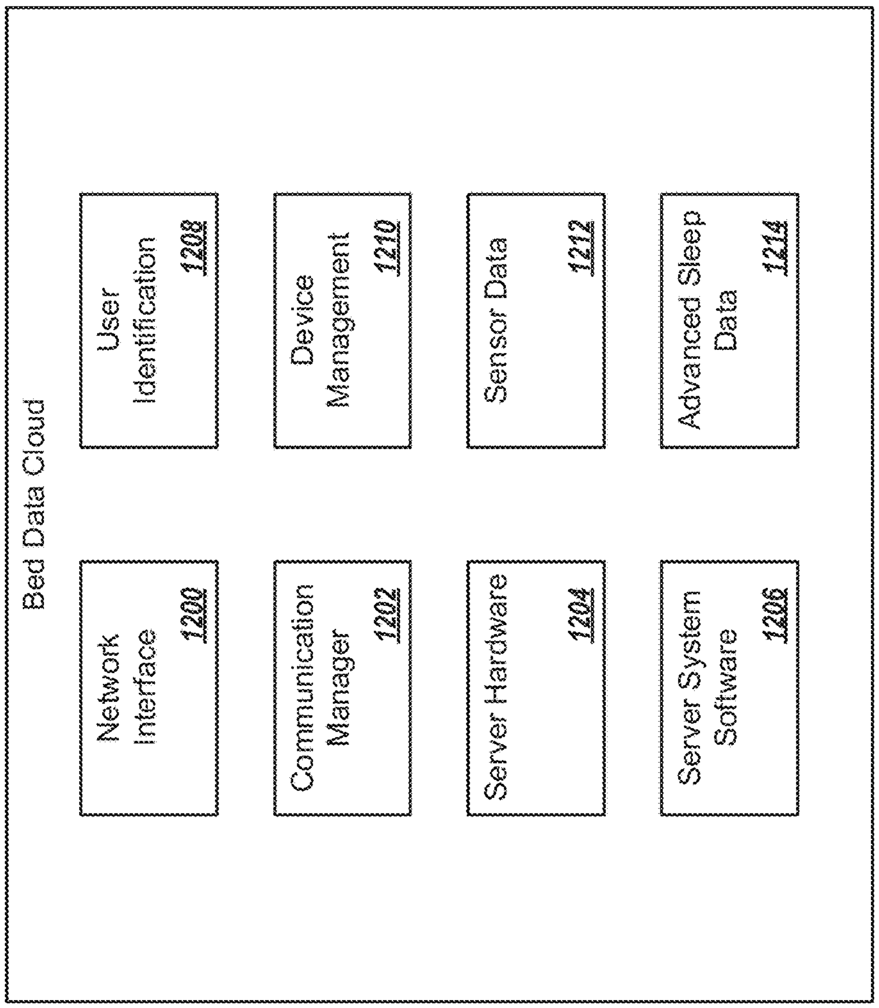
FIGS. 12-16 are block diagrams of example cloud services that can be used in a data processing system that can be associated with a bed.

FIG. 12 is a block diagram of an example bed data cloud service 410*a* that can be used in a data processing system that can be associated with a bed system, including those described above with respect to FIGS. 1-3. In this example, the bed data cloud service 410*a* is configured to collect sensor data and sleep data from a particular bed, and to match the sensor and sleep data with one or more users that use the bed when the sensor and sleep data was generated.

The bed data cloud service 410*a* is shown with a network interface 1200, a communication manager 1202, server hardware 1204, and server system software 1206. In addition, the bed data cloud service 410*a* is shown with a user identification module 1208, a device management 1210 module, a sensor data module 1212, and an advanced sleep data module 1214.

The network interface 1200 generally includes hardware and low level software used to allow one or more hardware devices to communicate over networks. For example the network interface 1200 can include network cards, routers, modems, and other hardware needed to allow the components of the bed data cloud service 410*a* to communicate with each other and other destinations over, for example, the Internet 412. The communication manger 1202 generally comprises hardware and software that operate above the network interface 1200. This includes software to initiate, maintain, and tear down network communications used by the bed data cloud service 410*a*. This includes, for example, TCP/IP, SSL or TLS, Torrent, and other communication sessions over local or wide area networks. The communication manger 1202 can also provide load balancing and other services to other elements of the bed data cloud service 410*a*.

The server hardware 1204 generally includes the physical processing devices used to instantiate and maintain bed data cloud service 410*a*. This hardware includes, but is not limited to processors (e.g., central processing units, ASICs, graphical processers), and computer readable memory (e.g., random access memory, stable hard disks, tape backup). One or more servers can be configured into clusters, multi-computer, or datacenters that can be geographically separate or connected.

The server system software 1206 generally includes software that runs on the server hardware 1204 to provide operating environments to applications and services. The server system software 1206 can include operating systems running on real servers, virtual machines instantiated on real servers to create many virtual servers, server level operations such as data migration, redundancy, and backup.

The user identification 1208 can include, or reference, data related to users of beds with associated data processing systems. For example, the users can include customers, owners, or other users registered with the bed data cloud service 410*a* or another service. Each user can have, for example, a unique identifier, user credentials, contact information, billing information, demographic information, or any other technologically appropriate information.

The device manager 1210 can include, or reference, data related to beds or other products associated with data processing systems. For example, the beds can include products sold or registered with a system associated with the bed data cloud service 410*a*. Each bed can have, for example, a unique identifier, model and/or serial number, sales information, geographic information, delivery information, a listing of associated sensors and control peripherals, etc. Additionally, an index or indexes stored by the bed data cloud service 410*a* can identify users that are associated with beds. For example, this index can record sales of a bed to a user, users that sleep in a bed, etc.

The sensor data 1212 can record raw or condensed sensor data recorded by beds with associated data processing systems. For example, a bed's data processing system can have a temperature sensor, pressure sensor, and light sensor. Readings from these sensors, either in raw form or in a format generated from the raw data (e.g. sleep metrics) of the sensors, can be communicated by the bed's data processing system to the bed data cloud service 410*a* for storage in the sensor data 1212. Additionally, an index or indexes stored by the bed data cloud service 410*a* can identify users and/or beds that are associated with the sensor data 1212.

The bed data cloud service 410*a* can use any of its available data to generate advanced sleep data 1214. In general, the advanced sleep data 1214 includes sleep metrics and other data generated from sensor readings. Some of these calculations can be performed in the bed data cloud service 410*a* instead of locally on the bed's data processing system, for example, because the calculations are computationally complex or require a large amount of memory space or processor power that is not available on the bed's data processing system. This can help allow a bed system to operate with a relatively simple controller and still be part of a system that performs relatively complex tasks and computations.

Figure 13:
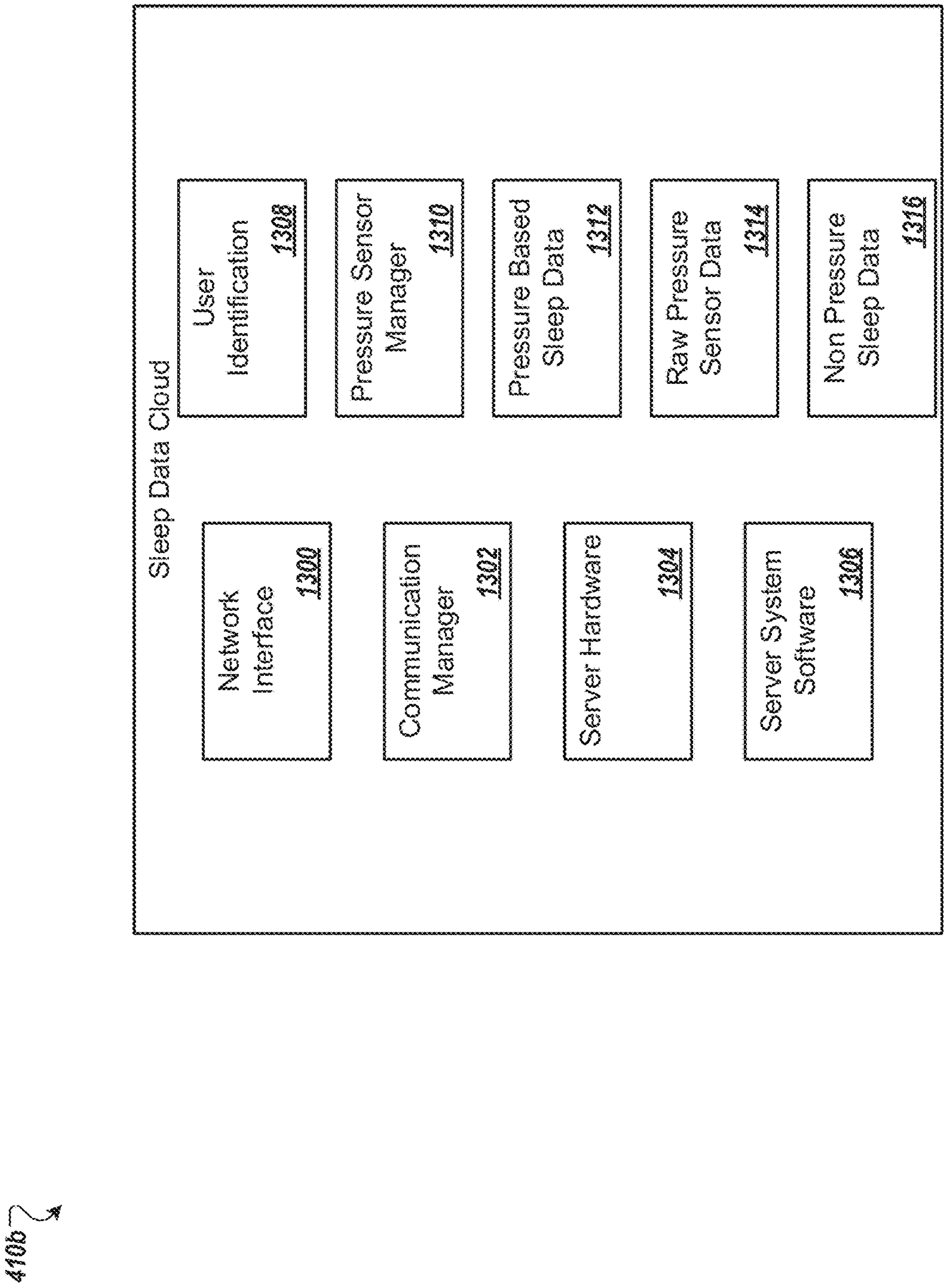

FIG. 13 is a block diagram of an example sleep data cloud service 410*b* that can be used in a data processing system that can be associated with a bed system, including those described above with respect to FIGS. 1-3. In this example, the sleep data cloud service 410*b* is configured to record data related to users' sleep experience.

The sleep data cloud service 410*b* is shown with a network interface 1300, a communication manager 1302, server hardware 1304, and server system software 1306. In addition, the sleep data cloud service 410*b* is shown with a user identification module 1308, a pressure sensor manager 1310, a pressure based sleep data module 1312, a raw pressure sensor data module 1314, and a non-pressure sleep data module 1316.

The pressure sensor manager 1310 can include, or reference, data related to the configuration and operation of pressure sensors in beds. For example, this data can include an identifier of the types of sensors in a particular bed, their settings and calibration data, etc.

The pressure based sleep data 1312 can use raw pressure sensor data 1314 to calculate sleep metrics specifically tied to pressure sensor data. For example, user presence, movements, weight change, heart rate, and breathing rate can all be determined from raw pressure sensor data 1314. Additionally, an index or indexes stored by the sleep data cloud service 410*b* can identify users that are associated with pressure sensors, raw pressure sensor data, and/or pressure based sleep data.

The non-pressure sleep data 1316 can use other sources of data to calculate sleep metrics. For example, user entered preferences, light sensor readings, and sound sensor readings can all be used to track sleep data. Additionally, an index or indexes stored by the sleep data cloud service 410*b* can identify users that are associated with other sensors and/or non-pressure sleep data 1316.

Figure 14:
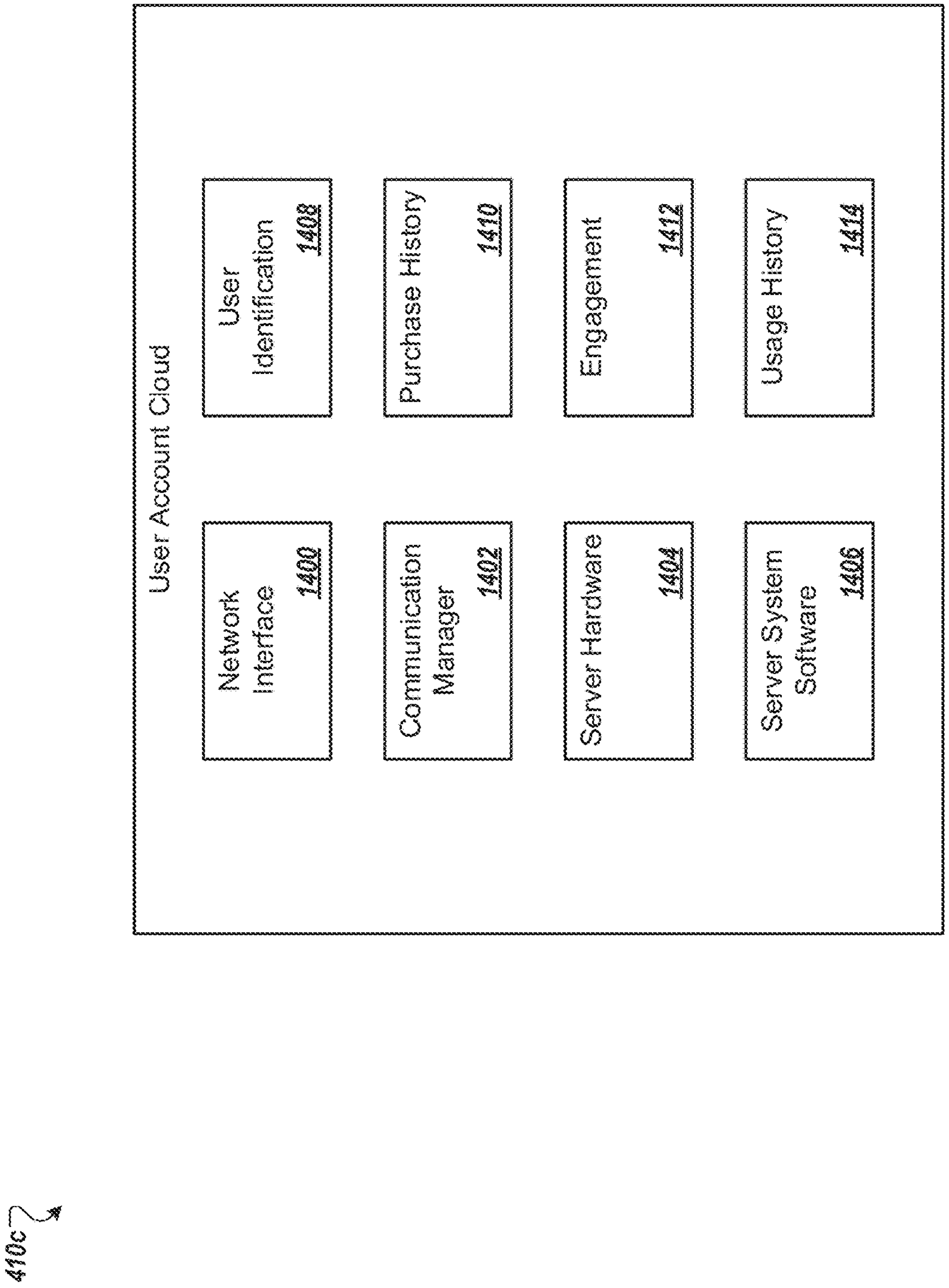

FIG. 14 is a block diagram of an example user account cloud service 410*c* that can be used in a data processing system that can be associated with a bed system, including those described above with respect to FIGS. 1-3. In this example, the user account cloud service 410*c* is configured to record a list of users and to identify other data related to those users.

The user account cloud service 410*c* is shown with a network interface 1400, a communication manager 1402, server hardware 1404, and server system software 1406. In addition, the user account cloud service 410*c* is shown with a user identification module 1408, a purchase history module 1410, an engagement module 1412, and an application usage history module 1414.

The user identification module 1408 can include, or reference, data related to users of beds with associated data processing systems. For example, the users can include customers, owners, or other users registered with the user account cloud service 410*a* or another service. Each user can have, for example, a unique identifier, and user credentials, demographic information, or any other technologically appropriate information.

The purchase history module 1410 can include, or reference, data related to purchases by users. For example, the purchase data can include a sale's contact information, billing information, and salesperson information. Additionally, an index or indexes stored by the user account cloud service 410*c* can identify users that are associated with a purchase.

The engagement 1412 can track user interactions with the manufacturer, vendor, and/or manager of the bed and or cloud services. This engagement data can include communications (e.g., emails, service calls), data from sales (e.g., sales receipts, configuration logs), and social network interactions.

The usage history module 1414 can contain data about user interactions with one or more applications and/or remote controls of a bed. For example, a monitoring and configuration application can be distributed to run on, for example, computing devices 412. This application can log and report user interactions for storage in the application usage history module 1414. Additionally, an index or indexes stored by the user account cloud service 410*c* can identify users that are associated with each log entry.

Figure 15:
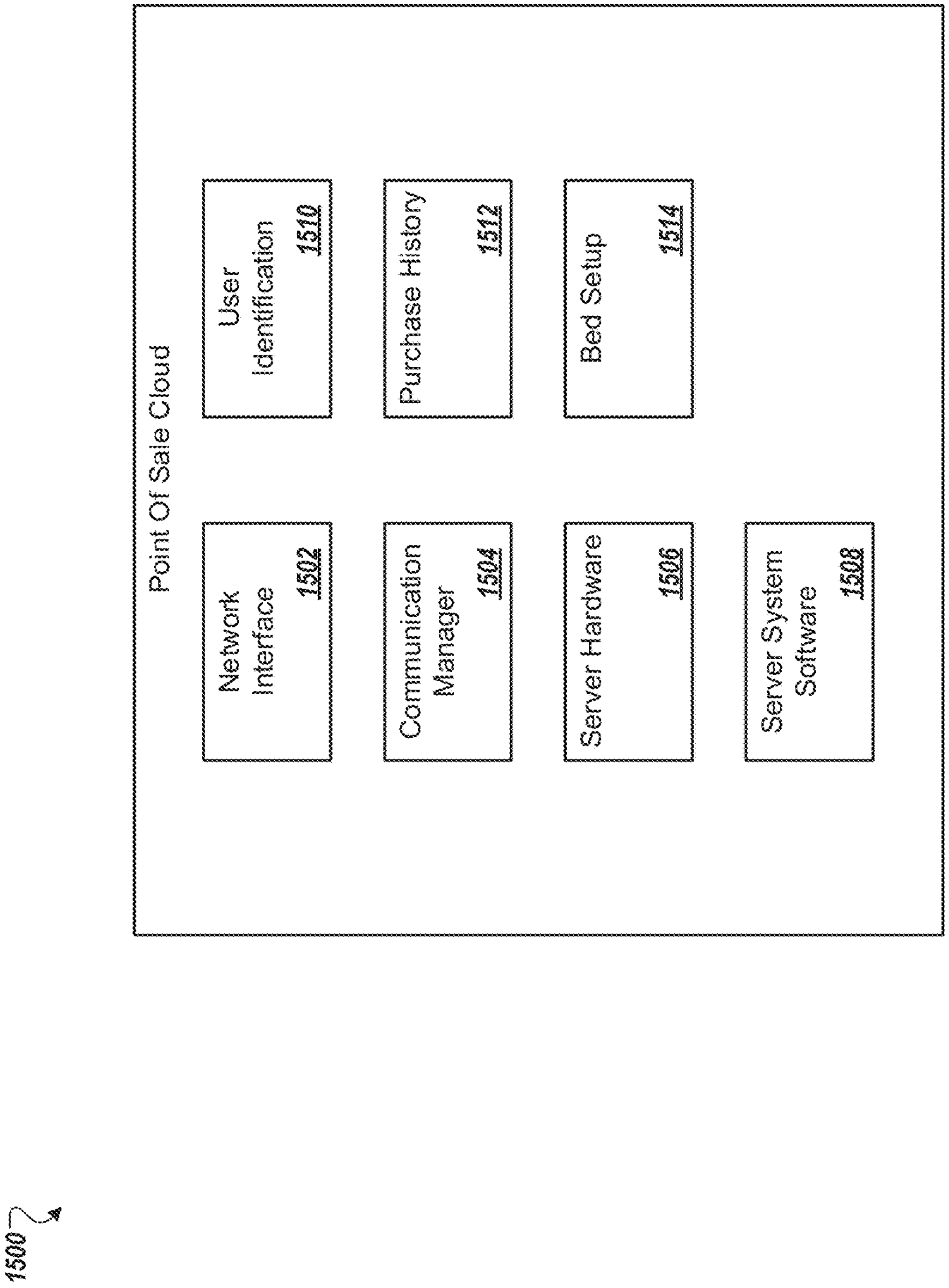

FIG. 15 is a block diagram of an example point of sale cloud service 1500 that can be used in a data processing system that can be associated with a bed system, including those described above with respect to FIGS. 1-3. In this example, the point of sale cloud service 1500 is configured to record data related to users' purchases.

The point of sale cloud service 1500 is shown with a network interface 1502, a communication manager 1504, server hardware 1506, and server system software 1508. In addition, the point of sale cloud service 1500 is shown with a user identification module 1510, a purchase history module 1512, and a setup module 1514.

The purchase history module 1512 can include, or reference, data related to purchases made by users identified in the user identification module 1510. The purchase information can include, for example, data of a sale, price, and location of sale, delivery address, and configuration options selected by the users at the time of sale. These configuration options can include selections made by the user about how they wish their newly purchased beds to be setup and can include, for example, expected sleep schedule, a listing of peripheral sensors and controllers that they have or will install, etc.

The bed setup module 1514 can include, or reference, data related to installations of beds that users' purchase. The bed setup data can include, for example, the date and address to which a bed is delivered, the person that accepts delivery, the configuration that is applied to the bed upon delivery, the name or names of the person or people who will sleep on the bed, which side of the bed each person will use, etc.

Data recorded in the point of sale cloud service 1500 can be referenced by a user's bed system at later dates to control functionality of the bed system and/or to send control signals to peripheral components according to data recorded in the point of sale cloud service 1500. This can allow a salesperson to collect information from the user at the point of sale that later facilitates automation of the bed system. In some examples, some or all aspects of the bed system can be automated with little or no user-entered data required after the point of sale. In other examples, data recorded in the point of sale cloud service 1500 can be used in connection with a variety of additional data gathered from user-entered data.

Figure 16:
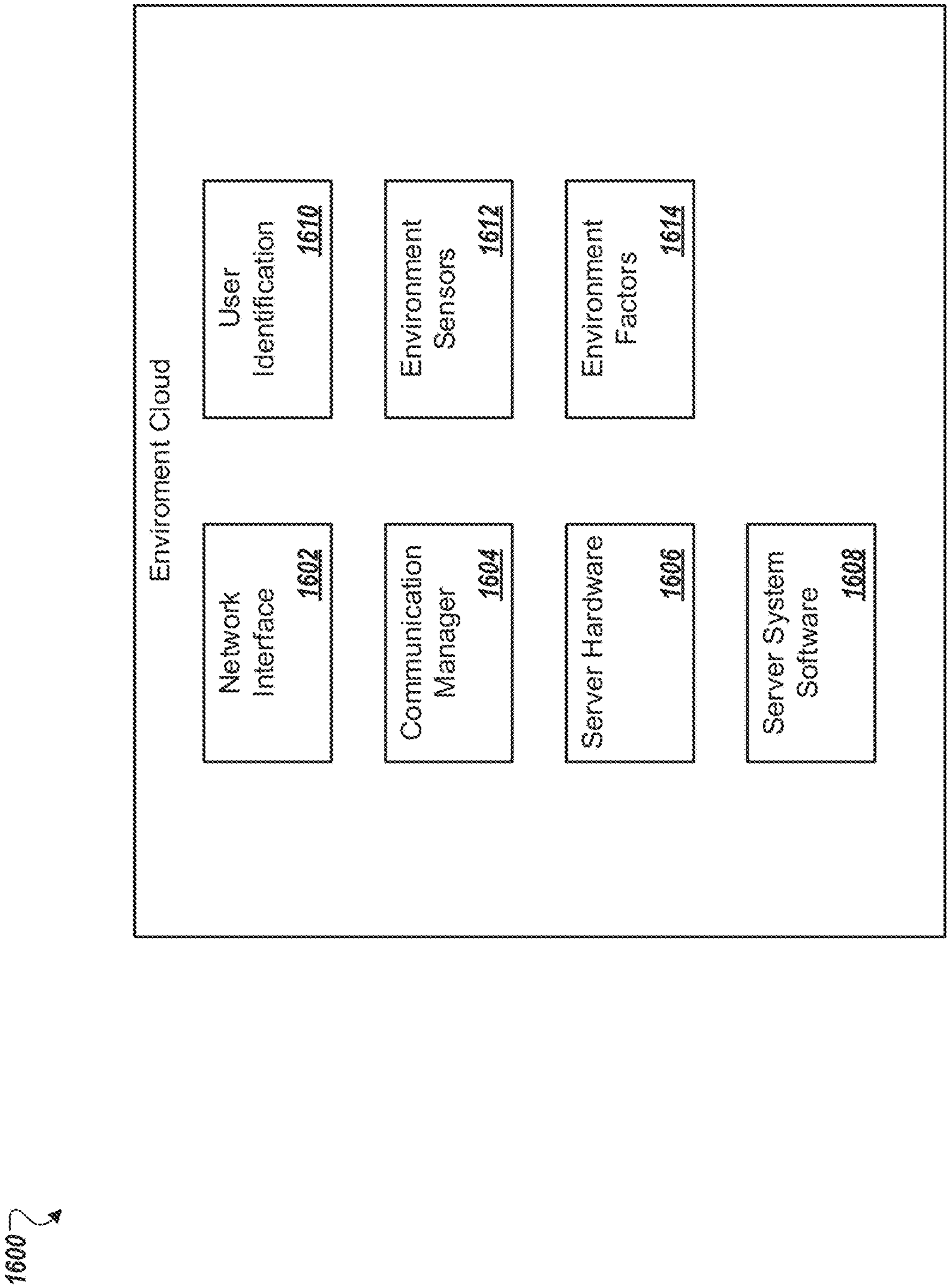

FIG. 16 is a block diagram of an example environment cloud service 1600 that can be used in a data processing system that can be associated with a bed system, including those described above with respect to FIGS. 1-3. In this example, the environment cloud service 1600 is configured to record data related to users' home environment.

The environment cloud service 1600 is shown with a network interface 1602, a communication manager 1604, server hardware 1606, and server system software 1608. In addition, the environment cloud service 1600 is shown with a user identification module 1610, an environmental sensor module 1612, and an environmental factors module 1614.

The environmental sensors module 1612 can include a listing of sensors that users' in the user identification module 1610 have installed in their bed. These sensors include any sensors that can detect environmental variables—light sensors, noise sensors, vibration sensors, thermostats, etc. Additionally, the environmental sensors module 1612 can store historical readings or reports from those sensors.

The environmental factors module 1614 can include reports generated based on data in the environmental sensors module 1612. For example, for a user with a light sensor with data in the environment sensors module 1612, the environmental factors module 1614 can hold a report indicating the frequency and duration of instances of increased lighting when the user is asleep.

In the examples discussed here, each cloud service 410 is shown with some of the same components. In various configurations, these same components can be partially or wholly shared between services, or they can be separate. In some configurations, each service can have separate copies of some or all of the components that are the same or different in some ways. Additionally, these components are only supplied as illustrative examples. In other examples each cloud service can have different number, types, and styles of components that are technically possible.

Figure 17:
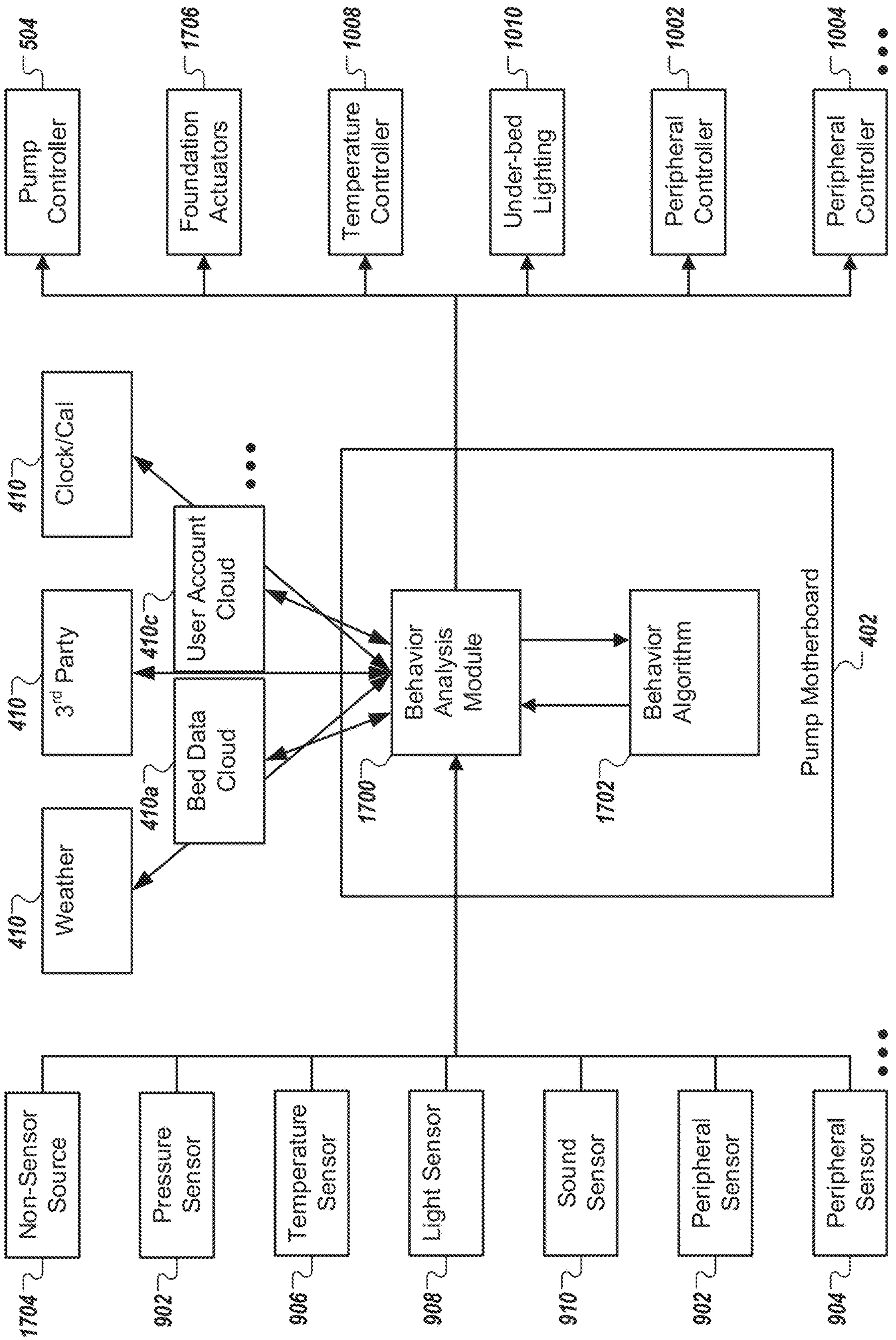
FIG. 17 is a block diagram of an example of using a data processing system that can be associated with a bed to automate peripherals around the bed.

FIG. 17 is a block diagram of an example of using a data processing system that can be associated with a bed (such as a bed of the bed systems described herein) to automate peripherals around the bed. Shown here is a behavior analysis module 1700 that runs on the pump motherboard 402. For example, the behavior analysis module 1700 can be one or more software components stored on the computer memory 512 and executed by the processor 502. In general, the behavior analysis module 1700 can collect data from a wide variety of sources (e.g., sensors, non-sensor local sources, cloud data services) and use a behavioral algorithm 1702 to generate one or more actions to be taken (e.g., commands to send to peripheral controllers, data to send to cloud services). This can be useful, for example, in tracking user behavior and automating devices in communication with the user's bed.

The behavior analysis module 1700 can collect data from any technologically appropriate source, for example, to gather data about features of a bed, the bed's environment, and/or the bed's users. Some such sources include any of the sensors of the sensor array 406. For example, this data can provide the behavior analysis module 1700 with information about the current state of the environment around the bed. For example, the behavior analysis module 1700 can access readings from the pressure sensor 902 to determine the pressure of an air chamber in the bed. From this reading, and potentially other data, user presence in the bed can be determined. In another example, the behavior analysis module can access a light sensor 908 to detect the amount of light in the bed's environment.

Similarly, the behavior analysis module 1700 can access data from cloud services. For example, the behavior analysis module 1700 can access the bed cloud service 410*a* to access historical sensor data 1212 and/or advanced sleep data 1214. Other cloud services 410, including those not previously described can be accessed by the behavior analysis module 1700. For example, the behavior analysis module 1700 can access a weather reporting service, a $3^{rd}$ party data provider (e.g., traffic and news data, emergency broadcast data, user travel data), and/or a clock and calendar service.

Similarly, the behavior analysis module 1700 can access data from non-sensor sources 1704. For example, the behavior analysis module 1700 can access a local clock and calendar service (e.g., a component of the motherboard 402 or of the processor 502).

The behavior analysis module 1700 can aggregate and prepare this data for use by one or more behavioral algorithms 1702. The behavioral algorithms 1702 can be used to learn a user's behavior and/or to perform some action based on the state of the accessed data and/or the predicted user behavior. For example, the behavior algorithm 1702 can use available data (e.g., pressure sensor, non-sensor data, clock and calendar data) to create a model of when a user goes to bed every night. Later, the same or a different behavioral algorithm 1702 can be used to determine if an increase in air chamber pressure is likely to indicate a user going to bed and, if so, send some data to a third-party cloud service 410 and/or engage a device such as a pump controller 504, foundation actuators 1706, temperature controller 1008, under-bed lighting 1010, a peripheral controller 1002, or a peripheral controller 1004, to name a few.

In the example shown, the behavioral analysis module 1700 and the behavioral algorithm 1702 are shown as components of the motherboard 402. However, other configurations are possible. For example, the same or a similar behavioral analysis module and/or behavior algorithm can be run in one or more cloud services, and the resulting output can be sent to the motherboard 402, a controller in the controller array 408, or to any other technologically appropriate recipient.

Figure 18:
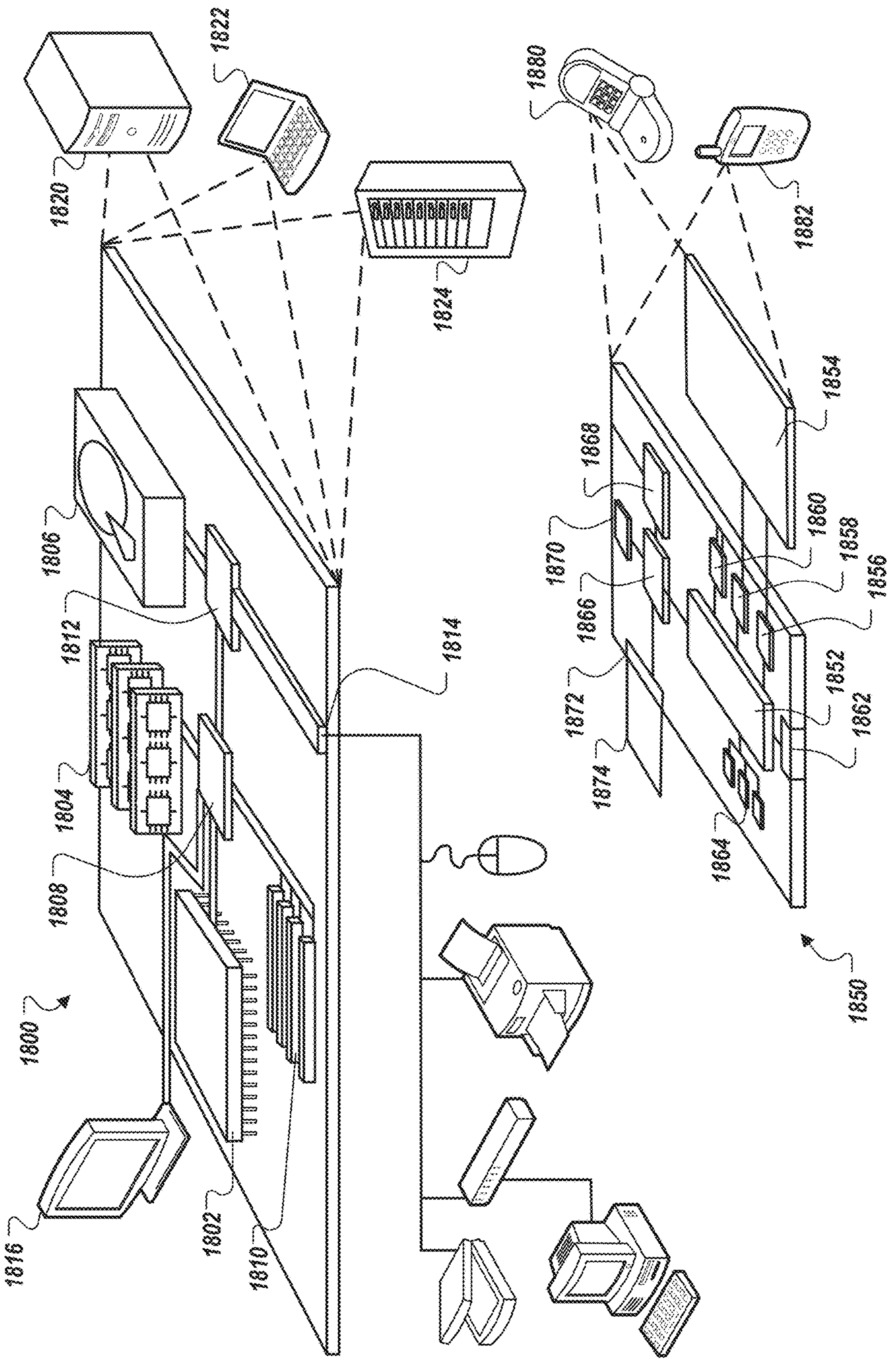
FIG. 18 is a schematic diagram that shows an example of a computing device and a mobile computing device.

FIG. 18 shows an example of a computing device 1800 and an example of a mobile computing device that can be used to implement the techniques described here. The computing device 1800 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1800 includes a processor 1802, a memory 1804, a storage device 1806, a high-speed interface 1808 connecting to the memory 1804 and multiple high-speed expansion ports 1810, and a low-speed interface 1812 connecting to a low-speed expansion port 1814 and the storage device 1806. Each of the processor 1802, the memory 1804, the storage device 1806, the high-speed interface 1808, the high-speed expansion ports 1810, and the low-speed interface 1812, are interconnected using various busses, and can be mounted on a common motherboard or in other manners as appropriate. The processor 1802 can process instructions for execution within the computing device 1800, including instructions stored in the memory 1804 or on the storage device 1806 to display graphical information for a GUI on an external input/output device, such as a display 1816 coupled to the high-speed interface 1808. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1804 stores information within the computing device 1800. In some implementations, the memory 1804 is a volatile memory unit or units. In some implementations, the memory 1804 is a non-volatile memory unit or units. The memory 1804 can also be another form of computer-readable medium, such as a magnetic or optical disk.

The storage device 1806 is capable of providing mass storage for the computing device 1800. In some implementations, the storage device 1806 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1804, the storage device 1806, or memory on the processor 1802.

The high-speed interface 1808 manages bandwidth-intensive operations for the computing device 1800, while the low-speed interface 1812 manages lower bandwidth-intensive operations. Such allocation of functions is exemplary only. In some implementations, the high-speed interface 1808 is coupled to the memory 1804, the display 1816 (e.g., through a graphics processor or accelerator), and to the high-speed expansion ports 1810, which can accept various expansion cards (not shown). In the implementation, the low-speed interface 1812 is coupled to the storage device 1806 and the low-speed expansion port 1814. The low-speed expansion port 1814, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1800 can be implemented in a number of different forms, as shown in the figure. For example, it can be implemented as a standard server 1820, or multiple times in a group of such servers. In addition, it can be implemented in a personal computer such as a laptop computer 1822. It can also be implemented as part of a rack server system 1824. Alternatively, components from the computing device 1800 can be combined with other components in a mobile device (not shown), such as a mobile computing device 1850. Each of such devices can contain one or more of the computing device 1800 and the mobile computing device 1850, and an entire system can be made up of multiple computing devices communicating with each other.

The mobile computing device 1850 includes a processor 1852, a memory 1864, an input/output device such as a display 1854, a communication interface 1866, and a transceiver 1868, among other components. The mobile computing device 1850 can also be provided with a storage device, such as a micro-drive or other device, to provide additional storage. Each of the processor 1852, the memory 1864, the display 1854, the communication interface 1866, and the transceiver 1868, are interconnected using various buses, and several of the components can be mounted on a common motherboard or in other manners as appropriate.

The processor 1852 can execute instructions within the mobile computing device 1850, including instructions stored in the memory 1864. The processor 1852 can be implemented as a chipset of chips that include separate and multiple analog and digital processors. The processor 1852 can provide, for example, for coordination of the other components of the mobile computing device 1850, such as control of user interfaces, applications run by the mobile computing device 1850, and wireless communication by the mobile computing device 1850.

The processor 1852 can communicate with a user through a control interface 1858 and a display interface 1856 coupled to the display 1854. The display 1854 can be, for example, a TFT (Thin-Film-Transistor Liquid Crystal Display) display or an OLED (Organic Light Emitting Diode) display, or other appropriate display technology. The display interface 1856 can comprise appropriate circuitry for driving the display 1854 to present graphical and other information to a user. The control interface 1858 can receive commands from a user and convert them for submission to the processor 1852. In addition, an external interface 1862 can provide communication with the processor 1852, so as to enable near area communication of the mobile computing device 1850 with other devices. The external interface 1862 can provide, for example, for wired communication in some implementations, or for wireless communication in other implementations, and multiple interfaces can also be used.

The memory 1864 stores information within the mobile computing device 1850. The memory 1864 can be implemented as one or more of a computer-readable medium or media, a volatile memory unit or units, or a non-volatile memory unit or units. An expansion memory 1874 can also be provided and connected to the mobile computing device 1850 through an expansion interface 1872, which can include, for example, a SIMM (Single In Line Memory Module) card interface. The expansion memory 1874 can provide extra storage space for the mobile computing device 1850, or can also store applications or other information for the mobile computing device 1850. Specifically, the expansion memory 1874 can include instructions to carry out or supplement the processes described above, and can include secure information also. Thus, for example, the expansion memory 1874 can be provide as a security module for the mobile computing device 1850, and can be programmed with instructions that permit secure use of the mobile computing device 1850. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1864, the expansion memory 1874, or memory on the processor 1852. In some implementations, the computer program product can be received in a propagated signal, for example, over the transceiver 1868 or the external interface 1862.

The mobile computing device 1850 can communicate wirelessly through the communication interface 1866, which can include digital signal processing circuitry where necessary. The communication interface 1866 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1868 using a radio-frequency. In addition, short-range communication can occur, such as using a Bluetooth, WiFi, or other such transceiver (not shown). In addition, a GPS (Global Positioning System) receiver module 1870 can provide additional navigation- and location-related wireless data to the mobile computing device 1850, which can be used as appropriate by applications running on the mobile computing device 1850.

The mobile computing device 1850 can also communicate audibly using an audio codec 1860, which can receive spoken information from a user and convert it to usable digital information. The audio codec 1860 can likewise generate audible sound for a user, such as through a speaker, e.g., in a handset of the mobile computing device 1850. Such sound can include sound from voice telephone calls, can include recorded sound (e.g., voice messages, music files, etc.) and can also include sound generated by applications operating on the mobile computing device 1850.

The mobile computing device 1850 can be implemented in a number of different forms, as shown in the figure. For example, it can be implemented as a cellular telephone 1880. It can also be implemented as part of a smart-phone 1882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a graphical user interface or a Web browser through which a user can interact with an implementation of the systems and techniques described here), or any combination of such backend, middleware, or frontend components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Figure 19A:
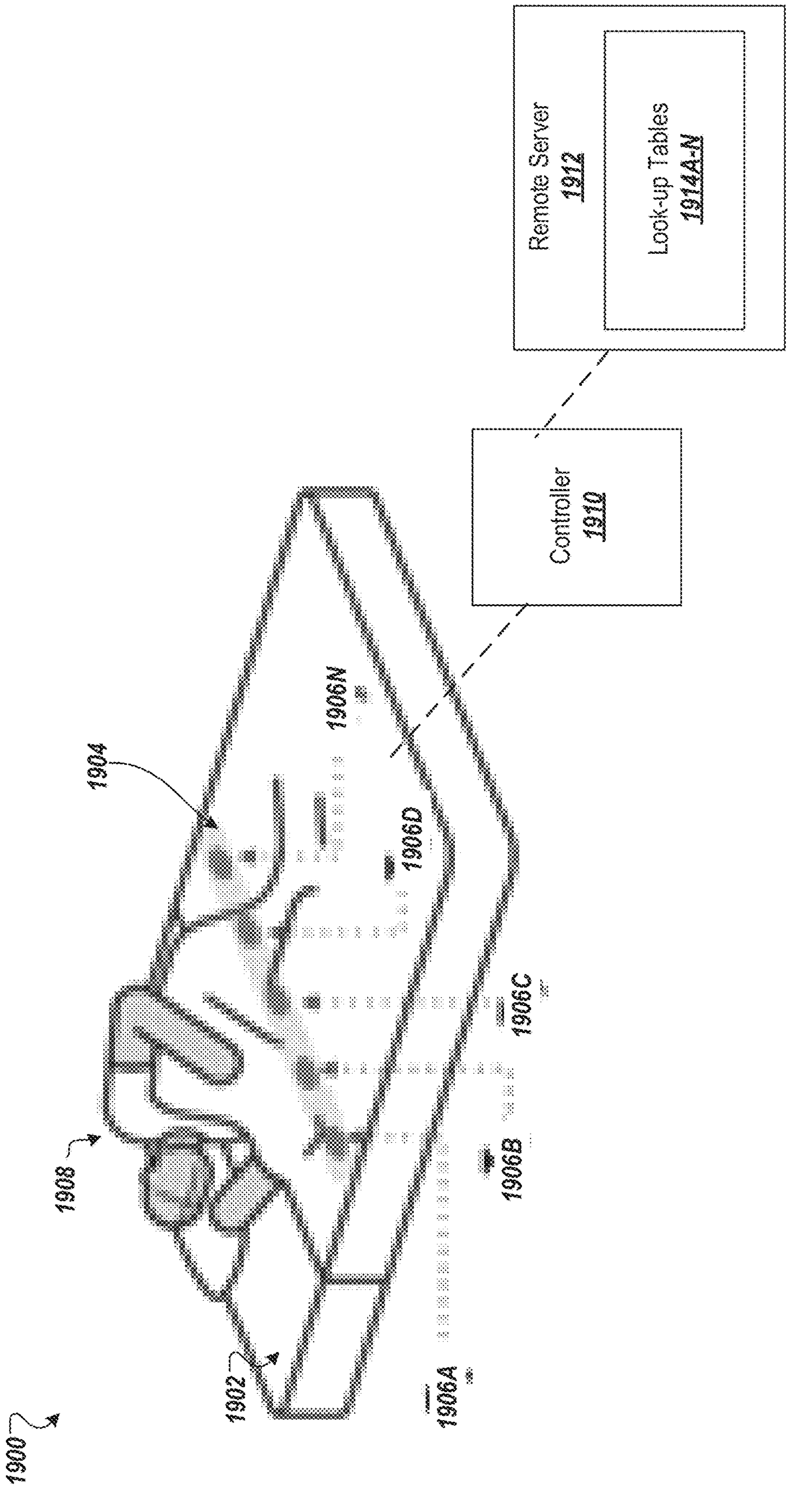
FIG. 19A is an example bed system with a sensor array.

FIG. 19A is an example bed system 1900 with a sensor array 1904. The sensor array 1904 can be integrated into the bed system 1900. The sensor array 1904 can be used by a controller 1910 when adjusting one or more thermal microclimates of the bed system 1900 to maximize sleep quality of an occupant 1908.

In some implementations, the sensor array 1904 can be attached to a bed by affixing it to a mattress surface 1902. As depicted in FIG. 19A, the sensor array 1904 can be positioned around a midpoint or center of the bed system 1900. The sensor array 1904 can be a linear array. The linear array 1904 can have a linear axis. Moreover, the bed system 1900 can have a sleeper section (e.g., the mattress surface 1902) adapted to support a sleeper (e.g., occupant 1908). The sleeper section can have a major axis through a center of a longest dimension of the sleeper section. The linear array 1904 can be situated so that the linear axis of the linear array 1904 is perpendicular to the major axis of the sleeper section. That is to say, the linear array 1904 can be situated around the waist of a sleeper, perpendicular to the orientation of their body. In other implementations, the array 1904 can be positioned across different portions of the bed system 1900 (e.g., closer to a head portion of the bed system 1900, closer to a foot portion of the bed system 1900, etc.). However, curvilinear, mesh, and other non-linear arrangements are possible. For example, a mesh of 20 evenly spaced sensors may be used for a sleeper.

In some implementations, the bed system 1900 can have a single or combination of sensor arrays 1904. For example, a sensor array can be positioned closer to a head portion of the bed system 1900 and a second sensor array can be positioned closer to a foot portion of the bed system 1900. As another example, the array 1904 can be integrated into a top layer of the mattress 1902 or placed on the mattress 1902 under bedding, sheets, or a mattress cover.

The sensor array 1904 can include a plurality of sensors 1906A-N. As depicted in FIG. 19A, the array 1904 can include five sensors 1906A-N. In other implementations, fewer or more sensors can be included in the array 1904. In some implementations, one or more of the sensors 1906A-N can be integrated into the mattress surface 1902 or other portion(s) of the bed system 1900. One or more of the sensors 1906A-N can be temperature sensors. One or more of the sensors 1906A-N can also be pressure sensors. The sensors 1906A-N can be configured to measure temperature variations of the occupant 1908's body and/or from the mattress surface 1902 of the bed system 1900. These temperature readings can be sensed in real-time while the occupant 1908 is in the bed system 1900 (e.g., while the occupant 1908 is falling asleep and during different sleeping states or stages). One or more of the sensed temperature values can include a core body temperature (e.g., CBT, abdominal, thoracic, and cranial cavities, which contain the vital organs), shell body temperature (e.g., a temperature of the skin, subcutaneous tissue, and muscles), upper body temperature, lower body temperature, or any combination of these. Moreover, the sensors 1906A-N can measure the occupant 1908's skin temperature (e.g., distal and/or proximal), temperatures of one or more microclimates of the bed system 1900, and/or the mattress surface 1902 temperature(s).

At least one of the sensors 1906A-N can be more responsive to proximal temperature of the sleeper (e.g., occupant 1908) than to distal temperature of the sleeper. At least another of the sensors 1906A-N can be more responsive to distal temperature of the sleeper than to proximal temperature of the sleeper. In some implementations, each of the sensors 1906A-N can be at least partially responsive to proximal temperature of the sleeper and to distal temperature of the sleeper. Such responsiveness to different temperatures can be advantageous to then determine a distal-to-proximal temperature-gradient (DPG) for the occupant. This responsiveness can also be advantageous to determine different adjustments to the one or more microclimates of the bed system 1900. For example, a microclimate nearest to the occupant 1908's body where the proximal temperature reading was captured can be slightly increased while a microclimate nearest to the occupant 1908's body where the distal temperature reading was captured can be slightly decreased. Such changes in isolation and/or simultaneously can be advantageous to improve the occupant 1908's overall sleep quality and comfort and/or impact the occupant 1908's DPG The sensors 1906A-N can be in communication (e.g., wired and/or wireless) with a controller 1910. For example, the sensors 1906A-N can transmit temperature and/or pressure readings to the controller 1910. The controller 1910 can determine an overall skin temperature or DPG of the occupant 1908 based on a linear combination of the sensor readings from the sensors 1906A-N. The controller 1910 can then determine one or more optimal microclimates for the occupant 1908, as described further below. The controller 1910 can be configured to adjust temperatures in the different microclimates of the bed system 1900 to enhance the occupant 1908's sleep quality. Temperature values can be continuously captured and transmitted to the controller 1910 in real-time such that the controller 1910 can dynamically adjust temperatures in the different microclimates. As a result, the bed system 1900 can provide for seamless and continuous comfort and quality in the occupant's sleep.

The controller 1910 can also be configured to generate information about pressure from the occupant 1908 to determine a posture of the occupant 1908. The posture can be used to determine optimal microclimates and microclimate adjustments. The controller 1910 can also be configured to process generated information (e.g., optimal microclimate) to identify sleep parameters and/or temperature parameters of the occupant 1908 of the bed system 1900. For example, the controller 1910 can determine the occupant 1908's sleep quality based on whether they had a short sleep onset latency (e.g., less than 10 minutes), low sleep fragmentation (e.g., wake up after sleep onset is less than 20 minutes), long sleep duration (e.g., exceeding a standard deviation from a habitual sleep duration), longer deep sleep, longer REM sleep, and/or subjective feedback from the occupant 1908. The subjective feedback can be a sleep satisfaction report in a questionnaire that the occupant 1908 completes. The subjective feedback can also be a measure of subjective daytime sleepiness. The controller 1910 can use this information to optimize microclimates and continuously provide the occupant 1908 with improved quality of sleep.

As described throughout this disclosure, the controller 1910 can be a device (e.g., mobile device, smart phone, tablet, computer, etc.) that can be configured to adjust one or more features of the bed system 1900. For example, the controller 1910 can change a temperature of the bed system 1900. As additional examples, the controller 1910 can be configured to adjust a bedroom feature such as temperature. As described herein, the controller 1910 can indirectly adjust a body temperature of the occupant 1908 by adjusting temperatures of one or more microclimates of the bed system 1900. For example, slight, occupant-unrecognizable temperature adjustments can be made to the microclimates of the bed system 1900 based on the calculated DPG the occupant 1908's biometric data, sleep stages, position/posture, circadian rhythm, cardiac measures (e.g., HR, HRV, etc.) and/or configurable settings (e.g., a time-delay, wake-up alarm, sleep routine, etc.). The controller 1910 can also engage in thermoregulation based on the occupant 1908 being out of bed, in bed and awake, and/or in bed and asleep.

Additionally or alternatively, the controller 1910 can control the bed system 1900 before the occupant 1908 enters. For example, the controller 1910 can increase or decrease temperatures of one or more microclimates of the bed system 1900 to encourage the occupant 1908 to fall asleep faster than otherwise. The controller 1910 can make such temperature adjustments based on analyzing historic data about the occupant 1908 (e.g., average DPG CBT, skin temperature, sweating, posture, etc.). In-bed-awake thermoregulation can also be performed by the controller 1910 to help the occupant 1908 fall asleep faster. In-bed-asleep thermoregulation can help the occupant 1908 maintain body temperature and prevent them from overcooling or overheating, depending on sleep stages, to maximize deep and REM sleep. In-bed-asleep thermoregulation can further be used in conjunction with a wake alarm or wake-up routine to change a temperature within a predefined wake period to ease the occupant 1908's transition to light stages of sleep and help them wake up feeling refreshed.

Still referring to FIG. 19A, the controller 1910 can be configured to determine the distal-proximal temperature-gradient (DPG) for the occupant 1908, as described herein. The DPG can then be used by the controller 1910 to adjust one or more microclimates of the bed system 1900 to provide the occupant 1908 with improved sleep quality. As described further below, to determine the DPG the controller 1910 can communicate with a remote server 1912 and access one or more look-up tables 1914A-N. The remote server 1912 can be a computer, database, network of computers, cloud storage, or any other type of data store. The look-up tables 1914A-N can associate temperature values with corresponding weight-values. The weight-values can be indexed by a sleep posture and/or a sensor identifier. The controller 1910 can use one or more of the look-up tables 1914A-N to determine the occupant 1908's DPG as well as adjustments that can be made to microclimates of the bed system 1900 to improve the occupant 1908's quality of sleep (e.g., increase or decrease one or more temperatures of the bed system 1900).

Figure 19B:
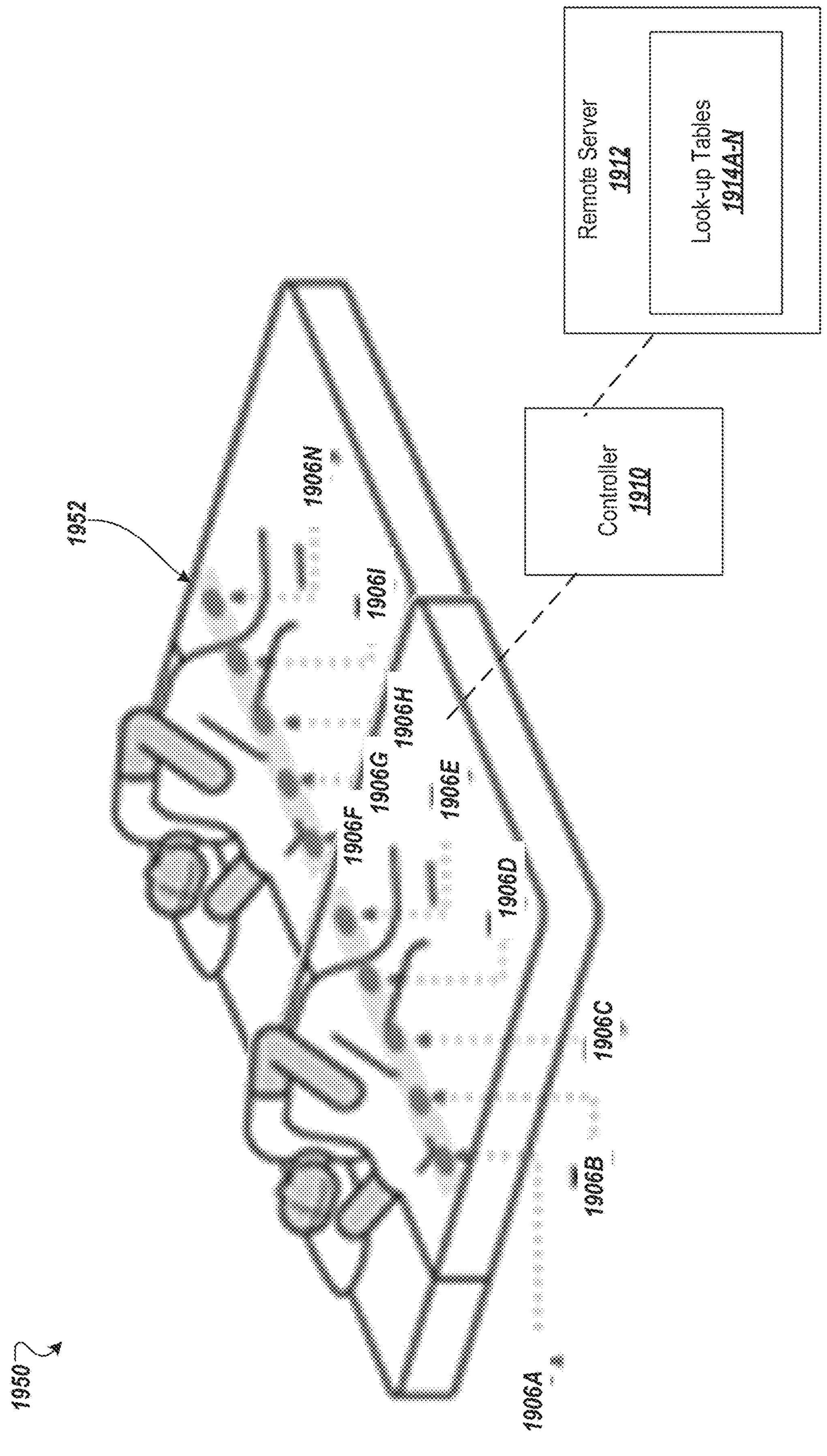
FIG. 19B is another example bed system with a sensor array.

FIG. 19B is another example bed system 1950 with a sensor array 1952 of sensors 1906A-N. As shown here, this technology can be used in beds designed for two sleepers (e.g., sometimes called Twin, Queen, or King sized). As will be understood, the orientation of the array may different than what is shown in this example, and may be oriented based on considerations including the physical architecture of the mattress, sensor design, wiring considerations, etc. In some cases, the orientation may be different for the two different sides of the bed.

Figure 20A:
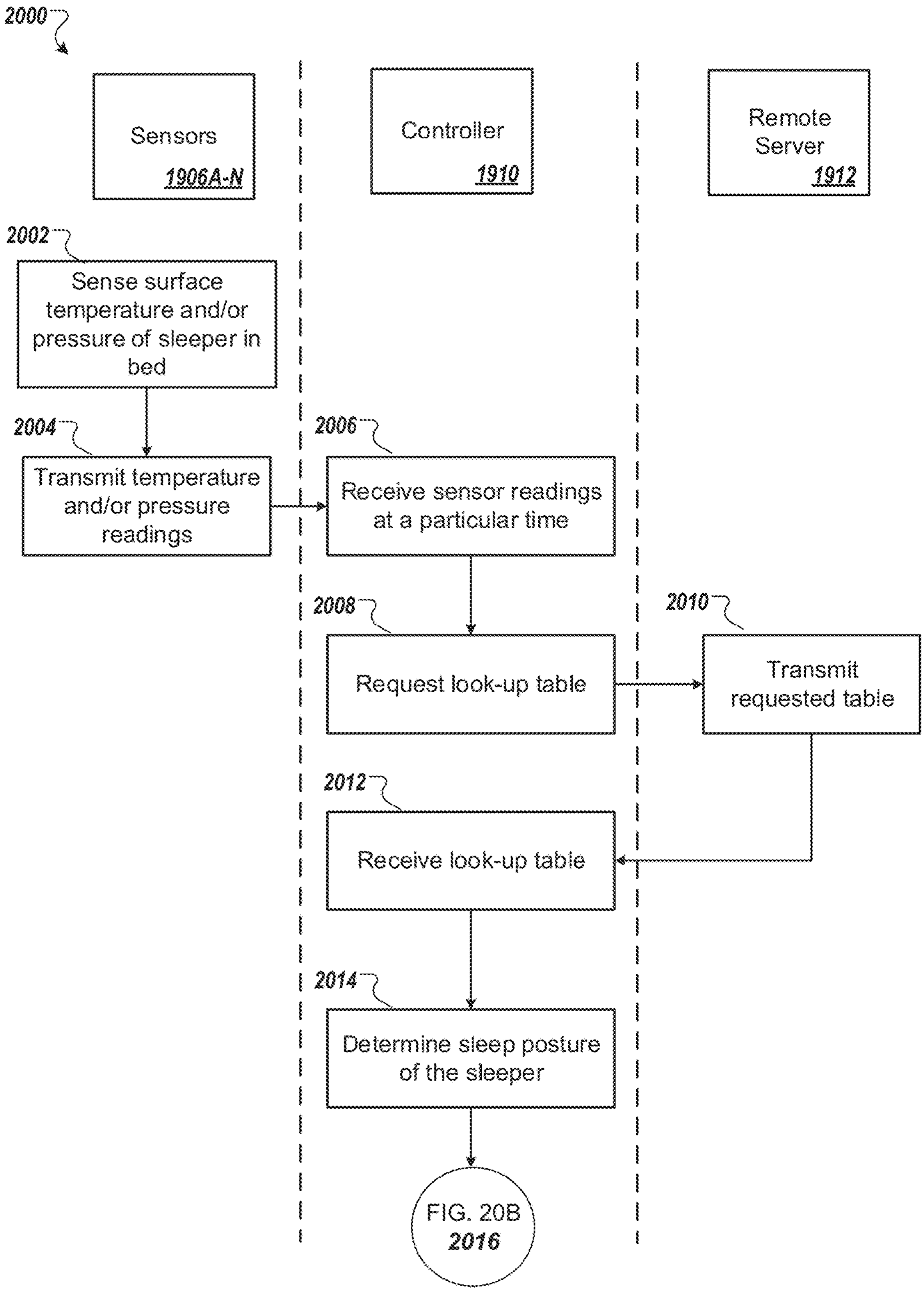
FIGS. 20A-B are a swimlane diagram of an example process for determining a distal-proximate temperature-gradient (DPG) for an occupant of the bed systems of FIGS. 19A-B.
Figure 20B:
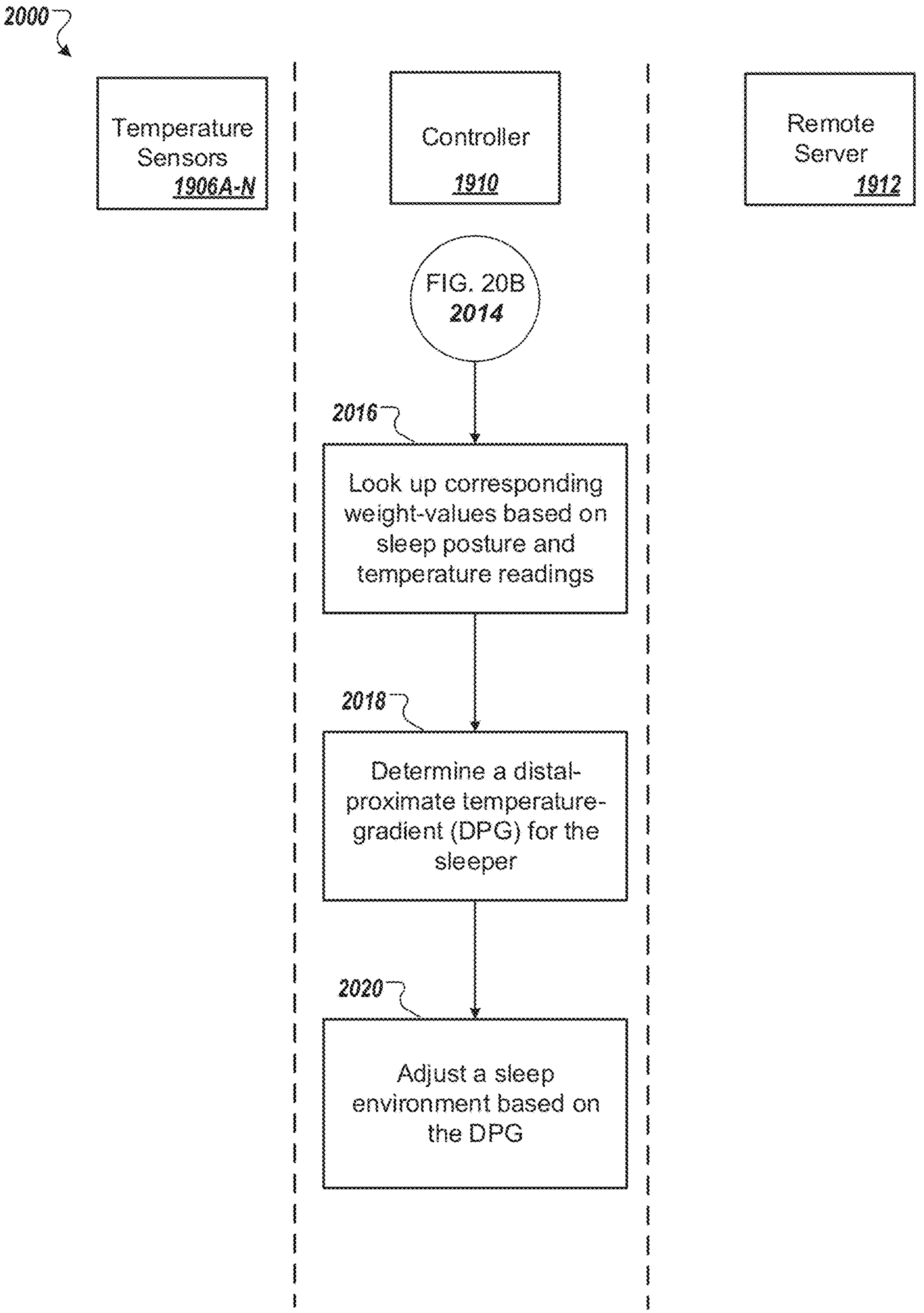

FIGS. 20A-B are a swimlane diagram of an example process 2000 for determining a distal-proximate temperature-gradient (DPG) for an occupant (e.g., sleeper) of the bed system of FIGS. 19A-B. For clarity, the process 2000 is being described with reference to components of the bed system 1900. However, another system or systems can be used to perform the same or a similar process.

Referring to both FIGS. 20A-B, the process 2000 can begin, for example, when the sensors 1906A-N sense a surface temperature and/or pressure of a sleeper in the bed (2002). One or more of the sensors 1906A-N can be configured to sense surface temperatures of the sleeper (e.g., body temperatures, skin temperatures) and another one or more of the sensors 1906A-N can be configured to sense pressure readings of the sleeper. In some implementations, the sensors 1906A-N can be configured to sense both temperatures and pressure readings. In some implementations, other sensors such as a pressure transducer (described above) may sense pressure under-sleeper air bladders, etc.

The sensors 1906A-N can transmit the temperature and/or pressure readings in 2004. The controller 1910 can receive the sensor readings at a particular time in 2006. The particular time can be in real-time, such as at a moment that the sensor readings are captured by the sensors 1906A-N. The sensors 1906A-N can capture sensor readings continuously or on an otherwise ongoing basis and transmit those readings to the controller 1910. In some implementations, the sensors 1906A-N can capture sensor readings at predetermined times. In yet other implementations, the controller 1910 can request one or more of the sensors 1906A-N to capture sensor readings and transmit those readings to the controller 1910.

The controller 1910 can request a look-up table (2008). Thus, once the controller 1910 receives the sensor readings, the controller 1910 can access, for each temperature reading, corresponding weight-values in the look-up table. The look-up table can record the weight-values (e.g., coefficients). These weight-values can be indexed by sleep posture (e.g., the sleeper is on their back, on their side, prone, etc.) and/or sensor identifier (e.g. the sensor is configured to sense temperature values, the sensor is configured to sense pressure readings, etc.). Moreover, the weight-values can be indexed based on most popular or common sleep postures for the particular sleeper and/or a general population of sleepers.

The remote server 1912 can receive the request and transmit the requested look-up table in 2010. The controller 1910 can receive the look-up table in 2012. The controller 1910 can determine a sleep posture of the sleeper (2014). The sleep posture can be determined based on one or more pressure readings sensed by the sensors 1906A-N (e.g., refer to FIG. 22). While a look-up table is described here, it will be understood that other schemes for determining weight-values may be used, including algorithmically calculating the weight-values.

Using the look-up table, the controller 1910 can look up corresponding weight-values for the sleeper based on the determined sleep posture and temperature readings from the sensors 1906A-N (2016). The controller 1910 can determine the distal-proximate temperature-gradient (DPG) for the sleeper in 2018. Thus, the controller 1910 can determine the DPG at the particular time using the temperature readings and the corresponding weight-values. For example, the controller 1910 can be configured to find weighted-temperatures by weighing each of the temperature readings by the corresponding weight-values. The controller 1910 can also find an aggregate of the weighted temperatures, which can be the DPG The controller 1910 can also be configured to use cardiac measures (e.g., heartrate, heartrate variability) of the sleeper to determine the DPG (e.g., refer to FIG. 22).

In some implementations, each weight-value can be a number between zero and one, inclusive. To weigh each of the temperature readings by the corresponding weight-value, the controller 1910 can further be configured to multiply each of the temperature readings by the corresponding weight-value. The aggregate can be a sum of the weighted temperatures. In other examples, the aggregate can be an average of the weighted temperatures. In yet other examples, the aggregate can be a mean of the weighted temperatures.

The controller 1910 can adjust a sleep environment based on the DPG (2020). For example, the controller 1910 can be configured to engage one or more thermal controllers to adjust the sleep environment to a target thermal environment determined using the DPG (e.g., refer to FIG. 21). As another example, the controller 1910 can use the determined DPG to engage the one or more thermal controllers to adjust the sleep environment until a target DPG is detected.

As yet another example, the controller 1910 can use the DPG to annotate sleep-session information for the sleeper stored in a data store. Moreover, the controller 1910 can generate sleep-quality information for the sleeper's sleep session at the particular time, based on the DPG The sleep-quality information can be generated using at least one of the group that includes: sleep onset latency, sleep fragmentation, length of deep sleep, length of REM sleep, and subjective assessment of sleep by the sleeper after the sleep session. In another example, the controller 1910 can use the DPG to generate a wellness metric for the sleeper, such as cardiovascular health or conditions.

Figure 21:
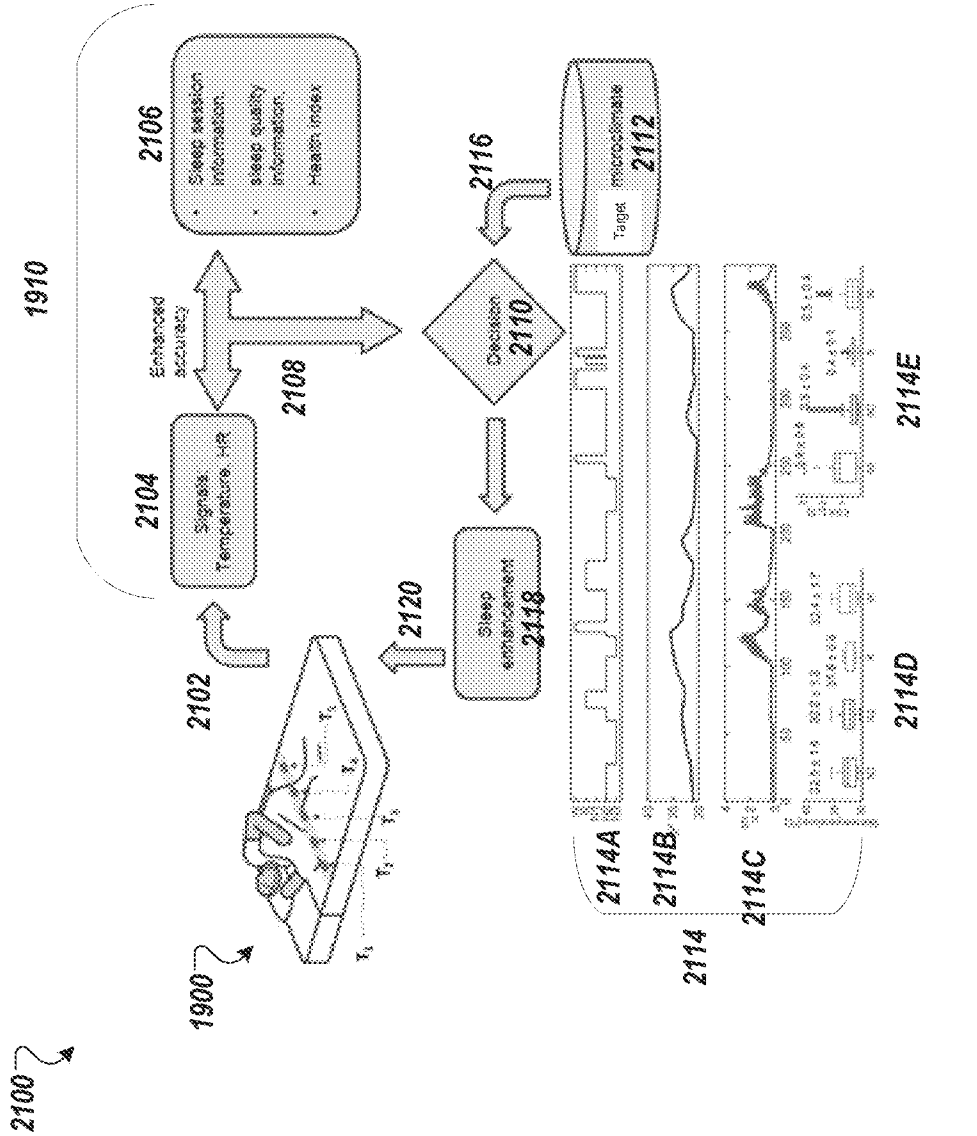
FIG. 21 is a block diagram for adjusting a microclimate of the bed system of FIGS. 19A-B.

FIG. 21 is a block diagram 2100 for adjusting one or more microclimates of the bed system 1900 of FIGS. 19A-B. As depicted, temperature readings can be sensed at the bed system 1900 by temperature sensors and transmitted 2102 to the controller 1910. Example inputs 2104 that the controller 1910 can receive from the bed system 1900 can include temperature, heartrate, and/or pressure signals. Using additional information 2106, such as sleep-session information, sleep quality information, and a health index, the controller 1910 can ensure accuracy 2108 of the signals 2104. The controller 1910 can then determine 2110 a DPG of the bed occupant (e.g., refer to FIG. 20).

For example, in some embodiments, a skin temperature can correspond to distal temperature ($T_{DIST}$). In other embodiments, skin temperature can correspond to proximal temperature ($T_{PROX}$). As described throughout this disclosure, the skin temperature can be the distal-to-proximal temperature-gradient (DPG) ($T_{DPG}=T_{DIST}-T_{PROX}$). $T_{DPG}$ can be approximated using the following:

$$T_{DPG}=\sum_{i=1}^{N}\lambda_i T_i,$$

Figure 22:
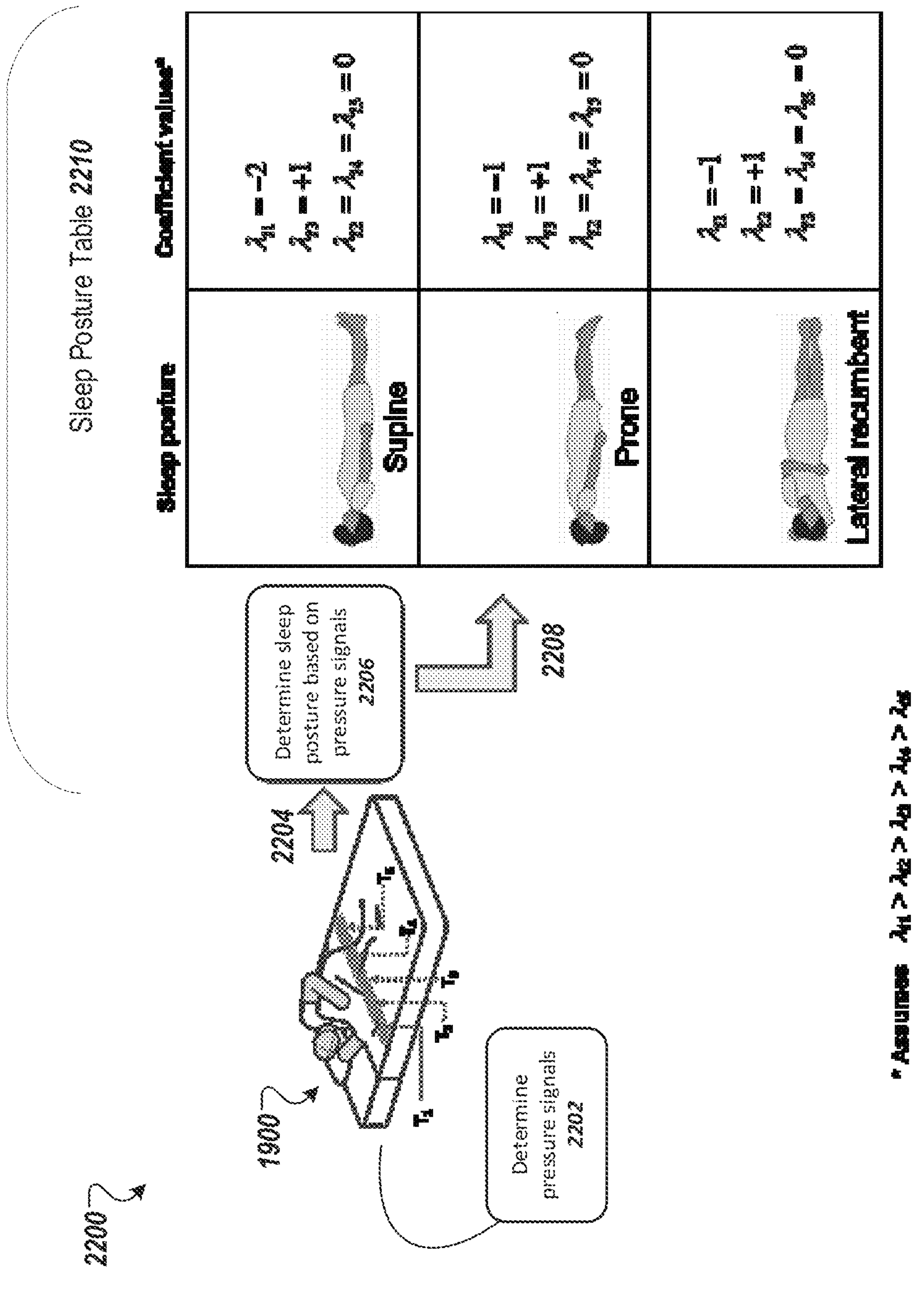
FIG. 22 is a schematic diagram for determining a sleep posture of an occupant of the bed system of FIGS. 19A-B.

Ti can be a temperature reading from an i-th sensor in the array (e.g., refer to FIGS. 19A-B) and λi can be a corresponding weighting coefficient that is estimated from calibration data (e.g., refer to FIGS. 20A-B, 22).

The controller can access 2116 a target microclimate database 2112 with target microclimate information 2114. The information 2114 can include one or more graphs about sleeping states and/or conditions of the bed occupant. For example, graph 2114A can be a hypnogram that depicts different sleeping states of the bed occupant. Graph 2114B can depict skin temperatures of the occupant during different sleeping states. Graph 2114C can depict sweat activity on the occupant's skin while the occupant is sleeping. Graph 2114D can depict a histogram of body temperatures during different sleeping states. Graph 2114E can depict a histogram of an amount that the occupant sweats during different sleeping states. This information 2114 can be used to determine one or more target microclimates for the occupant to improve the occupant's sleep quality. As an example, one microclimate can be associated with proximal temperatures of the occupant's body. Another microclimate can be associated with distal temperatures of the occupant's body. An additional microclimate can also be associated with a core body temperature of the occupant. One or more additional or fewer microclimates can be established based on information 2114 of the occupant.

Using the information 2114, the controller can determine 2110 one or more adjustments or sleep enhancements to make to the bed system that can improve the occupant's quality of sleep. For example, an adjustment can be a minimal increase and/or decrease in a temperature of one or more microclimates. As described herein, the bed system can include one or more microclimates associated with different portions of the occupant's body and/or different temperatures of the occupant's body. Each of these microclimates can be adjusted simultaneously or at different times and together or independent of each other when determining 2110 the sleep enhancements.

The determined sleep enhancement(s) 2118 can be transmitted 2120 to the bed system 1900. The bed system 1900 can perform these sleep enhancement(s) 2118. As an example, a temperature of a microclimate closest to the occupant's core can be decreased while a temperature of another microclimate closest to the occupant's feet can be increased.

As depicted in FIG. 21, 2100 can be a closed feedback loop. Dynamic and continuous sleep enhancement(s) and/or adjustments can be made at any particular time and/or based on temperature changes sensed in real-time. For example, a first adjustment can be to decrease a temperature of the bed system 1900 closest to the core of the occupant's body. Temperature readings can be captured after this adjustment is made and used by the controller to determine whether a core body temperature (CBT) of the occupant has increased or decreased. If, for example, the CBT decreased, as a result of the adjustment to the temperature of the bed system 1900, the controller can determine that the temperature of the bed system 1900 (e.g., at one or more microclimates) should be increased to maintain an optimal CBT of the occupant during different sleeping states or stages.

FIG. 22 is a schematic diagram 2200 for determining a sleep posture of an occupant of the bed system 1900 of FIGS. 19A-B. As depicted, pressure signals can be determined 2202 at the bed system 1900 (e.g., refer to the sensors 1906A-N in FIGS. 19A-B). The pressure signals can be transmitted 2204 to the controller 1910. The controller 1910 can determine a sleep posture based on the pressure signals 2206. For example, the controller 1910 can access 2208 a sleep posture look-up table 2210. The table 2210 can be stored at a remote server, in a cloud, or other type of data store, as described throughout this disclosure.

As depicted in FIG. 22, the table 2210 can match different sleep postures with coefficient values (e.g., weight-values). The sleep postures can include supine, prone, and/or lateral recumbent. One or more additional or fewer sleep postures can also be included in the table 2210 and/or one or more other sleep posture look-up tables. The table 2110 can also consider most frequent (e.g., top 3) sleep postures when setting the corresponding coefficient weight-values. The coefficient values can be weight-values that are used by the controller 1910 to determine a DPG of the bed occupant (e.g., refer to FIGS. 20A-B) and/or optimal microclimates. For example, the DPG can be determined by reading linear temperature values that are sensed by an array of sensors on the bed system 1900, as described herein. Depending on a position or posture of the occupant, corresponding weight-values or coefficients can be used to adjust the sensors and/or sensed temperature values.

As an example, $\lambda_i$ values and approximate $T_{DPG}$ can be set by modeling the bed occupant's body as a rectangle having a highest temperature value near its center and a lowest temperature near the edges of the rectangle. The sensed temperature values can then be sorted. A highest temperature can be presumed as closest to a core of the occupant's body since the core typically has a higher temperature than other parts of the body. In the linear array, temperatures farther away from the center or core temperature can have lower or higher relative coefficient values. The coefficient values can also be changed or modified based on a position or posture of the occupant.

As another example, the $\lambda_i$ coefficients can be determined by creating an empirical linear regression model to approximate ground-truth (or calibration) data, such as cardiac measures. Sleep stages can be detected through cardiovascular metrics (e.g., heartrate, heartrate variability). One or more cases can be distinguished based on the detected cardiovascular metrics: (1) during the falling asleep process, the bed system 1900 can deliver heats to increase $T_{DPG}$; heat delivery can stop if sleep onset is detected, (2) if the sleep stage is N3 sleep, then the bed system 1900 can deliver heat to increase $T_{DPG}$ by 0.2 □C, and (3) in REM, N2, or N1, no heat can be delivered or withdrawn. In other embodiments, $T_{DPG}$ can be adjusted without considering sleep stages but to lower heart rate and/or increase heart-rate variability. In yet other embodiments, core body temperature (CBT) can be used in a closed loop algorithm, as described throughout this disclosure, and can be estimated with an empirical model:

$$T_{CBT} = \sum_{i=1}^{N} c_i T_i + c_{HR} HR + c_{HRV} HRV,$$

where $c_i$, $c_{HR}$, and $c_{HRV}$ can be empirically estimated coefficients. Such an empirical model can take into account signals from the temperature sensors as well as cardiac metrics including heart rate (HR) and heart rate variability (HRV). Thus, adding together estimations of HR, HRV, and temperatures from the sensors can provide for more accurate predictions of CBT. During at least some stages of sleep, HR can be positively correlated with CBT and HRV can be negatively correlated with CBT. These cardiac measures can be added to the aggregate temperature readings from the sensors in order to more accurately determine the occupant's CBT.

As a result, information such as body temperatures and cardiac metrics can be used to adjust one or more microclimates of the bed system 1900 as described herein. For example, the lower an environmental temperature is, such as a surface temperature of the mattress, the higher HRV in a first half of the night. The higher the HRV, it is believed, the lower risk that the occupant experiences negative cardiovascular outcomes or health conditions. Therefore, the disclosed technology can be used to modulate one or more temperatures of different microclimates in the bed system 1900 to provide the occupant with improved sleep quality and cardiovascular health.

In other configurations, different coefficients may be used. For example, coefficients A0, A1, A2, A3, A4 and A5 may be used, with a one-to-one coefficient-to-sensor pairing, and the sixth coefficient applied to additively as a constant, for example. In one configuration, the values for A0-A5 may be 33.69, −0.05, −0.05, −0.03, 0.19, −0.03, −0.18

As described throughout this disclosure, temperature in a microclimate of the bed system 1900 can be adjusted by increasing the DPG linearly by fractions of degrees. Such minimal incremental increases in temperature in one or more microclimates of the bed system 1900 can be advantageous to induce more sleepiness in the occupant. Moreover, the minimal increases in temperature may not be directly and/or immediately felt by the occupant. Thus, the occupant may not be woken up or disturbed by changes in temperatures of the bed system 1900. This can improve overall sleep quality for the occupant.

In some implementations, DPG can be adjusted by decreasing a proximal temperature while keeping a distal temperature constant. As another example, DPG can be adjusted by decreasing the distal temperature and keeping the proximal temperature constant. DPG can also be adjusted by increasing the proximal temperature while keeping the distal temperature constant. DPG can further be adjusted by increasing the distal temperature and keeping the proximal temperature constant. In other words, one or more microclimates of the bed system 1900 can be individually controlled to improve the overall DPG of the occupant, which can have positive effects on improving sleep quality of the occupant and reducing cardiovascular health conditions.

In some implementations, one microclimate can be adjusted by increasing the distal temperature for that microclimate. Another microclimate can be adjusted by increasing just the proximal temperature for that microclimate. Individually adjusting temperatures for each of these microclimates or zones of the bed system 1900 can provide for overall improved quality of sleep for the bed occupant. This is advantageous where, for example, the occupant may have a high core temperature but colder feet. This discomfort can be alleviated by, for example, increasing a temperature of a microclimate proximate to the feet while decreasing a temperature of a microclimate proximate to the occupant's center point or core. As a result, the occupant can have an improved quality of sleep.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A sensor system for determining a distal-proximal temperature-gradient of a sleeper, the system comprising:

a bed having a mattress having a foot of the mattress;

an array of temperature sensors arranged in a single linear array arranged parallel to the foot of the mattress, each sensor configured to:

sense surface temperature of the sleeper of the bed; and transmit, to a controller, temperature readings;

a controller comprising a processor and memory, the controller configured to:

receive, from each of the sensors, temperature readings at a particular time;

access, for each temperature reading, a corresponding weight-value;

determine the distal-proximal temperature-gradient for the sleeper at the particular time using the temperature readings and the corresponding weight-values; and use the distal-proximal temperature-gradient to engage one or more thermal controllers to adjust the sleep environment until a target distal-proximal temperature-gradient is detected.

2. The sensor system of claim 1, wherein:

the linear array has a linear axis;

the bed has a sleeper section adapted to support the sleeper, the sleeper section has a major axis through a center of a longest dimension of the sleeper section; and where the linear array is situated so that the linear axis is perpendicular to the major axis.

3. The sensor system of claim 1, wherein:

at least one of the sensors is more responsive to proximal temperature of the sleeper than to distal temperature of the sleeper; and at least another of the sensors is more responsive to distal temperature of the sleeper than to proximal temperature of the sleeper.

4. The sensor system of claim 3, wherein each of the sensors is at least partially responsive to proximal temperature of the sleeper and to distal temperature of the sleeper.

5. The sensor system of claim 1, wherein the array of temperature sensors consists of five temperature sensors.

6. The sensor system of claim 1, wherein:

a lookup table records the weight-values in a look-up table indexed by sleep posture and sensor identifier; and to access, for each temperature reading, a corresponding weight-value, the controller is further configured to:

look up, in the look-up table, the corresponding weight-values using the sleep posture of the sleeper and sensor identifiers of the temperature sensors.

7. The sensor system of claim 6, wherein pressure readings from a pressure sensor are used by the controller to determine the sleep posture of the sleeper.

8. The sensor system of claim 1, wherein to determine the distal-proximal temperature-gradient for the sleeper at the particular time using the temperature readings and the corresponding weight-values, the controller is further configured to:

find weighted-temperatures by weighing each of the temperature readings by the corresponding weight-value; and find an aggregate of the weighted temperatures.

9. The sensor system of claim 8, wherein:

each weight-value is a number between zero and one, inclusive; and to weigh each of the temperature readings by the corresponding weight-value, the controller is further configured to multiply each of the temperature readings by the corresponding weight-value.

10. The sensor system of claim 8, wherein the aggregate is a linear combination of temperatures.

11. The sensor system of claim 1, wherein to determine the distal-proximal temperature-gradient for the sleeper at the particular time using the temperature readings and the corresponding weight-values, the controller is further configured to use cardiac measures of the sleeper.

12. The sensor system of claim 1, wherein the controller is further configured to engage one or more thermal controllers to adjust the sleep environment to a target thermal environment determined using the distal-proximal temperature-gradient.

13. The sensor system of claim 1, wherein the controller is further configured to use the distal-proximal temperature-gradient to annotate sleep-session information for the sleeper stored in a data store.

14. The sensor system of claim 1, wherein the controller is further configured to use the distal-proximal temperature-gradient to generate sleep-quality information for the sleeper's sleep session at the particular time.

15. The sensor system of claim 14, wherein the controller is further configured to generate the sleep-quality information using at least one of the group comprising: sleep onset latency, sleep fragmentation, length of deep sleep, length of REM sleep, and subjective assessment of sleep by the sleeper after the sleep session.

16. The sensor system of claim 1, wherein the controller is further configured to use the distal-proximal temperature-gradient to generate a wellness metric for the sleeper.

17. A controller for determining a distal-proximal temperature-gradient of a sleeper, the controller comprising memory and one or more processors, the controller configured to:

receive, from each of a plurality of sensors arranged in a single linear array arranged parallel to a head of a mattress, each sensor configured to sense surface temperature of the sleeper of a bed, temperature readings at a particular time;

access, for each temperature reading, a corresponding weight-value;

determine the distal-proximal temperature-gradient for the sleeper at the particular time using the temperature readings and the corresponding weight-values; and use the distal-proximal temperature-gradient to engage one or more peripheral controllers to adjust the sleep environment.

18. A computer-readable medium tangibly storing instructions for determining a distal-proximal temperature-gradient of a sleeper, the instructions configured to, when executed by one or more processors, cause the processors to perform operations comprising:

receiving, from each of a plurality of sensors arranged in a single linear array arranged parallel to a foot of a mattress, each sensor configured to sense surface temperature of the sleeper of a bed, temperature readings at a particular time;

accessing, for each temperature reading, a corresponding weight-value;

determining the distal-proximal temperature-gradient for the sleeper at the particular time using the temperature readings and the corresponding weight-values; and using the distal-proximal temperature-gradient to annotate sleep-session information for the sleeper stored in a data store.

* * * * *